(12) United States Patent
Hu et al.

(10) Patent No.: US 11,040,952 B2
(45) Date of Patent: Jun. 22, 2021

(54) PHTHALAZINONE COMPOUND, METHOD FOR PREPARATION THEREOF, PHARMACEUTICAL COMPOSITION THEREOF, AND USE THEREOF

(71) Applicant: SHANGHAI INSTITUTE OF MATERIA MEDICA, CHINESE ACADEMY OF SCIENCES, Shanghai (CN)

(72) Inventors: Youhong Hu, Shanghai (CN); Jianping Zuo, Shanghai (CN); Dong Lu, Shanghai (CN); Li Yang, Shanghai (CN); Limin Zeng, Shanghai (CN); Feifei Liu, Shanghai (CN); Yunzhe Zhang, Shanghai (CN); Wuhong Chen, Shanghai (CN); Xiankun Tong, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 16/786,710

(22) Filed: Feb. 10, 2020

(65) Prior Publication Data

US 2020/0181109 A1 Jun. 11, 2020

Related U.S. Application Data

(63) Continuation of application No. PCT/CN2018/099806, filed on Aug. 10, 2018.

(30) Foreign Application Priority Data

Aug. 10, 2017 (CN) .......................... 201710681892.X

(51) Int. Cl.
| | |
|---|---|
| *C07D 401/04* | (2006.01) |
| *A61P 31/20* | (2006.01) |
| *C07D 401/14* | (2006.01) |
| *C07D 405/14* | (2006.01) |
| *C07D 413/14* | (2006.01) |

(52) U.S. Cl.
CPC ............ *C07D 401/04* (2013.01); *A61P 31/20* (2018.01); *C07D 401/14* (2013.01); *C07D 405/14* (2013.01); *C07D 413/14* (2013.01)

(58) Field of Classification Search
None
See application file for complete search history.

(56) References Cited

U.S. PATENT DOCUMENTS

2011/0105509 A1* 5/2011 Kaila ..................... A61P 17/00
514/248

FOREIGN PATENT DOCUMENTS

| CN | 104003940 A | 8/2014 | |
|---|---|---|---|
| CN | 104887680 A | 9/2015 | |
| JP | 3120857 B2 * | 12/2000 | .............. A61P 11/06 |
| WO | WO 2011/055270 A1 | 5/2011 | |

OTHER PUBLICATIONS

Machine Translation of JP 3120857 B2.*
Written Translation of Examples 61 and 97 of JP 3120857 B2.*

* cited by examiner

*Primary Examiner* — Joseph R Kosack
(74) *Attorney, Agent, or Firm* — Reinhart Boerner Van Deuren P.C.

(57) ABSTRACT

Provided are a phthalazinone compound, method for preparation thereof, pharmaceutical composition thereof, and a use thereof; the structure of said phthalazinone compound is as represented by formula I; the compound of said formula I is targeted to a viral nucleocapsid; it can inhibit the replication of a virus by means of interference of the viral nucleocapsid, has a potent activity for inhibiting HBV DNA replication and a good liver targeting, can stably exist and enrich in the liver, and is a new and effective anti-HBV inhibitor.

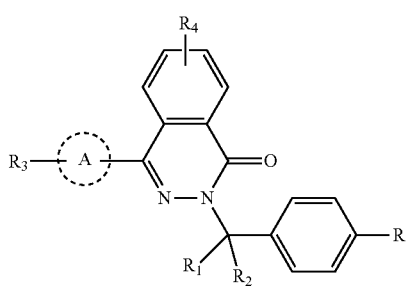

16 Claims, 1 Drawing Sheet

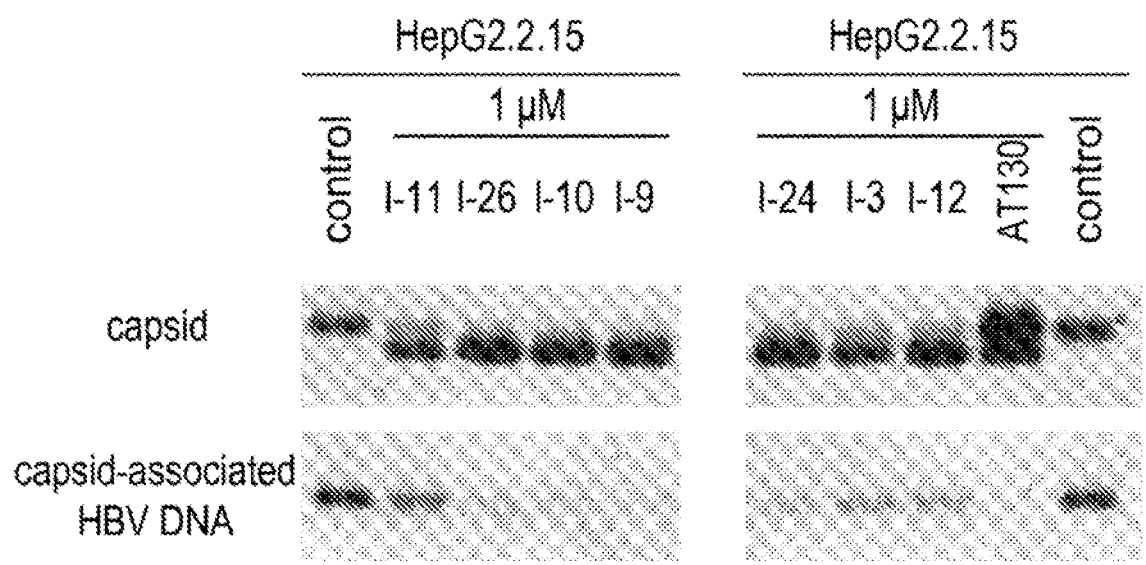

PHTHALAZINONE COMPOUND, METHOD FOR PREPARATION THEREOF, PHARMACEUTICAL COMPOSITION THEREOF, AND USE THEREOF

CROSS-REFERENCE TO RELATED PATENT APPLICATIONS

This patent application is a continuation of PCT/CN2018/099806, filed Aug. 10, 2018, which claims priority to Chinese Application No. 201710681892.X, filed Aug. 10, 2017, the entire teachings and disclosure of which are incorporated herein by reference thereto.

TECHNICAL FIELD

The invention relates to a phthalazinone compound, and a preparation method, pharmaceutical composition and use thereof.

BACKGROUND

According to the statistics of World Health Organization, 2 billion people worldwide have been infected with the hepatitis B virus (HBV), and about 350-400 million people have chronic infection. About one million people die each year of cirrhosis, hepatic insufficiency, liver cancer, and other complications due to HBV infection. Therefore, HBV infection remains a world disease seriously harming public health.

So far, interferon and nucleoside anti-HBV drugs are the two main means for treating HBV infection. However, interferon has disadvantages including poor tolerance, adverse reactions, and high cost; and each of the 6 nucleoside drugs (lamivudine, adefovir, entecavir, telbivudine, tenofovir and clevudine) that have been marketed act on the HBV reverse transcriptase, and may produce drug resistance and side effects in different degrees during long-term treatment, which greatly limits the application of such drugs.

Therefore, it is increasingly urgent to research and develop more non-nucleoside small molecule anti-HBV drugs that act on new targets, have new mechanisms and new core structures, which is a hot topic in the field of medicinal chemistry, and has very important significance in theory, economy and society.

SUMMARY OF THE INVENTION

The invention provides a compound of formula I with a phthalazinone core structure, or a pharmaceutically acceptable salt, solvate or prodrug thereof.

The present invention provides the following technical solutions:

A compound of formula I or a pharmaceutically acceptable salt, solvate or prodrug thereof:

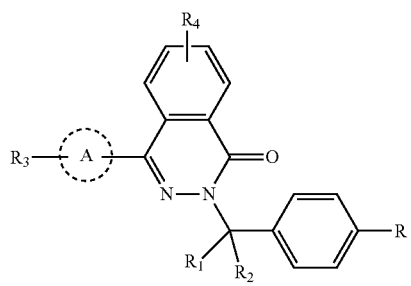

I wherein,
R is Cl or CN;
$R_1$ and $R_2$ are each independently H;
A is heteroaryl;
$R_3$ represents one or more substituents, each being independently selected from the group consisting of H, halogen, cyano, hydroxyl, alkyl, haloalkyl, optionally substituted cycloalkyl, optionally substituted heterocyclyl, optionally substituted heterochain hydrocarbyl, optionally substituted alkoxy, alkanoyloxy, —$(CH_2)_{n+1}R^5$, —$N(R^6)$—$(CH_2)_n(R^5)$;
$R_4$ represents one or more substituents, each being independently selected from the group consisting of H, halogen, cyano, hydroxyl, optionally substituted alkyl, optionally substituted alkoxy, alkanoyloxy;
$R^5$ and $R^6$ are each independently selected from the group consisting of H, hydroxyl, optionally substituted alkyl, optionally substituted cycloalkyl, optionally substituted alkoxy, alkanoyloxy, alkylsulfonyl, alkanoyl, alkoxyacyl, optionally substituted heterocyclyl, —$N(Q_1)(Q_2)$;
optionally, $R^5$ and $R^6$ are each independently selected from the group consisting of H, hydroxyl, optionally substituted alkyl, optionally substituted cycloalkyl, optionally substituted alkoxy, alkanoyloxy, optionally substituted heterocyclyl, —$N(Q_1)(Q_2)$;
in the "optionally substituted" groups, the substituent is selected from the group consisting of halogen, hydroxyl, alkyl, hydroxyalkyl, cycloalkyl, alkoxy, alkanoyl, alkoxyalkoxy, alkoxyacyl, carboxyl, heterocyclyl, —$N(Q_1)(Q_2)$;
optionally, in the "optionally substituted" groups, the substituent is selected from the group consisting of halogen, hydroxyl, alkyl, cycloalkyl, alkoxy, alkanoyl, heterocyclyl, —$N(Q_1)(Q_2)$;
wherein,
n is an integer selected from the group consisting of 0 to 10;
$Q_1$ and $Q_2$ are each independently H, alkyl or alkoxyacyl;
optionally, $Q_1$ and $Q_2$ are each independently H and alkyl;
preferably,
$R_3$ represents 1, 2 or 3 substituents;
$R_4$ represents 1 or 2 substituents;
the "heteroaryl" is a 5- to 10-membered heteroaryl containing 1 to 3 heteroatoms selected from the group consisting of N, O and S, optionally a 6- to 10-membered heteroaryl containing 1 to 2 heteroatoms selected from the group consisting of N, O and S, optionally, the heteroaryl includes pyridyl, pyrimidinyl, pyrazinyl, pyridazinyl, furyl, indolyl, azaindolyl, naphthyridinyl or quinolyl;
the "halogen" includes fluorine, chlorine, bromine and iodine;
the alkyl comprised in the "alkyl", "haloalkyl", "alkylsulfonyl", "alkoxyacyl", and "alkoxyalkoxy" is a $C_1$-$C_{18}$ linear or branched alkyl, optionally, the alkyl is a $C_1$-$C_7$ linear or branched alkyl, optionally, the alkyl is a $C_1$-$C_5$ linear or branched alkyl, optionally the alkyl includes methyl, ethyl, n-propyl, isopropyl, n-butyl, isobutyl, t-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, 2,2,3-trimethylbutyl; optionally, the "haloalkyl" includes trifluoromethyl;
the "alkoxy" is a $C_1$-$C_6$ linear or branched alkoxy, optionally, the alkoxy is a $C_1$-$C_5$ linear or branched alkoxy, optionally, the alkoxy is a $C_1$-$C_3$ linear or branched alkoxy, optionally, the alkoxy includes methoxy, ethoxy, n-propoxy, isopropoxy, n-butoxy, isobutoxy, t-butoxy, sec-butoxy, n-pentyloxy, isopentyloxy, neopentyloxy, n-hexyloxy, isohexyloxy, 3-methylpentyloxy;

the "alkanoyloxy" is a linear or branched $C_1$-$C_6$ alkanoyloxy, and optionally includes acetoxy;

the "cycloalkyl" is a $C_3$-$C_6$ cycloalkyl, optionally, the cycloalkyl includes cyclopropyl, cyclobutyl, cyclopentyl, cyclohexyl;

the heterocyclic structure in the "heterocyclyl" is a saturated or unsaturated 3- to 10-membered monocyclic or polycyclic non-aromatic ring structure containing 1, 2 or 3 heteroatoms selected from the group consisting of N, O, and S in the ring, optionally, the heterocyclyl is a 3- to 6-membered saturated ring containing N in the ring, optionally, the heterocyclyl is a 4- to 6-membered non-aromatic ring structure containing 1-2 heteroatoms selected from the group consisting of N and O in the ring, optionally, the heterocyclyl includes a tetrahydropyrrole ring, a tetrahydrothiophene ring or a tetrahydrofuran ring;

the heterochain hydrocarbon structure in the "heterochain hydrocarbyl" is a $C_1$-$C_7$ saturated or unsaturated, linear or branched heterochain structure containing 1-3 heteroatoms selected from the group consisting of N and O in the chain. Optionally, the heterochain hydrocarbyl is a $C_1$-$C_5$ saturated or unsaturated, linear or branched heterochain hydrocarbon structure containing 1-3 heteroatoms selected from the group consisting of N and O in the chain, optionally, the heterochain hydrocarbyl is a $C_1$-$C_5$ saturated or unsaturated, linear or branched heterochain hydrocarbon structure containing 1-3 oxygen atoms in the chain;

the "alkanoyl" is a $C_1$-$C_6$ linear or branched alkanoyl, optionally, the alkanoyl includes formyl, acetyl;

n is an integer selected from the group consisting of 0 to 5, optionally n is 0, 1, 2, 3, or 4.

Optionally, any one or more hydrogens in the compound of formula I or a pharmaceutically acceptable salt, solvate or prodrug thereof may be replaced by deuterium; optionally, the hydrogens represented by $R_1$ and $R_2$ may be each independently replaced by deuterium; optionally, any one or more hydrogens in one or more substituents represented by $R_3$ may be replaced by deuterium; optionally, any one or more hydrogens in one or more of H, alkyl, optionally substituted alkoxy, optionally substituted heterochain hydrocarbyl, —$(CH_2)_{n+1}R^5$ represented by $R_3$ may be replaced by deuterium.

Optionally, in the compound of formula I, or a pharmaceutically acceptable salt, solvate or prodrug thereof as described above:

R is Cl or CN;

$R_1$ and $R_2$ are each independently H or D;

A is pyridyl, pyrimidinyl or pyrazinyl;

$R_3$ represents one or more substituents, each being independently selected from the group consisting of H, D, halogen, cyano, hydroxyl, trifluoromethyl, methyl optionally substituted by one or more D, methylol, methoxymethyl optionally substituted by one or more D, acetoxymethyl, methoxy optionally substituted by one or more D, methoxyethoxy, amino, methylamino, dimethylamino, t-butylamino, cyclopropylamino, epoxypropylamino, acetylamino, oxetanylamino, methoxymethylamino, methoxyethylamino, methoxypropylamino, ethoxyethylamino, ethoxypropylamino, methoxycarbonylethylamino, methoxycarbonylpropylamino, ethoxycarbonylmethylamino, ethoxycarbonylethylamino, ethoxycarbonylpropylamino, hydroxyethylamino, hydroxypropylamino, hydroxybutylamino, cyclobutylamino, azetidinyl, N,N-dimethylaminomethylamino, N,N-dimethylaminoethylamino, N,N-dimethylaminopropylamino, N,N-dimethylaminobutylamino, t-butoxyacylaminobutylamino, 5-morpholinylmethyl, ethylaminoethylamino, ethylaminopropylamino, ethylaminobutylamino, methoxyethoxyethoxyethylamino, ethoxyethoxyethylamino, t-butoxycarbonylethylamino, t-butoxycarbonylpropylamino, t-butoxycarbonylmethoxyethylamino, carboxylethylamino, carboxylpropylamino, carboxymethoxyethylamino, 6-morpholinylmethyl, 6-(tetrahydrofuranyl)methylamino, methylsulfonylethylamino, (2,2-dimethyl-[1,3]-dioxolan-4-yl)-methylamino, 2,3-dihydroxypropylamino, 2-hydroxypropylamino, trifluoromethylethylamino;

optionally, $R_3$ represents one or more substituents, each being independently selected from the group consisting of H, D, halogen, cyano, trifluoromethyl, methyl optionally substituted by one or more D, methylol, methoxymethyl optionally substituted by one or more D, acetoxymethyl, methoxy optionally substituted by one or more D, amino, methylamino, dimethylamino, t-butylamino, cyclopropylamino, epoxypropylamino, acetylamino, oxetanylamino, methoxymethylamino, cyclobutylamino, azetidinyl, N,N-dimethylaminomethylamino, N,N-dimethylaminoethylamino, 6-morpholinylmethyl, 6-(tetrahydrofuranyl)methylamino;

$R_4$ represents one or more substituents, each being independently selected from the group consisting of H, halogen, methyl, methoxy, cyano and trifluoromethyl.

Optionally, in the compound of formula I, or a pharmaceutically acceptable salt, solvate or prodrug thereof as described above, the compound of formula I is selected from the group consisting of the compounds having a structure represented by one of the following formulae I-I to I-V:

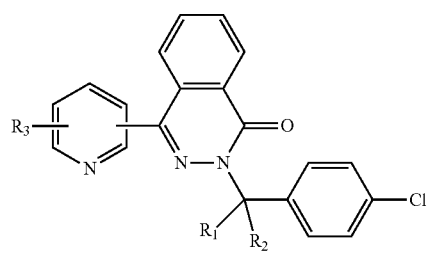

I-I

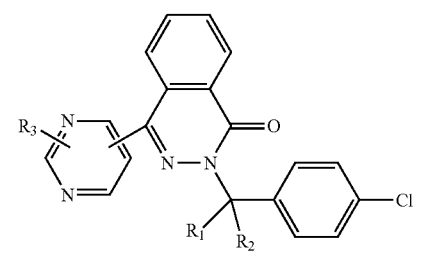

I-II

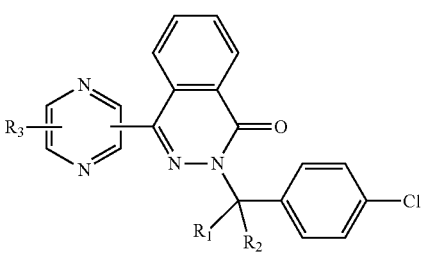

I-III

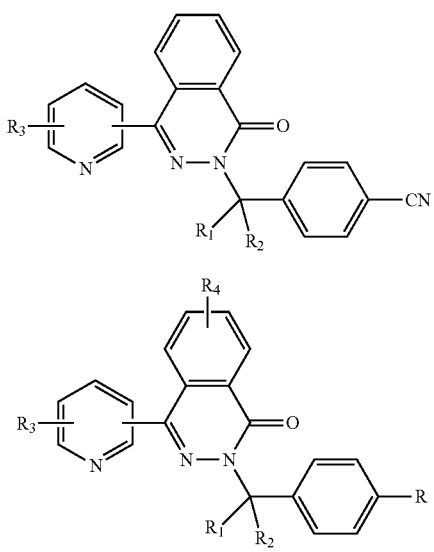

wherein, R, $R_1$, $R_2$, $R_3$ and $R_4$ are each independently defined as above;

preferably, in the formula I-I, $R_1$ and $R_2$ are each independently H or D; $R_3$ represents one or more substituents, preferably 1, 2 or 3 substituents, each being independently selected from the group consisting of H, D, halogen, cyano, $C_1$-$C_5$ linear or branched alkyl optionally substituted by one or more D, trifluoromethyl, $C_3$-$C_6$ cycloalkyl, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing 1-2 nitrogen atoms, —$(CH_2)_{n+1}R^5$ optionally substituted by one or more D, —$N(R^6)$—$(CH_2)_n(R^5)$; wherein, n is 0, 1, 2, 3 or 4; $R^5$ and $R^6$ are each independently H, hydroxyl, methyl, ethyl, propyl, isopropyl, butyl, isobutyl, $C_3$-$C_6$ cycloalkyl, methoxy, ethoxy, acetoxy, 4- to 6-membered non-aromatic heterocyclyl having 1-2 heteroatoms selected from the group consisting of N and O, or amino substituted by 1-2 substituents selected from the group consisting of methyl and ethyl;

preferably, in the formula I-II, $R_1$ and $R_2$ are each independently H or D; $R_3$ represents 1 or 2 substituents, each being independently selected from the group consisting of H, halogen, cyano, trifluoromethyl, $C_1$-$C_7$ linear or branched alkyl optionally substituted by one or more D, $C_1$-$C_6$ linear or branched alkoxy optionally substituted by one or more D, —$N(R^6)$—$(CH_2)_n(R^5)$; wherein, n is 0, 1, 2, 3 or 4; $R^5$ and $R^6$ are each independently H, halogen, methyl, ethyl, propyl, isopropyl, butyl or isobutyl;

preferably, in the formula I-III, $R_1$ and $R_2$ are each independently H or D; $R_3$ represents 1 or 2 substituents, each being independently selected from the group consisting of H, D, halogen, cyano, trifluoromethyl, $C_1$-$C_7$ linear or branched alkyl optionally substituted by one or more D, $C_1$-$C_6$ linear or branched alkoxy optionally substituted by one or more D or —$N(R^6)$—$(CH_2)_n(R^5)$; wherein, n is 0, 1, 2, 3 or 4; $R^5$ and $R^6$ are each independently H, methyl, ethyl, propyl, isopropyl, butyl;

preferably, in formula I-IV, $R_1$ and $R_2$ are each independently H or D; $R_3$ represents one or more substituents, preferably 1, 2 or 3 substituents, each being independently selected from the group consisting of H, D, halogen, cyano, hydroxyl, trifluoromethyl, $C_3$-$C_6$ cycloalkyl, $C_1$-$C_5$ linear or branched alkyl optionally substituted by one or more D, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing N (preferable 3- to 6-membered saturated heterocyclyl containing one nitrogen atom), —$(CH_2)_{n+1}R^5$ optionally substituted by one or more D, —$N(R^6)$—$(CH_2)_n(R^5)$; wherein, n is 0, 1, 2, 3 or 4; $R^5$ and $R^6$ are each independently H, hydroxyl, methyl, ethyl, propyl, isopropyl, butyl, isobutyl, t-butyl, $C_3$-$C_6$ cycloalkyl, methoxy, ethoxy, methoxyethoxyethoxy, ethoxyethoxy, acetyl, acetyloxy, methoxycarbonyl, ethoxycarbonyl, t-butoxycarbonyl, t-butoxycarbonylmethoxy, carboxyl, carboxymethoxy, 4- to 6-membered non-aromatic heterocyclyl with 1-2 heteroatoms selected from the group consisting of N and O, or amino substituted by 1-2 substituents selected from the group consisting of methyl, ethyl and t-butoxycarbonyl, methylsulfonyl, 2,2-dimethyl-[1,3]-dioxolan-4-yl, 2,3-dihydroxypropyl, 2-hydroxypropyl, trifluoromethylethyl;

optionally, in formula I-IV, $R_1$ and $R_2$ are each independently H or D; $R_3$ represents one or more substituents, preferably 1, 2 or 3 substituents, each being independently selected from the group consisting of H, D, halogen, cyano, trifluoromethyl, $C_3$-$C_6$ cycloalkyl, $C_1$-$C_5$ linear or branched alkyl optionally substituted by one or more D, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing N (preferable 3- to 6-membered saturated heterocyclyl containing one nitrogen atom), —$(CH_2)_{n+1}R^5$ optionally substituted by one or more D, —$N(R^6)$—$(CH_2)_n(R^5)$; wherein, n is 0, 1, 2, 3 or 4; $R^5$ and $R^6$ are each independently H, hydroxyl, methyl, ethyl, propyl, isopropyl, butyl, isobutyl, $C_3$-$C_6$ cycloalkyl, methoxy, ethoxy, acetoxy, 4- to 6-membered non-aromatic heterocyclyl with 1-2 heteroatoms selected from the group consisting of N and O, or amino substituted by 1-2 substituents selected from the group consisting of methyl and ethyl;

preferably, in formula I-V, R represents Cl or CN; $R_1$ and $R_2$ are each independently H or D; $R_3$ represents one or more substituents, preferably 1, 2 or 3 substituents, each being independently selected from the group consisting of H, D, halogen, cyano, hydroxyl, trifluoromethyl, $C_3$-$C_6$ cycloalkyl, $C_1$-$C_5$ linear or branched alkyl optionally substituted by one or more D, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing N, —$(CH_2)_{n+1}R^5$ optionally substituted by one or more D, —$N(R^6)$—$(CH_2)_n(R^5)$; wherein n is 0, 1, 2, 3 or 4; $R_4$ represents one or more substituents, preferably 1 or 2 substituents, each being independently selected from the group consisting of H, halogen, cyano, trifluoromethyl, methyl, ethyl, methoxy; $R^5$ and $R^6$ are each independently H, hydroxyl, methyl, ethyl, propyl, isopropyl, butyl, isobutyl, t-butyl, $C_3$-$C_6$ cycloalkyl, methoxy, ethoxy, methoxyethoxyethoxy, ethoxyethoxy, acetyl, acetoxyl, methoxycarbonyl, ethoxycarbonyl, t-butoxycarbonyl, t-butoxy carbonylmethoxy, carboxyl, carboxymethoxy, 4- to 6-membered non-aromatic heterocyclyl with 1-2 heteroatoms selected from the group consisting of N and O, or amino substituted by 1-2 substituents selected from the group consisting of methyl and ethyl, methylsulfonyl, 2,2-dimethyl-[1,3]-dioxolan-4-yl, 2,3-dihydroxypropyl, 2-hydroxypropyl, trifluoromethylethyl.

optionally, in formula I-V, R represents Cl or CN; $R_1$ and $R_2$ are each independently H or D; $R_3$ represents one or more substituents, preferably 1, 2 or 3 substituents, each being independently selected from the group consisting of H, D, halogen, cyano, trifluoromethyl, $C_3$-$C_6$ cycloalkyl, $C_1$-$C_5$ linear or branched alkyl optionally substituted by one or more D, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing N, —$(CH_2)_{n+1}R^5$ optionally substituted by one or more D, —$N(R^6)$—$(CH_2)_n(R^5)$; wherein n is 0, 1, 2, 3 or 4; $R_4$ represents one or more substituents, preferably 1 or 2 substituents, each being independently selected from the group consisting of H, halogen, cyano, trifluoromethyl, methyl, ethyl, methoxy; $R^5$ and $R^6$ are each independently H, hydroxyl, methyl, ethyl, propyl, isopropyl, butyl, isobutyl, $C_3$-$C_6$ cycloalkyl, methoxy, ethoxy, acetoxy, 4- to 6-membered non-aromatic heterocyclyl with 1-2 heteroatoms selected from the group consisting of N and O, or amino substituted by 1-2 substituents selected from methyl and ethyl.

Optionally, the compound of formula I, or a pharmaceutically acceptable salt, solvate or prodrug thereof as described above, is characterized in that:

the compound of formula I includes one or more optical isomers, enantiomers, diastereoisomers or racemate mixtures of the compound of formula I;

optionally, the pharmaceutically acceptable salt includes an anionic salt and a cationic salt of the compound of formula I; optionally, the pharmaceutically acceptable salt includes an alkali metal salt, an alkaline earth metal salt, an ammonium salt of the compound of formula I; optionally, the alkali metal includes sodium, potassium, lithium, cesium, and the alkaline earth metal includes magnesium, calcium, strontium; optionally, the pharmaceutically acceptable salt includes a salt formed by the compound of formula I and an organic base; optionally, the organic base includes trialkylamine, pyridine, quinoline, piperidine, imidazole, picoline, dimethylaminopyridine, dimethylaniline, N-alkylmorpholine, 1,5-diazabicyclo[4.3.0]non-5-ene, 1,8-diazabicyclo[5.4.0]undec-7-ene, 1,4-diazabicyclo[2.2.2]octane; optionally, the trialkylamine includes trimethylamine, triethylamine, N-ethyldiisopropylamine; optionally, the N-alkylmorpholine includes N-methylmorpholine; optionally, the pharmaceutically acceptable salt includes a salt formed by the compound of formula I and an acid; optionally, the acid includes an inorganic acid and an organic acid; optionally, the inorganic acid includes hydrochloric acid, hydrobromic acid, hydroiodic acid, sulfuric acid, nitric acid, phosphoric acid, carbonic acid; optionally, the organic acid includes formic acid, acetic acid, propionic acid, oxalic acid, malonic acid, succinic acid, fumaric acid, maleic acid, lactic acid, malic acid, citric acid, citric acid, tartaric acid, carbonic acid, picric acid, methanesulfonic acid, ethanesulfonic acid, p-toluenesulfonic acid, glutamic acid, pamoic acid;

optionally, the solvate is a complex formed by the compound of formula I and a pharmaceutically acceptable solvent; optionally, the pharmaceutically acceptable solvent includes water, ethanol, acetic acid, N,N-dimethyl formamide, dimethyl sulfoxide; preferably, the pharmaceutically acceptable solvent is water.

The prodrug refers to a compound obtained by modifying the chemical structure of a drug, which is inactive or less active in vitro, and takes effect in vivo by releasing an active drug through enzymatic or non-enzymatic conversion. The form of the prodrug in the present invention is not particularly limited, as long as it may release an active drug through enzymatic or chemical action in vivo, so as to exert the expected pharmacological effect, and it may be a carrier prodrug or a biological prodrug.

Optionally, the compound of formula I or a pharmaceutically acceptable salt, solvate or prodrug thereof, is characterized in that the compound of formula I is one of the following compounds:

I-1
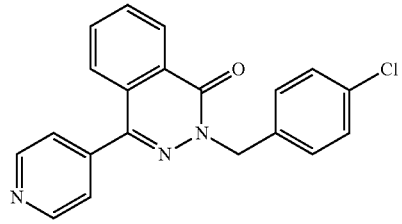

I-2
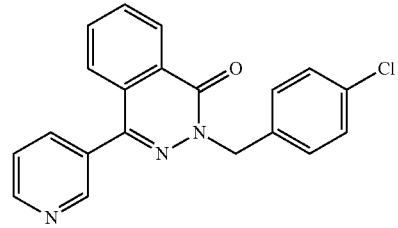 [SMILES: O=c1c2ccccc2c(-c2cccnc2)nn1Cc1ccc(Cl)cc1]

I-3
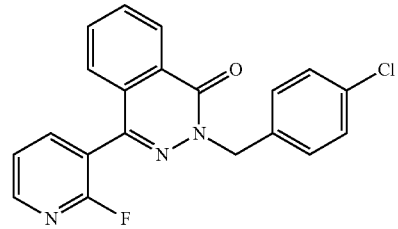

I-4
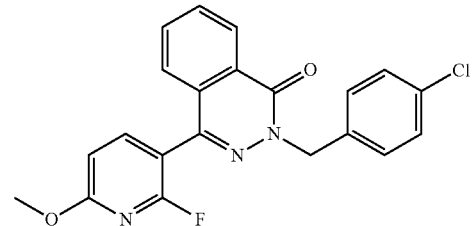 [SMILES: COc1ccc(-c2nn(Cc3ccc(Cl)cc3)c(=O)c3ccccc23)c(F)n1]

I-5
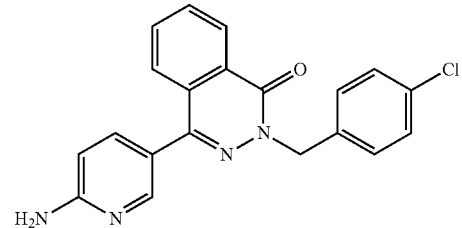 [SMILES: Nc1ccc(-c2nn(Cc3ccc(Cl)cc3)c(=O)c3ccccc23)cn1]

-continued

I-6

I-7

I-8

I-9

I-10

I-11

I-12

I-13

I-14

I-15

I-16

I-17

I-18
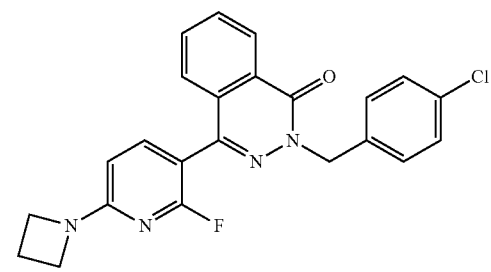
I-19
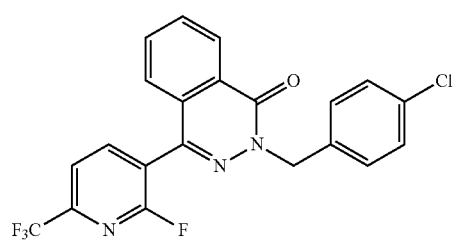
I-20
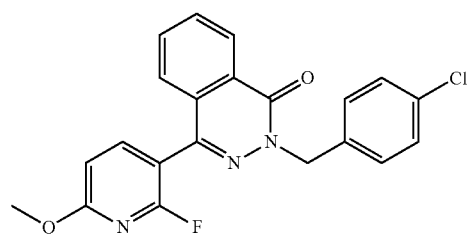
I-21
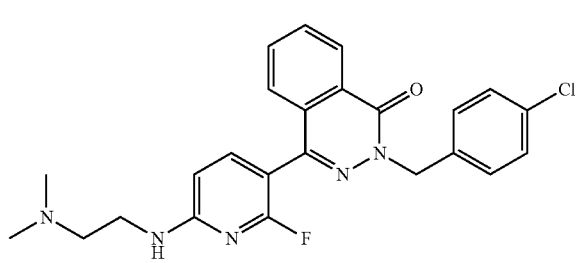
I-22
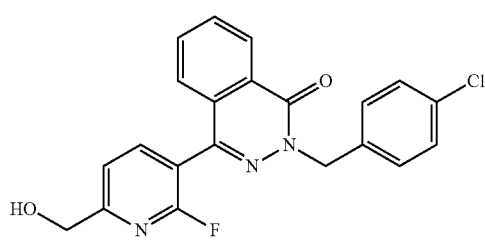
I-23
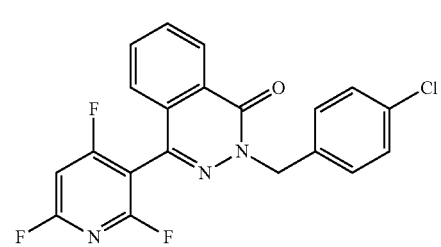
I-24
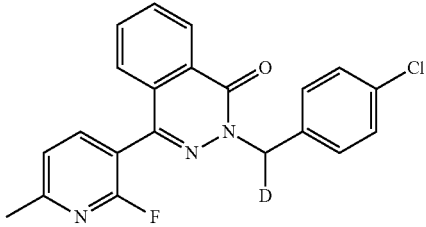
I-25
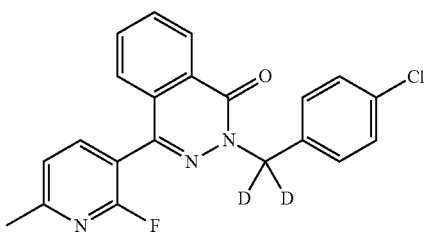
I-26
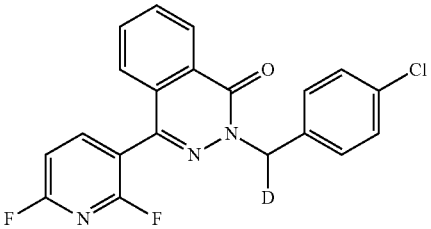
I-27
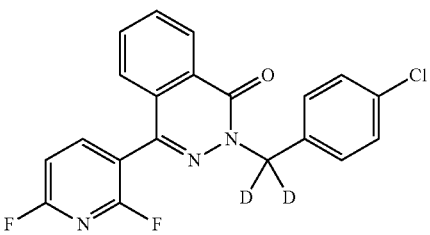
I-28
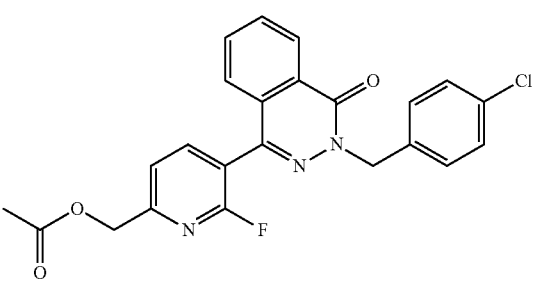
I-29
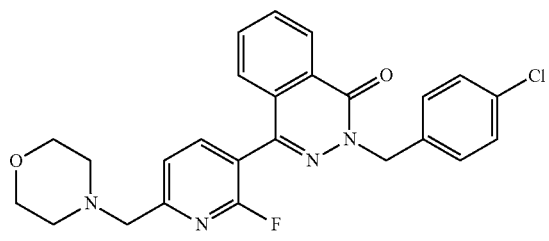

I-30
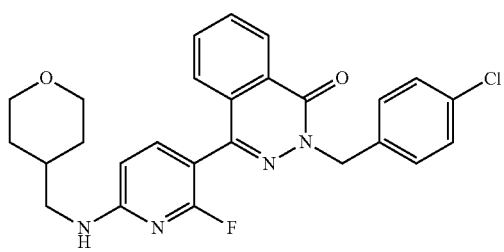
I-31
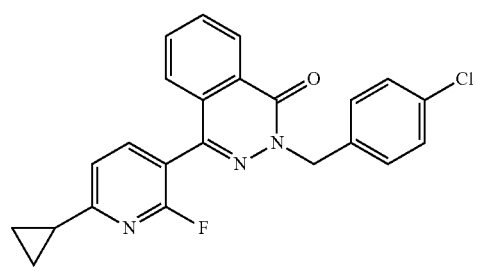
I-32
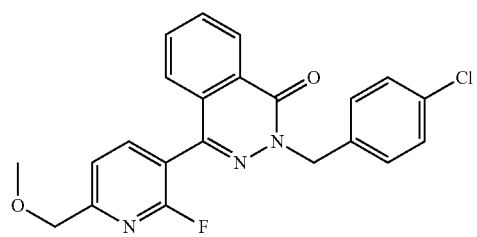
I-33
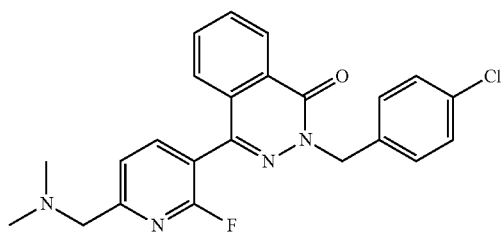
I-34
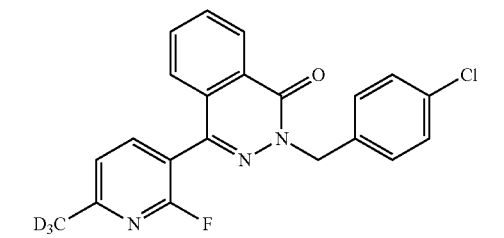
I-35
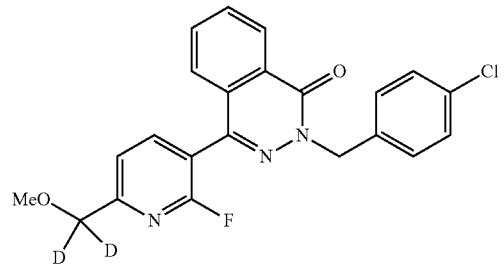
I-36
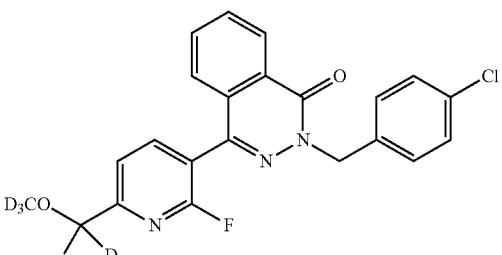
I-37
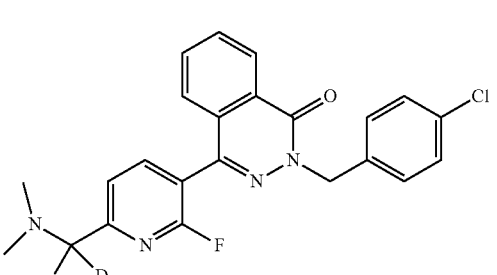
I-38
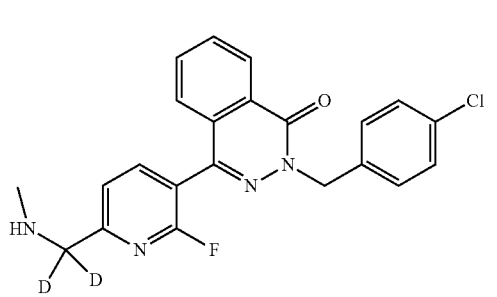
I-39
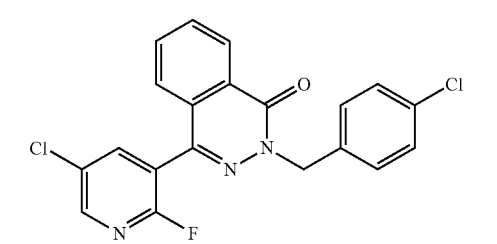
I-40
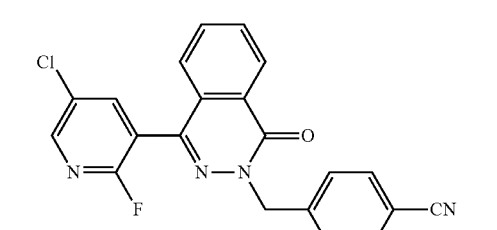
I-41
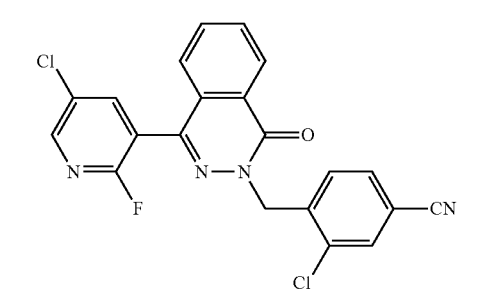

-continued
I-42
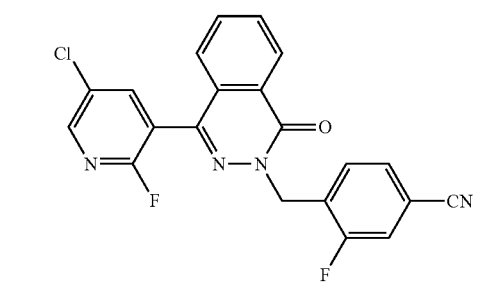
I-43
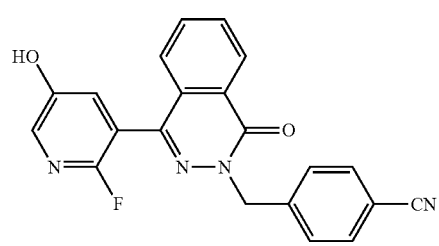
I-44
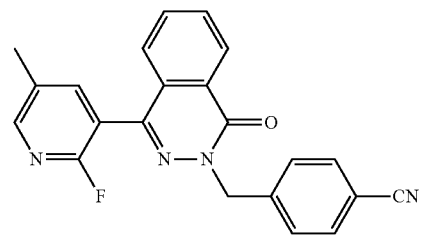
I-45
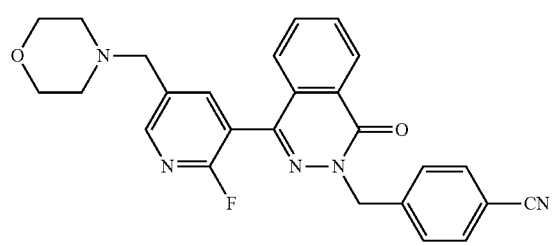
II-1
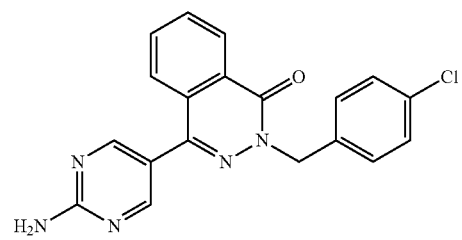
II-2
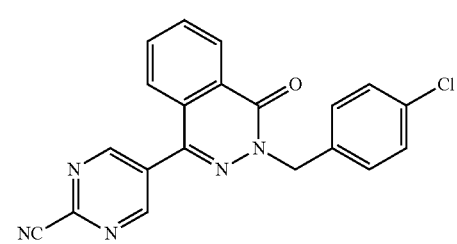
-continued
II-3
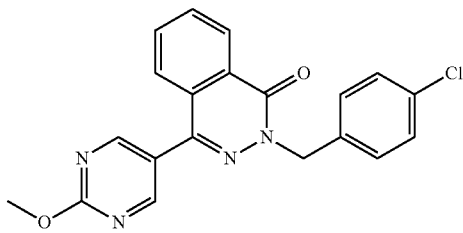
II-4
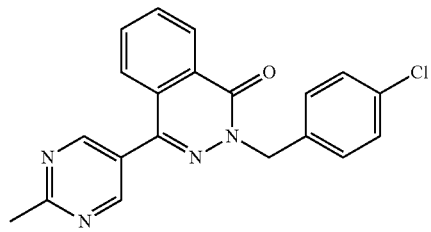
III-1
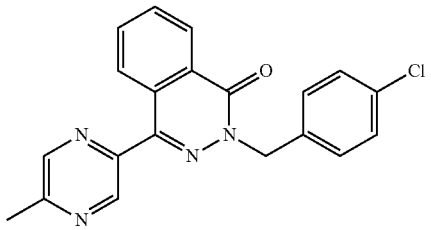
IV-1
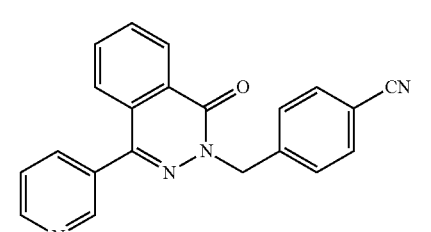
IV-2
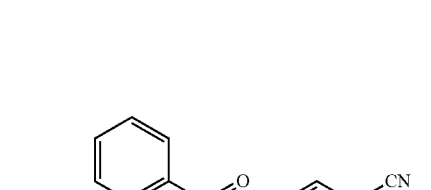
IV-3
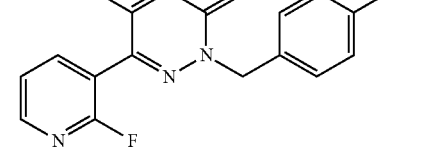

IV-4
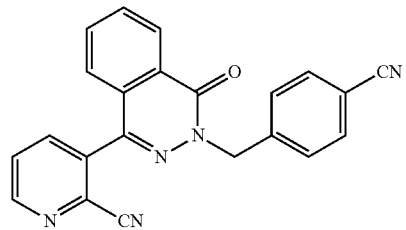
IV-5
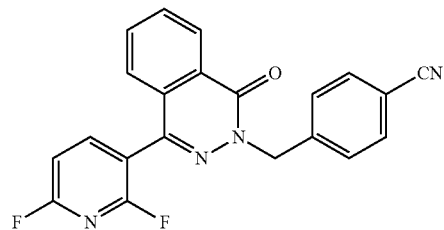
IV-6
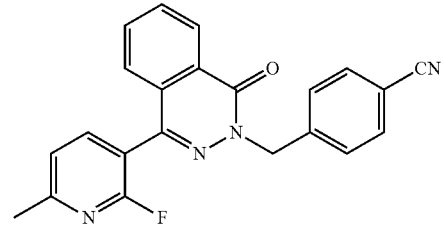
IV-7
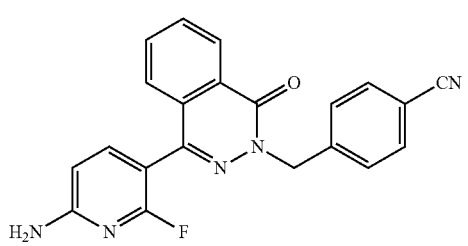
IV-8
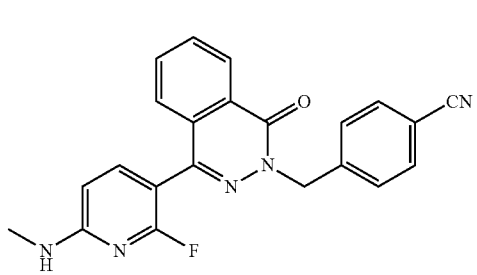
IV-9
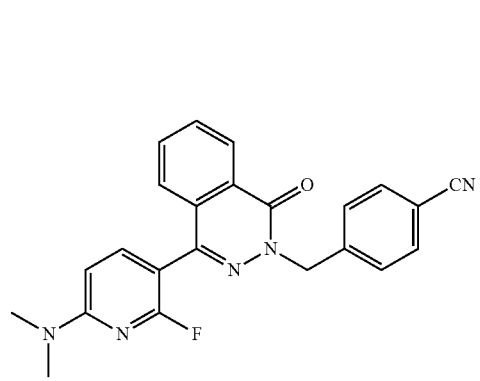
IV-10
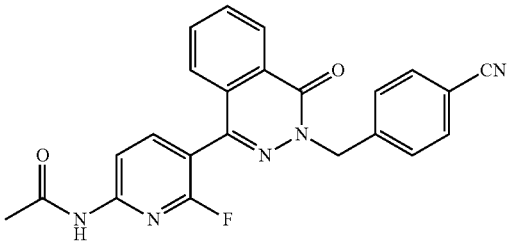
IV-11
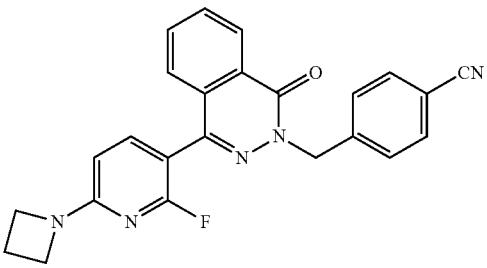
IV-12
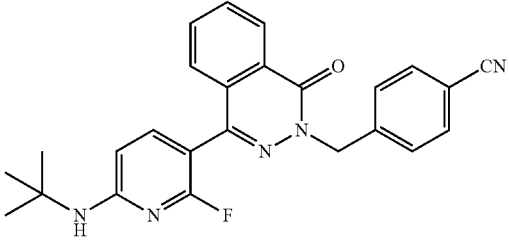
IV-13
IV-14
IV-15
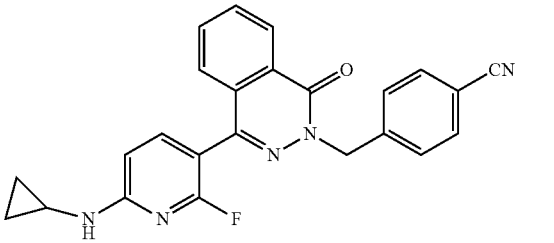

-continued
IV-16
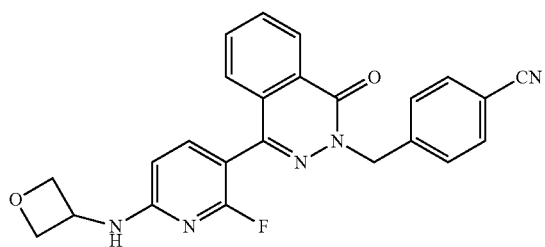
IV-17
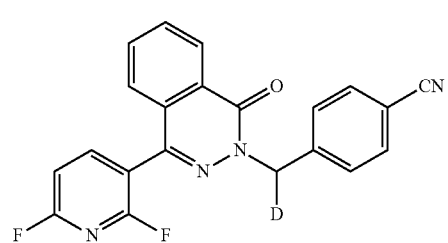
IV-18
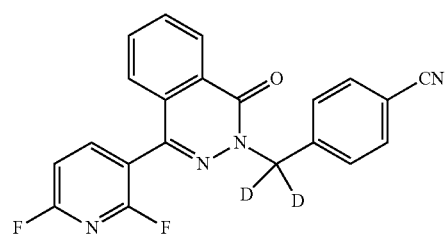
IV-19
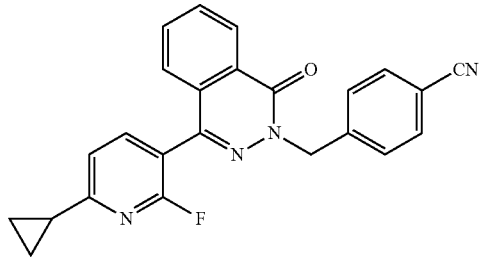
IV-20
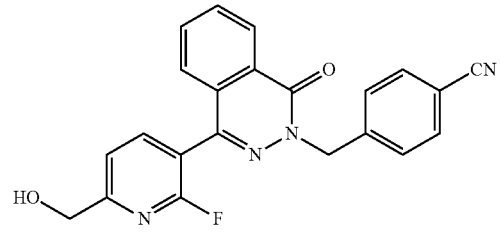
IV-21
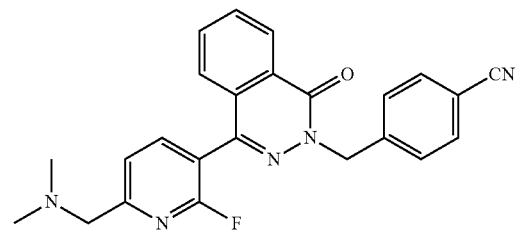
-continued
IV-22
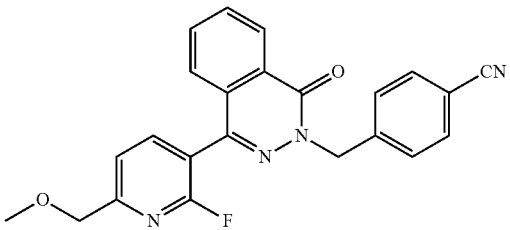
IV-23
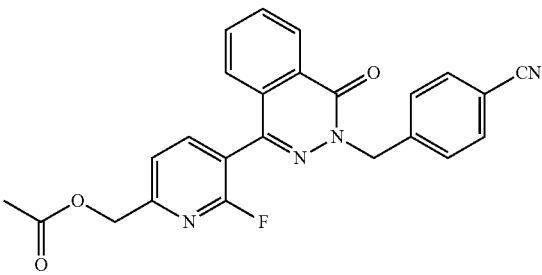
IV-24
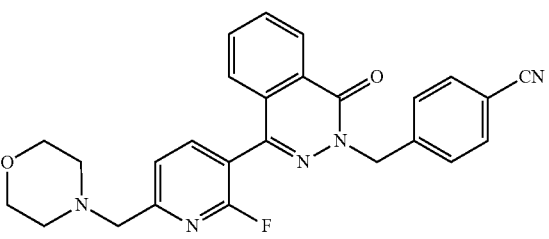
IV-25
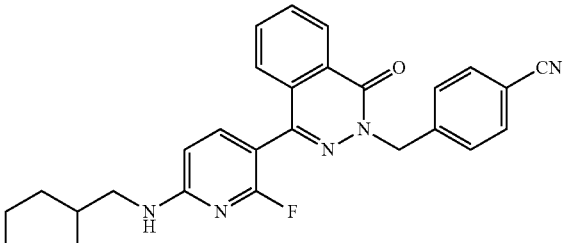
IV-26
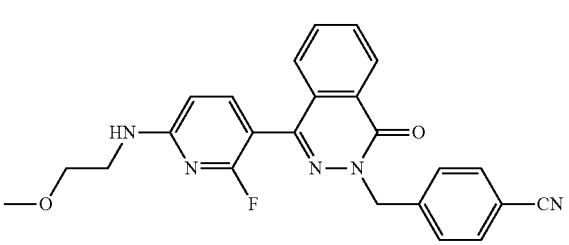
IV-27
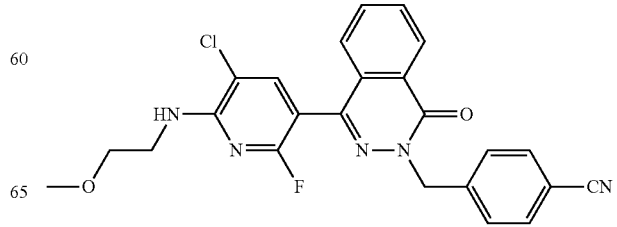

-continued
IV-28
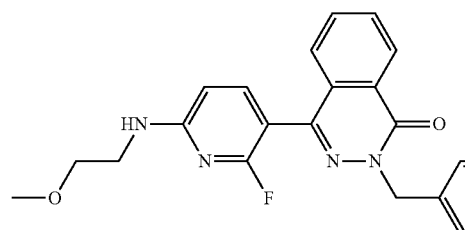
IV-29
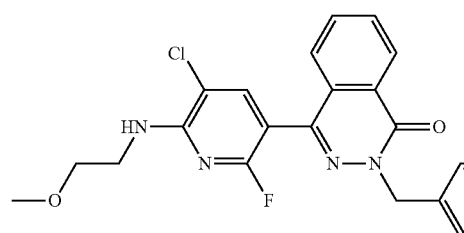
IV-30
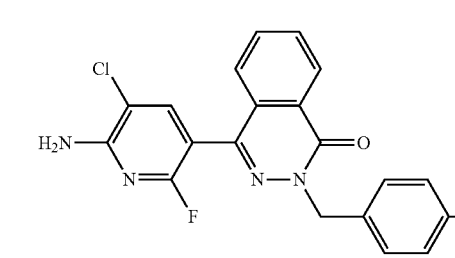
IV-31
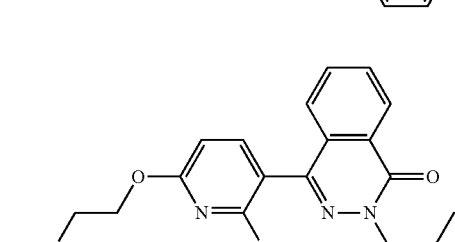
IV-32
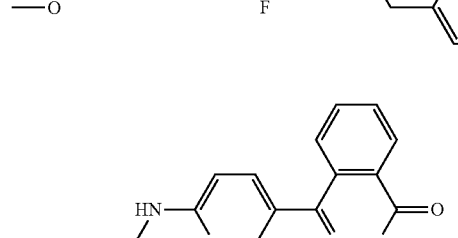
IV-33
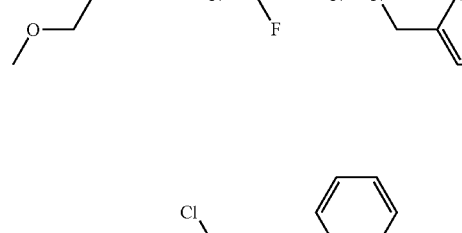
-continued
IV-34
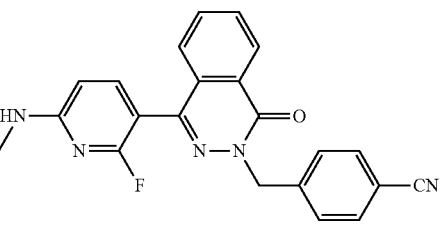
IV-35
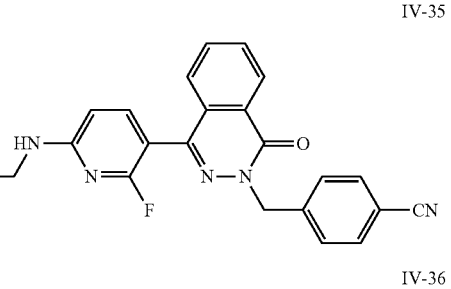
IV-36
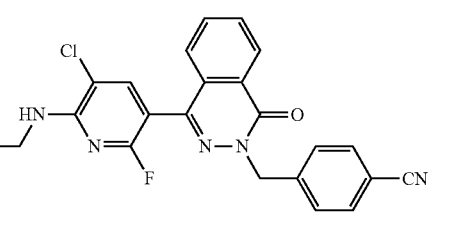
IV-37
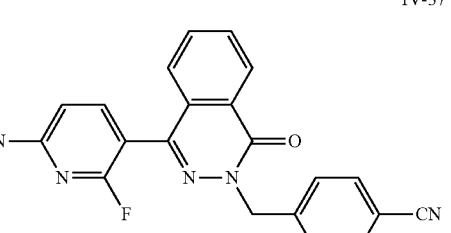
IV-38
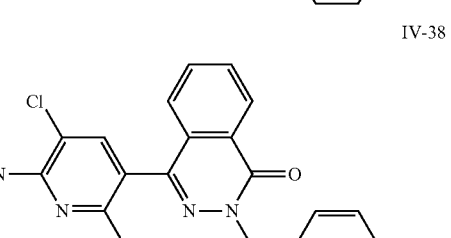
IV-39
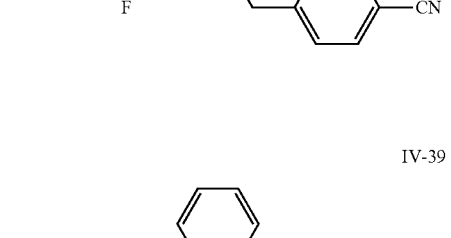

IV-40
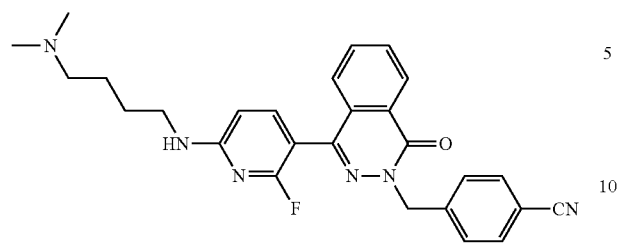
IV-41
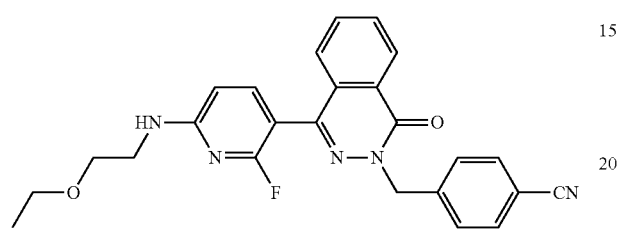
IV-42
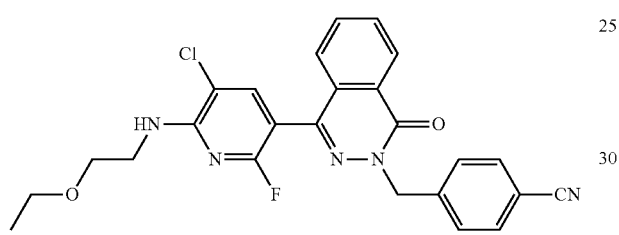
IV-43
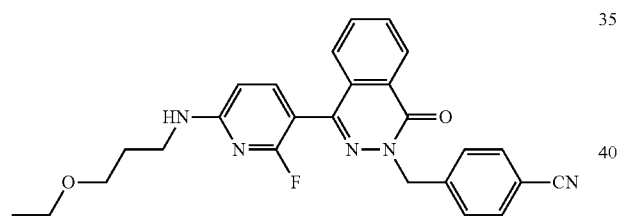
IV-44
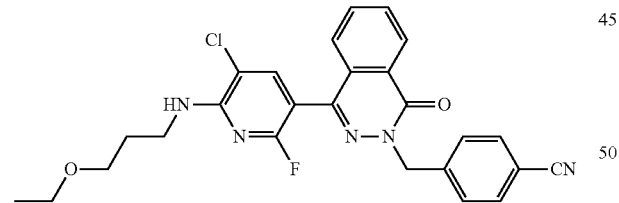
IV-45
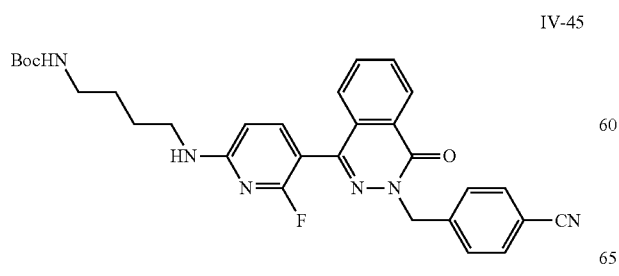
IV-46
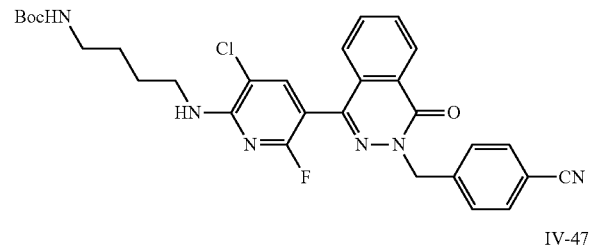
IV-47
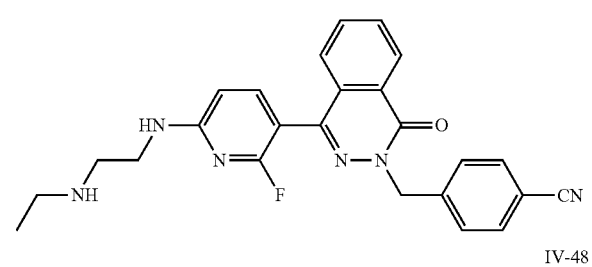
IV-48
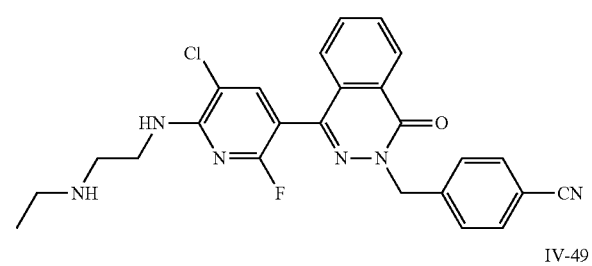
IV-49
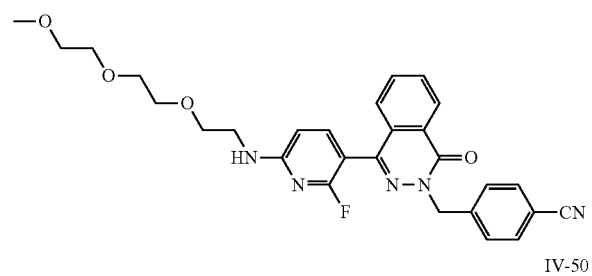
IV-50
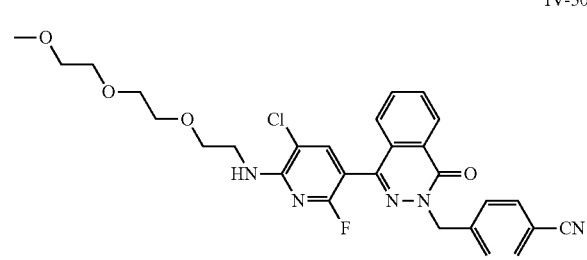
IV-51
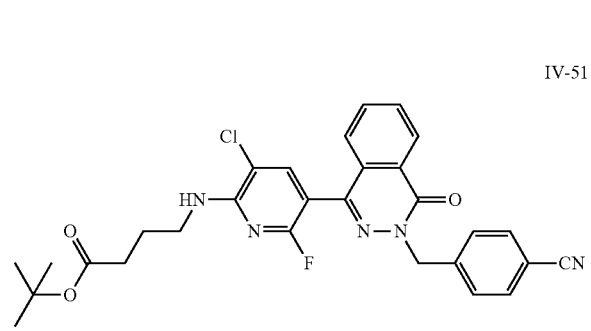

IV-52
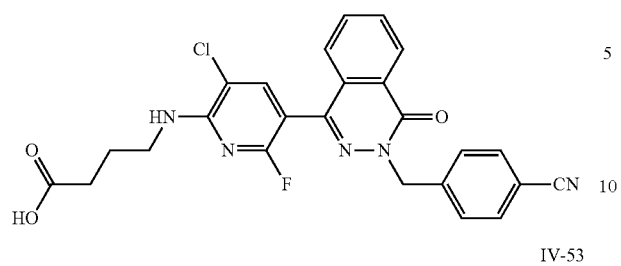
IV-53
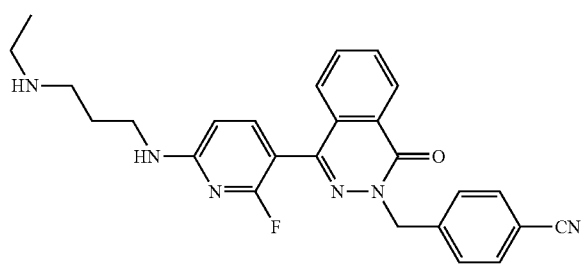
IV-54
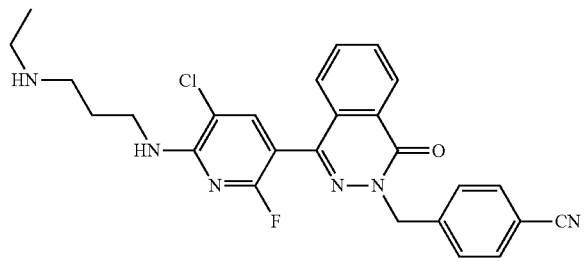
IV-55
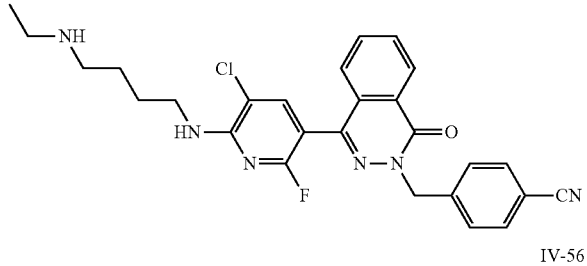
IV-56
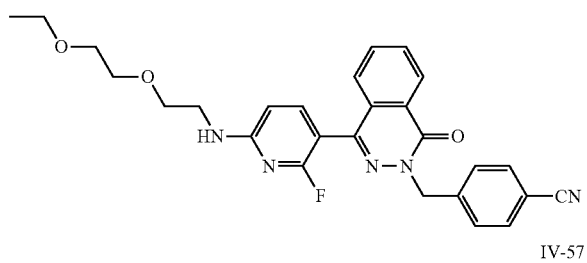
IV-57
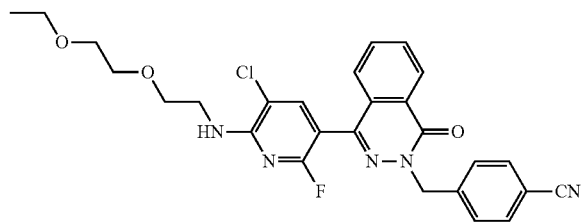
IV-58
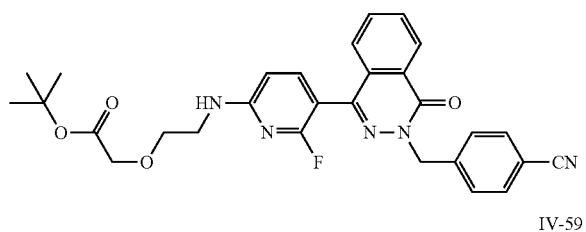
IV-59
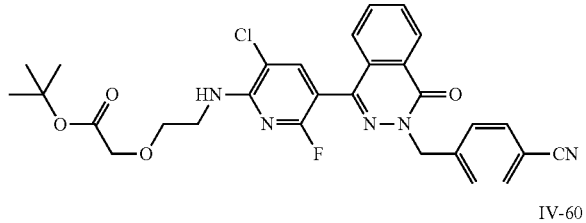
IV-60
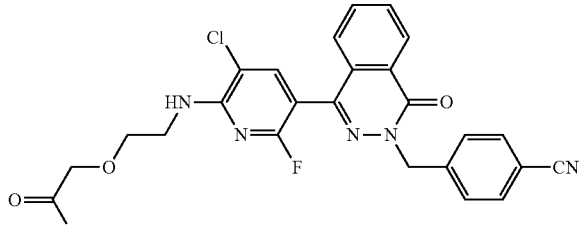
IV-61
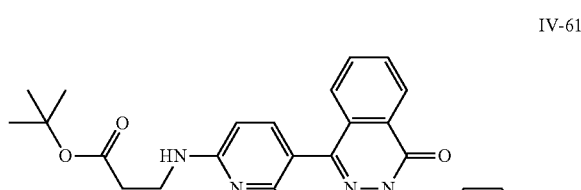
IV-62
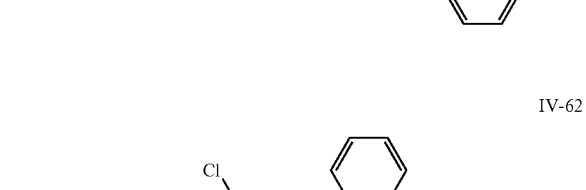
IV-63
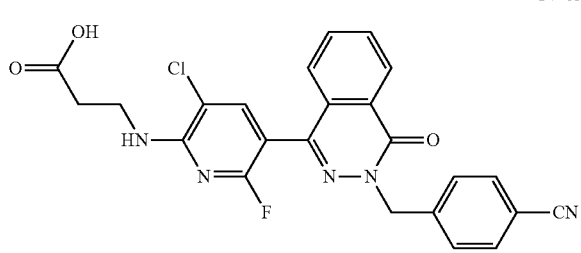

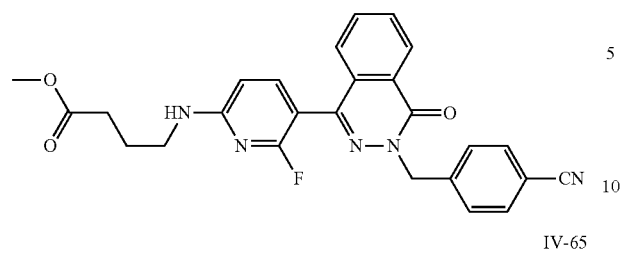

IV-76
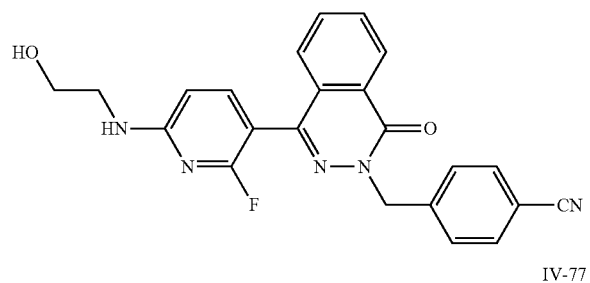
IV-77
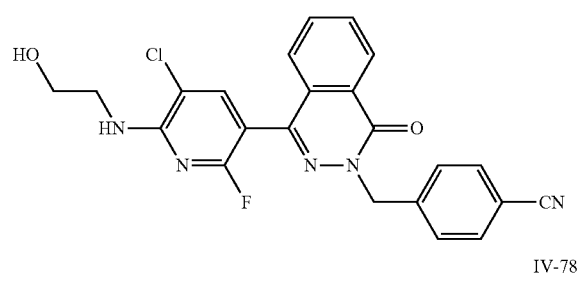
IV-78
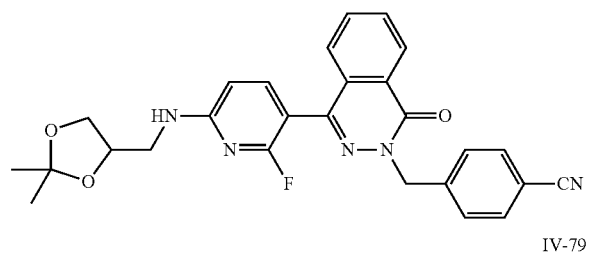
IV-79
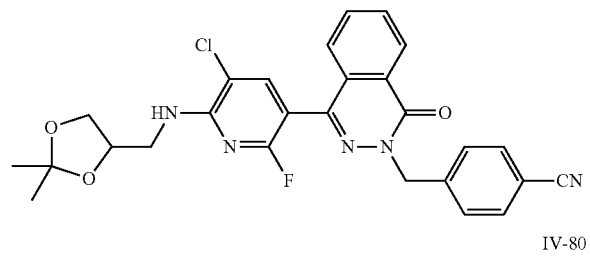
IV-80
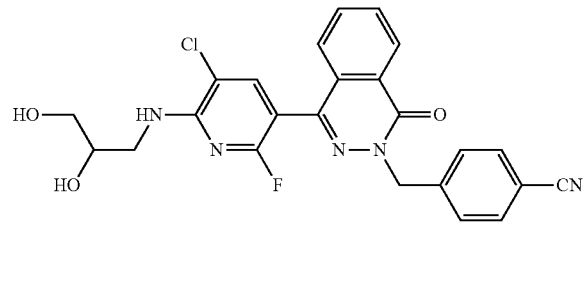
IV-81
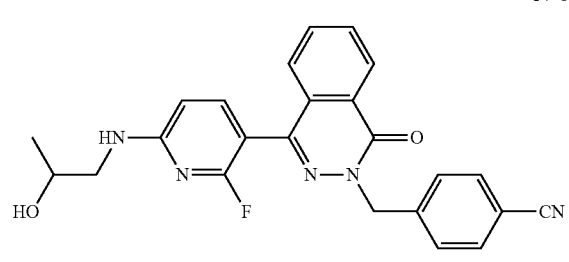
IV-82
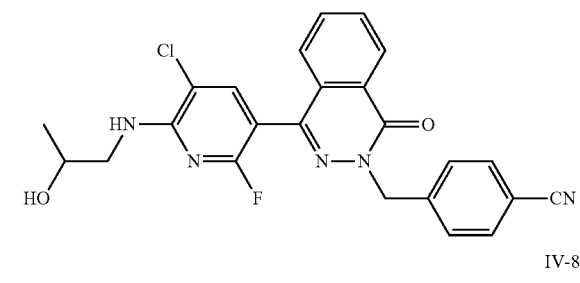
IV-83
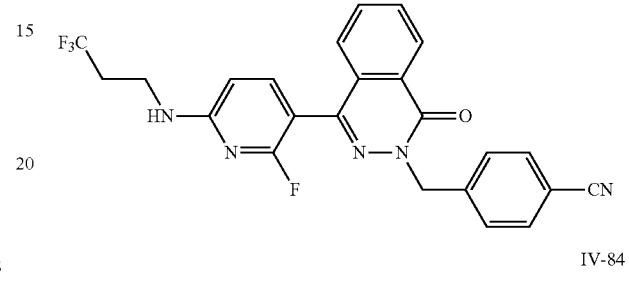
IV-84
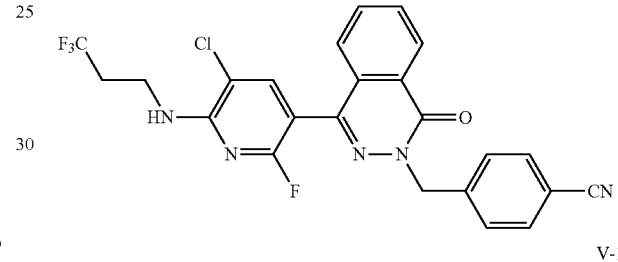
V-1
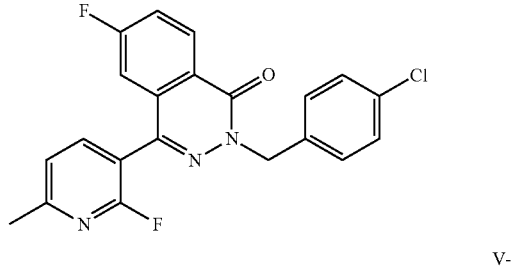
V-2
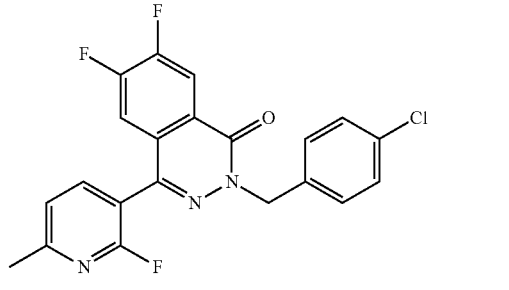
V-3
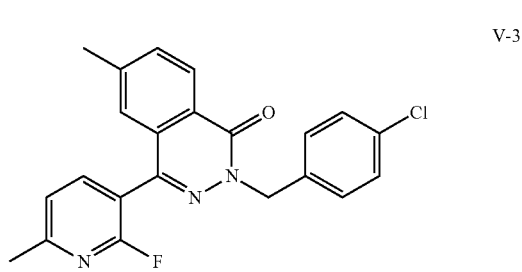

V-4

V-5

V-6

V-7

V-8

V-9

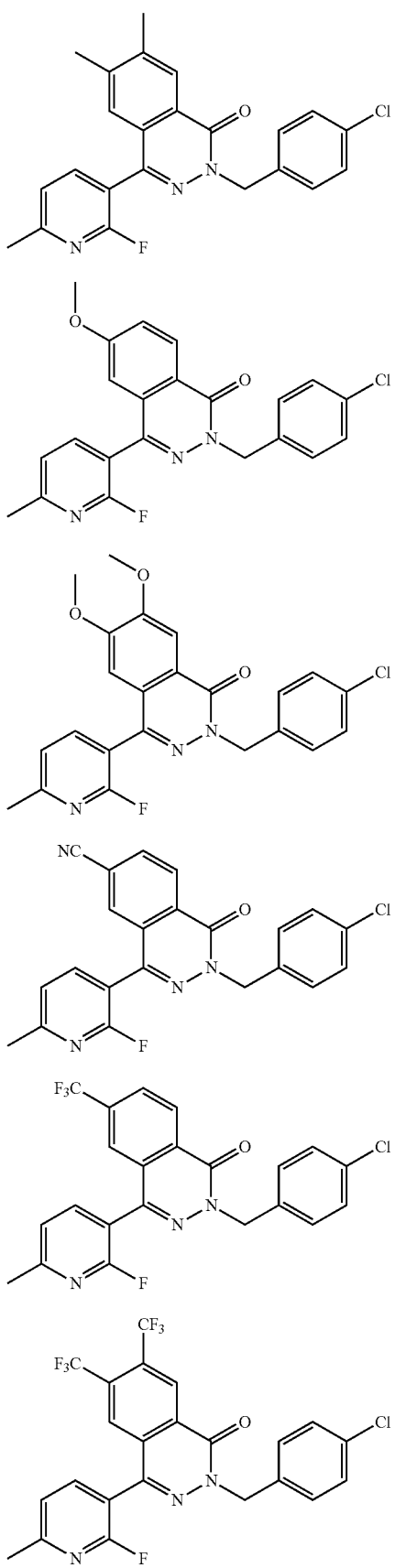

V-10

V-11

V-12

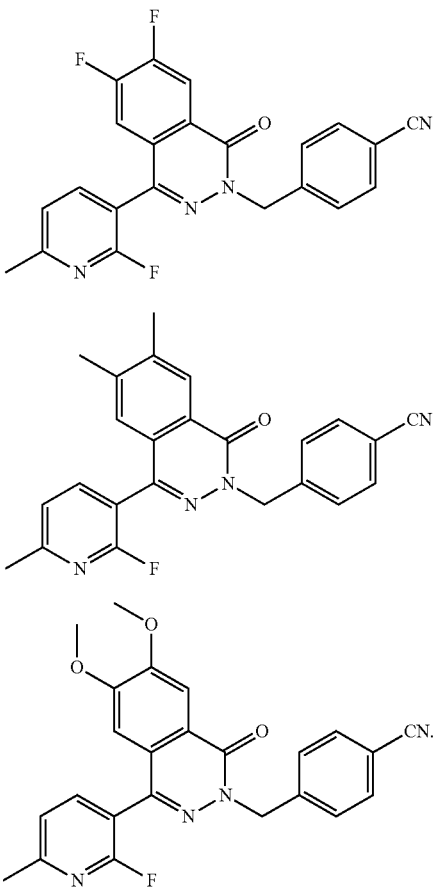

The present invention also provides a method for preparing the above-mentioned compound of formula I or a pharmaceutically acceptable salt, solvate or prodrug thereof, characterized in that the method for preparing the compound of formula I includes steps of one of the following routes:

Route 1:

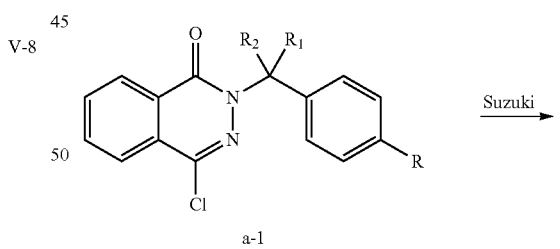

a-1

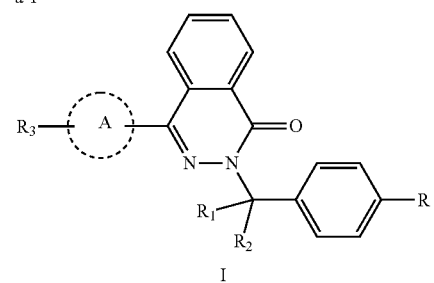

I the compound I is obtained from the compound a-1 by a Suzuki reaction, wherein, R, $R_1$, $R_2$, $R_3$, $R_4$ and A are each defined as above;

Route 2:

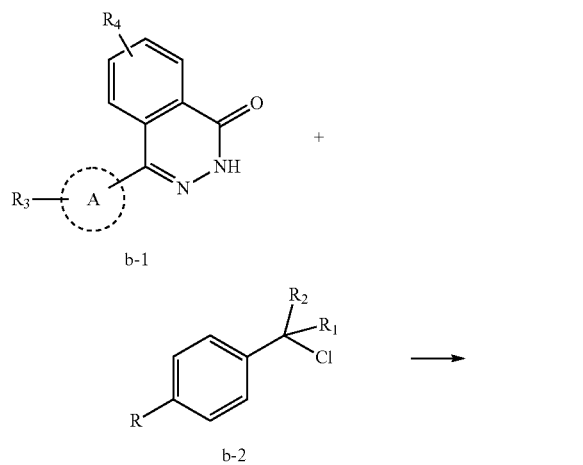

the compound I is obtained from the compound b-1 and the compound b-2 by a nucleophilic substitution, wherein, R, $R_1$, $R_2$, $R_3$, $R_4$ and A are each defined as above.

Optionally, the above preparation method includes steps of one of the following routes:

Route 1:

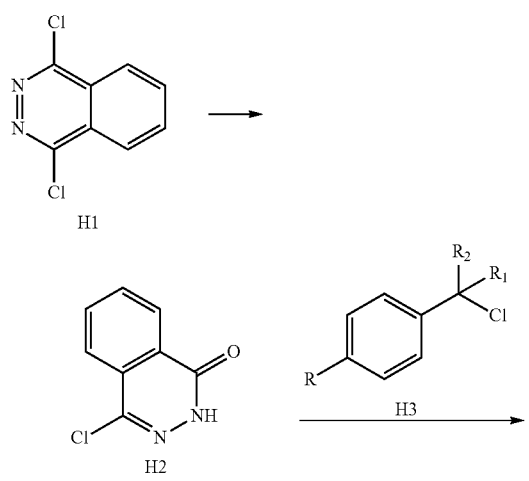

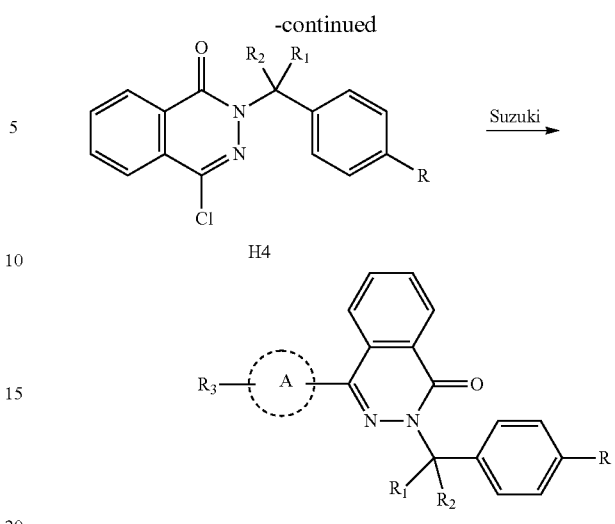

the compound represented by formula H1 is hydrolyzed to obtain the compound represented by formula H2, the compound represented by formula H2 is subjected to a nucleophilic substitution with parachlorobenzyl chloride H3 to obtain the compound represented by formula H4, which is finally subjected to a Suzuki coupling reaction under the action of a metal catalyst or a base, to obtain a phthalazinone compound represented by formula H5;

wherein, $R_4$ is H, and R, $R_1$, $R_2$, $R_3$, and A are each defined the same as the above;

Route 2:

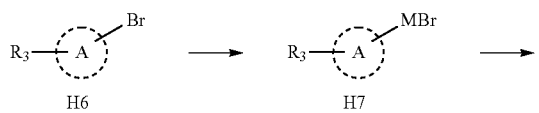

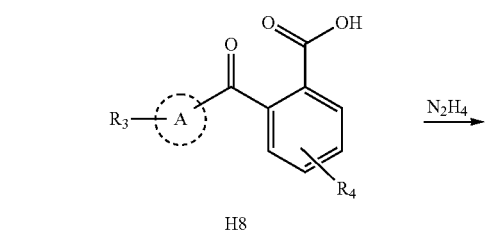

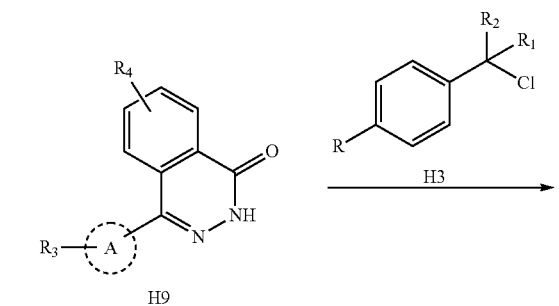

-continued

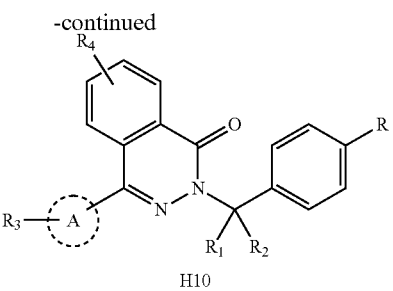

H10 the compound represented by formula H6 is prepared into the Grignard reagent represented by formula H7, which is then subjected to an addition reaction with phthalic anhydride to give the compound represented by formula H8, the compound represented by formula H8 is subjected to a ring-closing reaction with hydrazine hydrate to give the compound represented by formula H9, which is subjected to a nucleophilic substitution with parachlorobenzyl chloride to give the compound represented by formula H10;

wherein R, $R_1$, $R_2$, $R_3$ and $R_4$ are each defined as above, but $R_4$ is not H.

Preferably, in the above method, the hydrolysis is performed in a solvent under an acidic or basic condition; the acid is one or more selected from the group consisting of acetic acid, hydrochloric acid, sulfuric acid, and trifluoroacetic acid; the base is one or more selected from the group consisting of potassium hydroxide, sodium hydroxide, potassium acetate, sodium acetate, potassium t-butoxide, and sodium t-butoxide; the solvent is one or more selected from the group consisting of ethanol, methanol, water, and acetic acid.

Preferably, in the above method, the nucleophilic substitution is performed in a solvent in the presence of a base; the base is preferably one or more selected from the group consisting of potassium carbonate, cesium carbonate, sodium hydride, potassium hydride, potassium t-butoxide, sodium t-butoxide and sodium hydroxide; the solvent is preferably one or more selected from the group consisting of acetonitrile, N,N-dimethylformamide and tetrahydrofuran.

Preferably, in the above method, the Suzuki coupling reaction is performed in a solvent in the presence of a metal catalyst, a base and a ligand under a heating condition; the solvent is preferably N,N-dimethylformamide, toluene or 1,4-dioxane, the heating condition is heating under reflux or heating with microwave; the base is preferably one or more selected from the group consisting of cesium carbonate, potassium carbonate, potassium t-butoxide and sodium t-butoxide; the metal catalyst is preferably one or more selected from the group consisting of palladium acetate, $Pd(PPh_3)_4$ and $Pd(dppf)_2Cl_2$; the ligand is preferably one or more selected from the group consisting of triphenyl phosphine, 1,1'-bis(diphenylphosphine)ferrocene, binaphthalene diphenylphosphine, 2-dicyclohexylphosphino-2',6'-dimethoxy-biphenyl and 2-dicyclohexylphosphino-2'-(N,N-dimethylamino)-biphenyl.

Preferably, in the above method, the Grignard reagent prepared above may be a magnesium, iron, copper, zinc or lithium salt.

The pharmaceutically acceptable salt of the compound of formula I can be prepared by dissolving the compound of formula I in an alcohol solution saturated with a corresponding acid, for example, by dissolving a phthalazinone compound of formula I in HCl saturated methanol solution, stirring at room temperature for 30 minutes, and evaporating the solvent to dryness to obtain the corresponding hydrochloride of the compound of formula I.

The present invention further provides a pharmaceutical composition which comprises a therapeutically effective amount of one or more of the above compound of formula I or a pharmaceutically acceptable salt, solvate or prodrug thereof, and optionally, a pharmaceutically acceptable carrier.

The above pharmaceutically acceptable carrier refers to a conventional pharmaceutical carrier in the field of pharmacy, for example, a diluent such as water, etc.; a filler such as starch, sucrose etc.; a binders such as a cellulose derivative, an alginate, gelatin, polyvinylpyrrolidone; a wetting agent such as glycerol; a disintegrating agent such as agar, calcium carbonate and sodium bicarbonate; a absorption enhancer such as a quaternary ammonium compound; a surfactant such as cetyl alcohol; an adsorption carrier such as kaolin and soap clay; a lubricant such as talc, calcium stearate and magnesium stearate, and polyethylene glycol. In addition, other adjuvants, such as a flavoring agent and a sweetening agent, can also be added to the above pharmaceutical composition.

The above compound of formula I or a pharmaceutically acceptable salt, solvate or prodrug thereof, or the pharmaceutical composition can be administered to a patient in need of such treatment by oral, rectal or parenteral administration. When used for oral administration, it can be made into a conventional solid preparation, such as tablets, powders, granules, capsules, etc., or into a liquid preparation, such as water or oil suspensions, or other liquid preparations, such as syrup; when used for parenteral administration, it can be made into a solution, a water or oily suspension for injection, and the like.

The present invention also provides use of the compound of formula I or a pharmaceutically acceptable salt, solvate or prodrug thereof, or the pharmaceutical composition described above in preparation of a medicament for prevention and/or treatment of hepatitis B disease.

The present invention also provides use of the compound of formula I or a pharmaceutically acceptable salt, solvate or prodrug thereof, or the pharmaceutical composition described above in preparation of a HBV inhibitor.

The present invention also provides use of the compound of formula I or a pharmaceutically acceptable salt, solvate or prodrug thereof, or the pharmaceutical composition described above in preparation of a medicament for inhibiting virus replication, said virus includes hepatitis A virus, HBV, hepatitis C virus, influenza virus, adenovirus, HIV, herpes virus, human papilloma virus.

The present invention also provides a method for preventing and/or treating hepatitis B disease, comprising administering an effective amount of the compound of formula I or a pharmaceutically acceptable salt, solvate or prodrug thereof, or the pharmaceutical composition described above.

The present invention also provides a method for inhibiting HBV, comprising administering an effective amount of the compound of formula I or a pharmaceutically acceptable salt, solvate or prodrug thereof, or the pharmaceutical composition described above.

The present invention also provides a method for inhibiting virus replication, comprising administering an effective amount of the compound of formula I or a pharmaceutically acceptable salt, solvate or prodrug thereof, or the pharmaceutical composition described above. The virus includes hepatitis A virus, HBV, hepatitis C virus, influenza virus, adenovirus, HIV, herpes virus, human papilloma virus.

According to a specific embodiment in one aspect, the compound exerts antiviral activity by interfering with the nucleocapsidization of the viral RNA, has a highly effective activity of inhibiting HBV DNA replication at the cellular level, and has less growth toxicity to HepG2.2.15 cells.

According to a specific embodiment in one aspect, the compound has good liver targeting, can stably exist and enrich in the liver, and is an effective HBV inhibitor.

BRIEF DESCRIPTION OF THE DRAWINGS

FIG. 1 shows images of the non-denaturing agarose gel electrophoresis of test example 2.

DETAILED DESCRIPTION

Hereinafter, examples of the present invention will be described in detail. It should be understood that the examples described herein are only used to illustrate the present invention, and they are not intended to limit the present invention.

In the following examples, the nuclear magnetic resonance proton spectrum was recorded on a Bruker AMX-400, Gemini-300, or AMX-600 nuclear magnetic resonance spectrometer, and the unit of chemical shift δ is ppm. The specific optical rotation was measured on a Perkin-Elmer 241 automatic polarimeter, and the microwave treatment was carried out on a CEM-discovery microwave reactor. Silica gel (200-300 mesh) for column chromatography was produced by Qingdao Ocean Chemical Branch Plant. Thin layer chromatography was carried out on a GF254 high-performance plate produced by Yantai Chemical Research Institute. Preparative thin-layer chromatography plates were produced by the Shanghai Institute of Materia Medica, Chinese Academy of Sciences, and the stationary phase was prepared by using GF254 (HG/T2354-92) silica gel and sodium carboxymethyl cellulose (800-1200), which were produced by Qingdao Ocean Chemical Co., Ltd. and China National Medicine Group Shanghai Chemical Reagent Company, respectively. Unless otherwise specified, all solvents were analytically pure. All reagents were purchased from Sinopharm Chemical Reagent Co., Ltd. Color developing was performed by using iodine, ultraviolet fluorescence and the like. The organic solvent was distilled off in a rotary evaporator under reduced pressure.

Example 1

The scheme for synthesizing compound I-1 is shown as below:

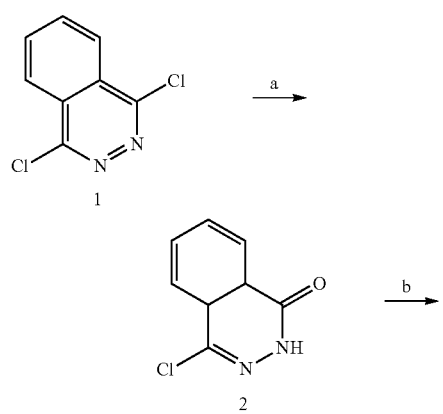

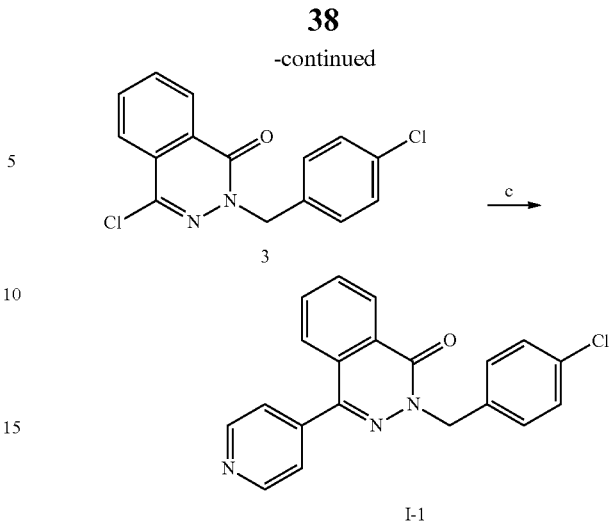

Step a:

3,6-dichlorophthalazine (10 g, 50.3 mmol) was dissolved in acetic acid (150 ml) and refluxed at 120° C. for 6 hours. After the reaction was completed as monitored by TLC, the reaction was terminated and the reaction solution was cooled to room temperature. A white solid 2 (8.5 g, 94%) was obtained after removing acetic acid by rotary evaporation under reduced pressure.

Step b:

Phthalazinone 2 (1.0 g, 5.5 mmol) was dissolved in DMF (70 ml), and p-chlorobenzyl chloride (1.1 g, 6.6 mmol) and $Cs_2CO_3$ (2.1 g, 6.6 mmol) were added in this order. After the reaction system was stirred at 50° C. for 5 hours, the reaction was completed as monitored by TLC. Ethyl acetate (100 ml) and water (100 ml) were added to the reaction solution, and the organic layer was washed with water (100 ml×4) and saturated brine (100 ml) in this order, dried over anhydrous sodium sulfate for half an hour and concentrated to obtain a crude product. The crude product was separated and purified by column chromatography (PE:EA=100:0~10:1) to obtain a white solid 3 (1.5 g, 88%). $^1$H NMR (400 MHz, $CDCl_3$) δ 8.49-8.44 (m, 1H), 8.02-7.99 (m, 1H), 7.88 (dtd, J=16.4, 7.3, 1.4 Hz, 2H), 7.50-7.43 (m, 2H), 7.34-7.30 (m, 2H), 5.34 (s, 2H). MS (ESI): 305.1 [M+H]$^+$.

Step c:

Compound 3 (100 mg, 0.33 mmol) was dissolved in a mixed solvent of 1,4-dioxane (20 ml) and water (5 ml), and then pyridine-4-boronic acid (52.9 mg, 0.43 mmol), Pd(PPh$_3$)$_4$ (76.0 mg, 0.033 mmol) and $K_3PO_4$ (139 mg, 0.66 mmol) were added in this order. After purged with $N_2$ for three times, the reaction was performed at 100° C. overnight. After the reaction was completed as monitored by TLC at the next day, the reaction system was cooled to room temperature. After removing the solvent by rotary evaporation under reduced pressure, the residue was extracted and dissolved with ethyl acetate (30 ml). The organic layer was washed with water (30 ml×3) and saturated brine (30 ml) in this order, dried over anhydrous sodium sulfate, and concentrated to give a crude product. The crude product was separated and purified by column chromatography to obtain product I-1 (92 mg, 81%). $^1$H NMR (400 MHz, $CDCl_3$) δ 8.69 (dd, J=4.5, 1.7 Hz, 2H), 7.66 (dd, J=4.5, 1.7 Hz, 2H), 7.58 (dt, J=8.1, 2.0 Hz, 1H), 7.44-7.40 (m, 2H), 7.34 (d, J=1.3 Hz, 1H), 7.46-7.40 (m, 2H), 7.33-7.27 (m, 2H), 5.36 (s, 2H).

The following compounds were prepared in the same method as that in Example 1:

| Compounds | Preparation methods and structures of the products |
|---|---|
| I-2 | 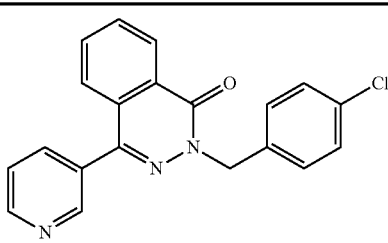

Compound I-2 was prepared in the same method as that in Example 1, except that pyridine-3-boric acid was used in place of pyridine-4-boronic acid. (White crystal, yield 77%)
$^1$H NMR (400 MHz, CDCl$_3$) δ 8.88 (d, J = 2.2 Hz, 1H), 8.79 (dd, J = 4.9, 1.6 Hz, 1H), 8.60-8.55 (m, 1H), 7.94 (dt, J = 8.1, 2.0 Hz, 1H), 7.87-7.79 (m, 2H), 7.73-7.69 (m, 1H), 7.53-7.47 (m, 3H), 7.35-7.31 (m, 2H), 5.46 (s, 2H), 1.62 (s, 3H). |
| I-3 | 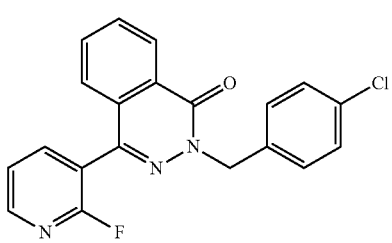 [SMILES: O=c1c2ccccc2c(-c2cccnc2Cl)nn1Cc1ccc(Cl)cc1]

Compound I-3 was prepared in the same method as that in Example 1, except that 2-fluoro-pyridine-3-boronic acid was used in place of pyridine-4-boronic acid. (White crystal, yield 62%)
$^1$H NMR (400 MHz, CDCl$_3$) δ 8.56-8.51 (m, 1H), 8.45-8.41 (m, 1H), 7.96 (ddd, J = 9.3, 7.4, 2.0 Hz, 1H), 7.81 (pd, J = 7.2, 1.4 Hz, 2H), 7.49-7.40 (m, 4H), 7.35-7.30 (m, 2H), 5.43 (s, 2H). |
| I-4 | 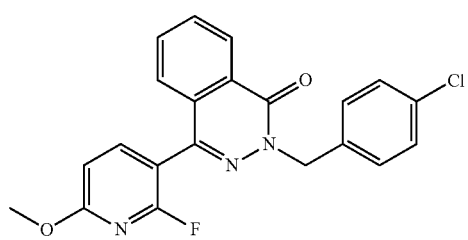

Compound I-4 was prepared in the same method as that in Example 1, except that 2-fluoro-6-methoxy-pyridine-3-boronic acid was used in place of pyridine-4-boronic acid. (White crystal, yield 70%)
$^1$H NMR (300 MHz, CDCl$_3$) δ 8.53 (s, 1H), 7.99 (d, J = 9.0 Hz, 1H), 7.74 (dt, J = 8.1, 2.0 Hz, 1H), 7.55-7.52 (m, 2H), 7.44 (d, J = 8.8 Hz, 2H), 7.29 (d, J = 8.3 Hz, 2H), 6.82 (d, J = 8.6 Hz, 1H), 5.33 (s, 2H), 3.98 (s, 3H). |
| I-5 | 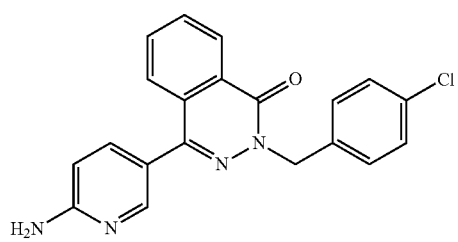

Compound I-5 was prepared in the same method as that in Example 1, except that 6-amino-pyridine-3-boronic acid was used in place of pyridine-4-boronic acid. (White crystal, yield 74%)
$^1$H NMR (300 MHz, CDCl$_3$) δ 8.45 (s, 1H), 7.89 (s, 1H), 7.82 (ddd, J = 9.3, 7.4, 2.0 Hz, 1H), 7.77-7.73 (d, J = 7.2, 1.4 Hz, 2H), 7.66 (d, J = 1.3 Hz, 1H), 7.43 (d, J = 6.4 Hz, 2H), 7.32 (d, J = 7.4 Hz, 2H), 6.56 (d, J = 8.4 Hz, 1H), 5.35 (d, J = 14.5 Hz, 2H), 4.66 (s, 2H). |

| Compounds | Preparation methods and structures of the products |
|---|---|
| I-6 | 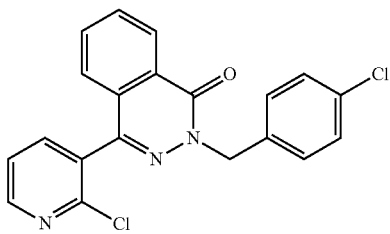
Compound I-6 was prepared in the same method as that in Example 1, except that 2-chloro-pyridine-3-boronic acid was used in place of pyridine-4-boronic acid. (White crystal, yield 31%)
$^1$H NMR (400 MHz, CDCl$_3$) δ 7.82 (dd, J = 7.6, 1.9 Hz, 1H), 7.76 (d, J = 1.2 Hz, 1H), 7.72 (ddd, J = 9.3, 7.4, 2.0 Hz, 1H), 7.63 (d, J = 7.2, 1.4 Hz, 2H), 7.41-7.37 (m, 3H), 7.36 (dd, J = 7.6, 4.8 Hz, 1H), 7.32-7.28 (m, 2H), 5.34 (s, 2H). |
| I-7 | 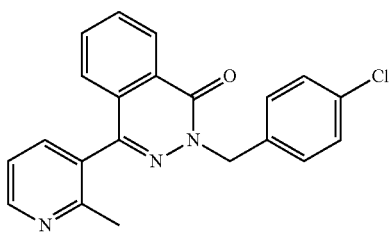 [SMILES: Cc1ncccc1-c1nn(Cc2ccc(Cl)cc2)c(=O)c2ccccc12]
Compound I-7 was prepared in the same method as that in Example 1, except that 2-methyl-pyridine-3-boronic acid was used in place of pyridine-4-boronic acid. (White crystal, yield 77%)
$^1$H NMR (500 MHz, CDCl$_3$) δ 8.84 (s, 1H), 8.26 (s, 1H), 7.84 (s, 1H), 7.65 (d, J = 5.0 Hz, 2H), 7.58 (s, 1H), 7.47-7.29 (m, 5H), 4.87 (s, 2H), 2.56 (s, 3H). |
| I-8 | 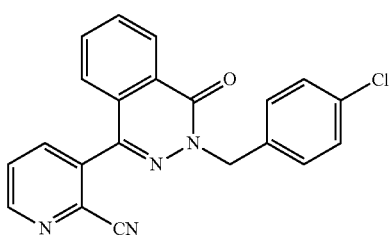 [SMILES: N#Cc1ncccc1-c1nn(Cc2ccc(Cl)cc2)c(=O)c2ccccc12]
Compound I-8 was prepared in the same method as that in Example 1, except that 2-cyano-pyridine-3-boronic acid was used in place of pyridine-4-boronic acid. (White crystal, yield 76%)
$^1$H NMR (500 MHz, CDCl$_3$) δ 8.69-8.62 (m, 2H), 8.13 (t, J = 7.5 Hz, 1H), 7.86-7.82 (m, 1H), 7.69-7.62 (m, 2H), 7.63-7.55 (m, 1H), 7.39 (d, J = 7.5 Hz, 2H), 7.32 (d, J = 7.5 Hz, 2H), 4.87 (s, 2H). |
| I-9 | 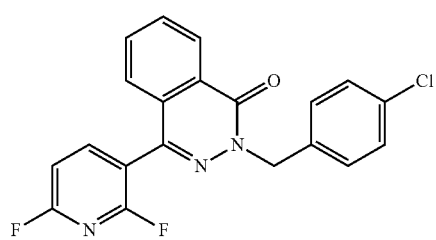 [SMILES: O=c1c2ccccc2c(-c2ccc(F)nc2F)nn1Cc1ccc(Cl)cc1]
Compound I-9 was prepared in the same method as that in Example 1, except that 2,6-difluoro-pyridine-3-boronic acid was used in place of pyridine-4-boronic acid. (White crystal, yield 83%)
$^1$H NMR (400 MHz, CDCl$_3$) δ 8.54-8.45 (m, 1H), 8.06-7.97 (m, 1H), 7.83-7.74 (m, 2H), 7.47-7.38 (m, 3H), 7.31-7.26 (m, 2H), 7.03 (dd, J = 8.0, 2.6 Hz, 1H), 5.40 (s, 2H). |

| Compounds | Preparation methods and structures of the products |
|---|---|
| I-10 | 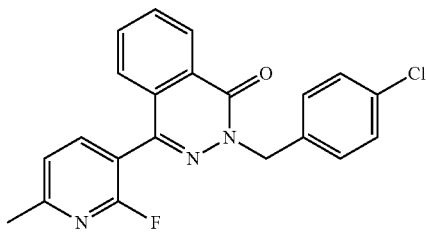 [SMILES: Cc1ccc(-c2nn(Cc3ccc(Cl)cc3)c(=O)c3ccccc23)c(F)n1]<br>Compound I-10 was prepared in the same method as that in Example 1, except that 2-fluoro-6-methyl-pyridine-3-boronic acid was used in place of pyridine-4-boronic acid. (White crystal, yield 85%)<br>$^1$H NMR (400 MHz, CDCl$_3$) δ 8.55-8.49 (m, 1H), 7.85-7.76 (m, 3H), 7.49-7.43 (m, 3H), 7.33-7.30 (m, 2H), 7.25 (dd, J = 7.6, 1.7 Hz, 1H), 5.43 (s, 2H), 2.65 (s, 3H). |
| I-11 | 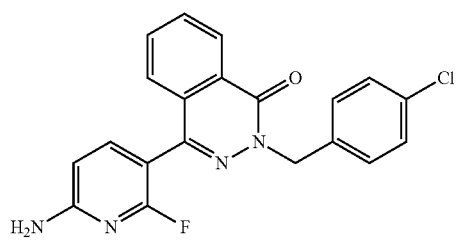<br>Compound I-11 was prepared in the same method as that in Example 1, except that 2-fluoro-6-amino-pyridine-3-boronic acid pinacol ester was used in place of pyridine-4-boronic acid. (White crystal, yield 64%)<br>$^1$H NMR (400 MHz, CD$_3$OD) δ 8.46-8.40 (m, 1H), 7.89-7.84 (m, 2H), 7.62 (dd, J = 9.7, 8.2 Hz, 2H), 7.43 (d, J = 8.5 Hz, 2H), 7.31 (d, J = 8.4 Hz, 2H), 6.55 (dd, J = 8.2, 1.8 Hz, 1H), 5.42 (s, 2H). |
| I-12 | 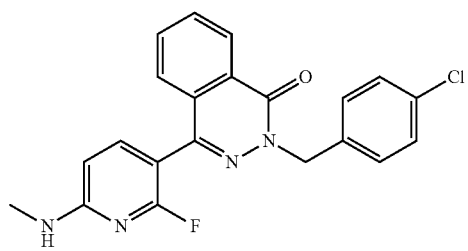 [SMILES: CNc1ccc(-c2nn(Cc3ccc(Cl)cc3)c(=O)c3ccccc23)c(F)n1]<br>Compound I-12 was prepared in the same method as that in Example 1, except that 2-fluoro-6-methylamino-pyridine-3-boronic acid pinacol ester was used in place of pyridine-4-boronic acid. (White crystal, 71% yield)<br>$^1$H NMR (400 MHz, CDCl$_3$) δ 8.54-8.43 (m, 1H), 7.78 (dt, J = 10.5, 3.5 Hz, 2H), 7.64 (dd, J = 9.5, 8.2 Hz, 1H), 7.61-7.55 (m, 1H), 7.47 (d, J = 8.6 Hz, 2H), 7.34-7.29 (m, 2H), 6.40 (dd, J = 8.2, 2.0 Hz, 1H), 5.42 (s, 2H), 4.90 (s, 1H), 3.03 (d, J = 5.2 Hz, 3H). |
| I-13 | 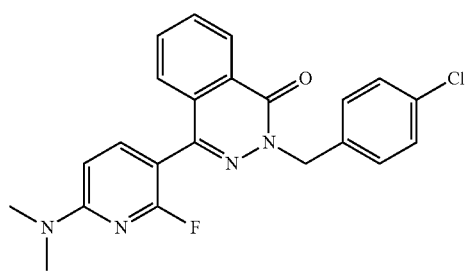 [SMILES: CN(C)c1ccc(-c2nn(Cc3ccc(Cl)cc3)c(=O)c3ccccc23)c(F)n1]<br>Compound I-13 was prepared in the same method as that in Example 1, except that 2-fluoro-6-dimethylamino-pyridine-3-boronic acid pinacol ester was used in place of pyridine-4-boronic acid. (White crystal, yield 75%)<br>$^1$H NMR (400 MHz, CDCl$_3$) δ 8.53-8.46 (m, 1H), 7.77 (dd, J = 6.5, 2.9 Hz, 2H), 7.65 (dd, J = 9.7, 8.4 Hz, 1H), 7.61-7.57 (m, 1H), 7.49-7.44 (m, 2H), 7.32-7.28 (m, 2H), 6.48 (dd, J = 8.4, 2.2 Hz, 1H), 5.42 (s, 2H), 3.18 (s, 6H). |

| Compounds | Preparation methods and structures of the products |
|---|---|
| I-14 | 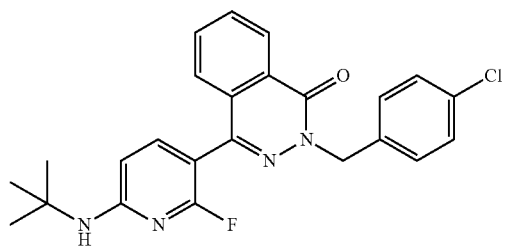 [SMILES: CC(C)(C)Nc1ccc(-c2nn(Cc3ccc(Cl)cc3)c(=O)c3ccccc23)c(F)n1]<br>Compound I-14 was prepared in the same method as that in Example 1, except that 2-fluoro-6-t-butylamino-pyridine-3-boronic acid pinacol ester was used in place of pyridine-4-boronic acid. (White crystal, yield 65%)<br>$^1$H NMR (400 MHz, CDCl$_3$) δ 8.50 (dt, J = 5.6, 3.3 Hz, 1H), 7.80-7.76 (m, 2H), 7.64-7.60 (m, 1H), 7.55 (dd, J = 29.7, 8.2 Hz, 1H), 7.48-7.44 (m, 2H), 7.32-7.29 (m, 2H), 6.40 (dd, J = 8.2, 2.0 Hz, 1H), 5.42 (s, 2H), 4.84 (s, 1H), 1.51 (s, 9H). |
| I-15 | 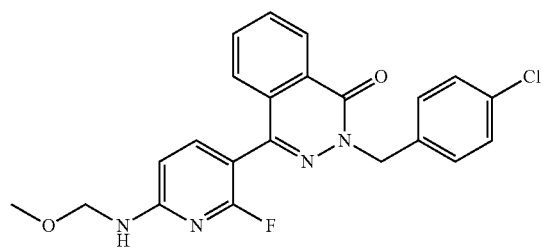 [SMILES: COCNc1ccc(-c2nn(Cc3ccc(Cl)cc3)c(=O)c3ccccc23)c(F)n1]<br>Compound I-15 was prepared in the same method as that in Example 1, except that 2-fluoro-6-methoxymethylamino-pyridine-3-boronic acid pinacol ester was used in place of pyridine-4-boronic acid. (White crystal, yield 43%)<br>$^1$H NMR (300 MHz, CD$_3$OD) δ 8.43 (s, 1H), 8.18 (s, 1H), 7.95 (d, J = 8.7 Hz, 1H), 7.84 (s, 2H), 7.66 (s, 1H), 7.51 (s, 1H), 7.40 (d, J = 7.7 Hz, 2H), 7.28 (d, J = 7.9 Hz, 2H), 5.40 (s, 2H), 4.80 (s, 2H), 3.40 (s, 3H). |
| I-16 | 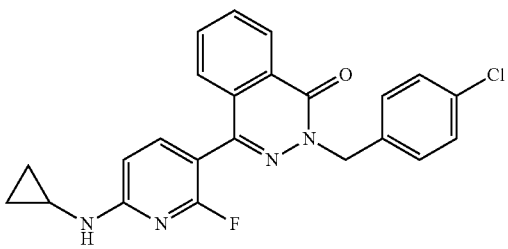 [SMILES: O=c1c2ccccc2c(-c2ccc(NC3CC3)nc2F)nn1Cc1ccc(Cl)cc1]<br>Compound I-16 was prepared in the same method as that in Example 1, except that 2-fluoro-6-cyclopropylamino-pyridine-3-boronic acid pinacol ester was used in place of pyridine-4-boronic acid. (White crystal, yield 51%)<br>$^1$H NMR (500 MHz, CDCl$_3$) δ 8.36 (s, 1H), 7.84 (s, 1H), 7.65 (d, J = 5.0 Hz, 2H), 7.59 (d, J = 5.0 Hz, 2H), 7.39 (s, 2H), 7.32 (s, 2H), 4.87 (s, 2H), 3.16 (s, 1H), 2.37 (s, 1H), 0.82 (s, 2H), 0.57 (s, 2H). |
| I-17 | 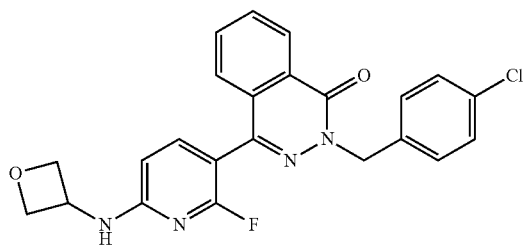 [SMILES: O=c1c2ccccc2c(-c2ccc(NC3COC3)nc2F)nn1Cc1ccc(Cl)cc1]<br>Compound I-17 was prepared in the same method as that in Example 1, except that 2-fluoro-6-oxetanylamino-pyridine-3-boronic acid pinacol ester was used in place of pyridine-4-boronic acid. (White crystal, yield 44%)<br>$^1$H NMR (400 MHz, CDCl$_3$) δ 7.96 (dd, J = 9.8, 8.4 Hz, 1H), 7.65 (d, J = 5.0 Hz, 2H), 7.59 (d, J = 5.0 Hz, 2H), 7.54 (s, 1H), 7.43 (d, J = 8.4 Hz, 2H), 7.32 (d, |

| Compounds | Preparation methods and structures of the products |
|---|---|
| | J = 8.4 Hz, 2H), 6.34 (dd, J = 8.3, 1.8 Hz, 1H), 5.34 (s, 2H), 5.28-5.26 (m, 1H), 5.06-5.03 (m, 2H), 4.59 (d, J = 5.7 Hz, 2H). |
| I-18 | 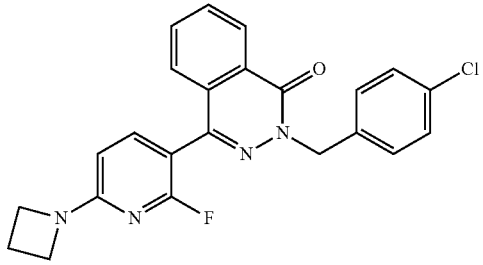 [SMILES: O=c1c2ccccc2c(-c2ccc(N3CCC3)nc2F)nn1Cc1ccc(Cl)cc1] Compound I-18 was prepared in the same method as that in Example 1, except that 2-fluoro-6-azetidinyl-pyridine-3-boronic acid was used in place of pyridine-4-boronic acid. (White crystal, yield 47%) $^1$H NMR (400 MHz, CDCl$_3$) δ 8.54-8.48 (m, 1H), 7.81-7.74 (m, 2H), 7.62 (dd, J = 9.3, 8.2 Hz, 1H), 7.59-7.54 (m, 1H), 7.46 (d, J = 8.4 Hz, 2H), 7.32-7.29 (m, 2H), 6.22 (dd, J = 8.2, 1.9 Hz, 1H), 5.42 (s, 2H), 4.17 (t, J = 7.5 Hz, 4H), 2.53-2.45 (m, 2H). |
| I-19 | 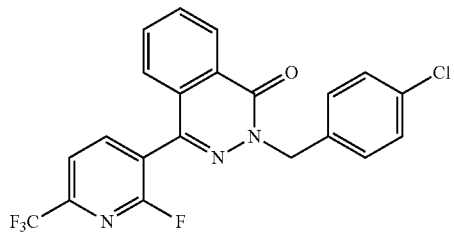 [SMILES: O=c1c2ccccc2c(-c2ccc(C(F)(F)F)nc2F)nn1Cc1ccc(Cl)cc1] Compound I-19 was prepared in the same method as that in Example 1, except that 2-fluoro-6-trifluoromethyl-pyridine-3-boronic acid was used in place of pyridine-4-boronic acid. (White crystal, yield 53%) $^1$H NMR (500 MHz, CDCl$_3$) δ 8.67 (dd, J = 15.0, 10.1 Hz, 1H), 7.87-7.81 (m, 1H), 7.69-7.63 (m, 2H), 7.64-7.53 (m, 1H), 7.48 (d, J = 15.0 Hz, 1H), 7.43-7.29 (m, 4H), 4.87 (s, 2H). |
| I-20 | 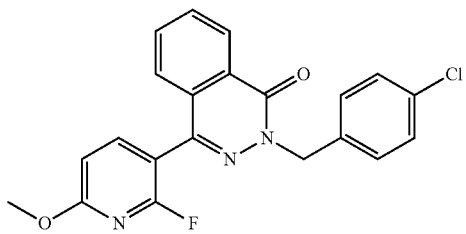 [SMILES: COc1ccc(-c2nn(Cc3ccc(Cl)cc3)c(=O)c3ccccc23)c(F)n1] Compound I-20 was prepared in the same method as that in Example 1, except that 2-fluoro-6-methoxy-pyridine-3-boronic acid was used in place of pyridine-4-boronic acid. (White crystal, yield 63%) $^1$H NMR (500 MHz, CDCl$_3$) δ 8.67 (s, 1H), 7.84 (s, 1H), 7.65 (d, J = 5.0 Hz, 2H), 7.58 (s, 1H), 7.36 (d, J = 35.0 Hz, 4H), 6.90 (s, 1H), 4.87 (s, 2H), 3.80 (s, 3H). |
| I-21 | 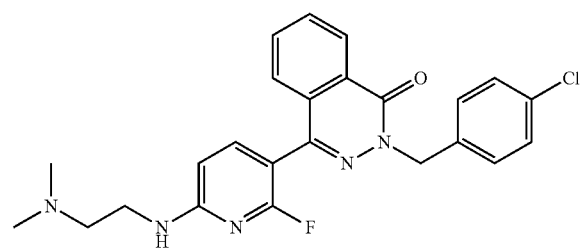 [SMILES: CN(C)CCNc1ccc(-c2nn(Cc3ccc(Cl)cc3)c(=O)c3ccccc23)c(F)n1] Compound I-21 was prepared in the same method as that in Example 1, except that 2-fluoro-6-(N,N-dimethylaminoethylamino)-pyridine-3-boronic acid was used in place of pyridine-4-boronic acid. (White crystal, yield 30%) |

| Compounds | Preparation methods and structures of the products |
|---|---|
| | ¹H NMR (500 MHz, CDCl₃) δ 8.35 (dd, J = 15.0, 9.9 Hz, 1H), 7.86-7.81 (m, 1H), 7.67-7.62 (m, 2H), 7.58 (ddd, J = 15.4, 8.4, 3.1 Hz, 2H), 7.40-7.28 (m, 4H), 4.87 (s, 2H), 3.60 (t, J = 10.3 Hz, 2H), 2.61 (t, J = 10.4 Hz, 2H), 2.26 (s, 6H). |
| I-22 | 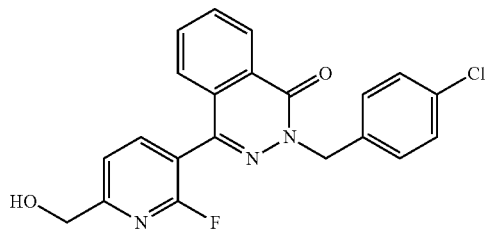 [SMILES: O=c1c2ccccc2c(-c2ccc(CO)nc2F)nn1Cc1ccc(Cl)cc1] Compound I-22 was prepared in the same method as that in Example 1, except that 2-fluoro-6-hydroxymethyl-pyridine-3-boronic acid was used in place of pyridine-4-boronic acid. (White crystal, yield 37%) ¹H NMR (500 MHz, CDCl₃) δ 8.56-8.51 (m, 1H), 7.96 (dd, J = 8.9, 7.6 Hz, 1H), 7.86-7.77 (m, 2H), 7.46 (d, J = 8.1 Hz, 4H), 7.32 (d, J = 8.4 Hz, 2H), 5.43 (s, 2H), 4.88 (d, J = 5.5 Hz, 2H), 2.96 (t, J = 5.6 Hz, 1H). |
| I-23 | 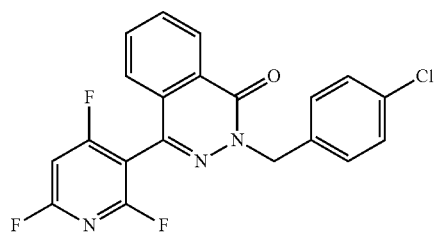 [SMILES: O=c1c2ccccc2c(-c2c(F)cc(F)nc2F)nn1Cc1ccc(Cl)cc1] Compound I-23 was prepared in the same method as in Example 1, except that 2,4,6-trifluoropyridine-3-boronic acid was used in place of pyridine-4-boronic acid. (White crystal, yield 12%) ¹H NMR (500 MHz, CDCl₃) δ 7.84 (s, 1H), 7.65 (d, J = 5.0 Hz, 2H), 7.58 (s, 1H), 7.36 (d, J = 35.0 Hz, 4H), 7.28 (s, 1H), 4.87 (s, 2H). |
| I-28 | 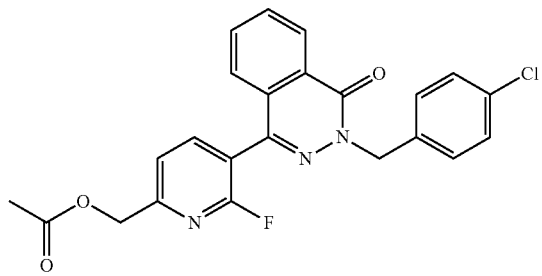 [SMILES: CC(=O)OCc1ccc(-c2nn(Cc3ccc(Cl)cc3)c(=O)c3ccccc23)c(F)n1] Compound I-28 was prepared in the same method as that in Example 1, except that 2-fluoro-6-acetoxymethylpyridine-3-boronic acid was used in place of pyridine-4-boronic acid. (White crystal, yield 32%) ¹H NMR (500 MHz, CDCl₃) δ 8.97 (s, 1H), 7.85 (d, J = 5.0 Hz, 2H), 7.69-7.51 (m, 3H), 7.36 (d, J = 35.0 Hz, 4H), 5.79 (s, 2H), 4.87 (s, 2H), 2.09 (s, 3H). |
| I-29 | 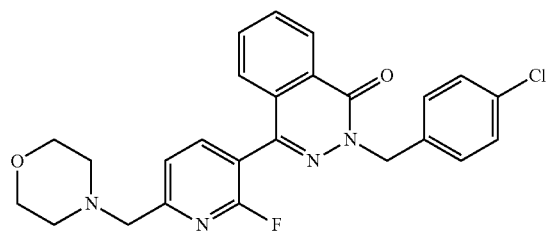 [SMILES: O=c1c2ccccc2c(-c2ccc(CN3CCOCC3)nc2F)nn1Cc1ccc(Cl)cc1] Compound I-29 was prepared in the same method as that in Example 1, except that 2-fluoro-6-morpholinemethyl-pyridine-3-boronic acid pinacol ester was used in place of pyridine-4-boronic acid. (White crystal, yield 15%) ¹H NMR (400 MHz, DMSO) δ 8.74 (s, 1H), 7.84 (s, 1H), 7.73-7.63 (m, 3H), 7.58 (s, 1H), 7.35 (d, J = 35.0 Hz, 4H), 4.87 (s, 2H), 3.94 (s, 2H), 3.57 (s, 4H), 2.42 (s, 4H). |

| Compounds | Preparation methods and structures of the products |
|---|---|
| I-30 | 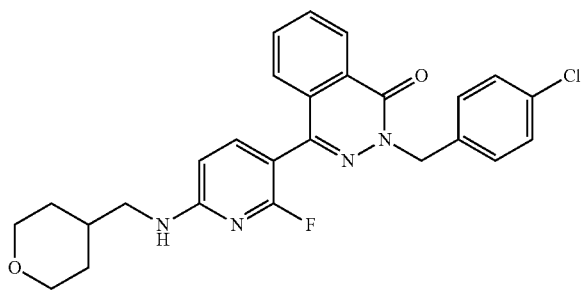 [SMILES: O=c1c2ccccc2c(-c2ccc(NCC3CCOCC3)nc2F)nn1Cc1ccc(Cl)cc1]<br><br>Compound I-30 was prepared in the same method as that in Example 1, except that 2-fluoro-6-(tetrahydrofuran-4-ylmethylamino)-pyridine-3-boronic acid pinacol ester was used in place of pyridine-4-boronic acid. (White crystal, yield 53%)<br>$^1$H NMR (500 MHz, CDCl$_3$) δ 8.36 (s, 1H), 7.84 (s, 1H), 7.65 (d, J = 5.0 Hz, 2H), 7.59 (d, J = 5.0 Hz, 2H), 7.36 (d, J = 35.0 Hz, 4H), 4.87 (s, 2H), 3.65 (d, J = 50.0 Hz, 4H), 3.36 (s, 2H), 2.29 (s, 1H), 1.70 (s, 1H), 1.55 (s, 2H), 1.30 (s, 2H). |
| I-31 | 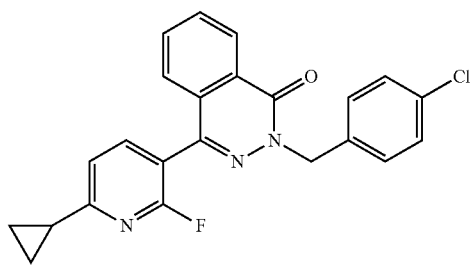 [SMILES: O=c1c2ccccc2c(-c2ccc(C3CC3)nc2F)nn1Cc1ccc(Cl)cc1]<br><br>Compound I-31 was prepared in the same method as that in Example 1, except that 2-fluoro-6-cyclopropyl-pyridine-3-boronic acid was used in place of pyridine-4-boronic acid. (White crystal, yield 56%)<br>$^1$H NMR (500 MHz, CDCl$_3$) δ 8.59 (s, 1H), 7.84 (s, 1H), 7.66 (d, J = 5.0 Hz, 2H), 7.58 (s, 1H), 7.36 (d, J = 35.0 Hz, 5H), 4.87 (s, 2H), 2.22 (s, 1H), 1.24 (s, 2H), 0.99 (s, 2H). |
| I-32 | 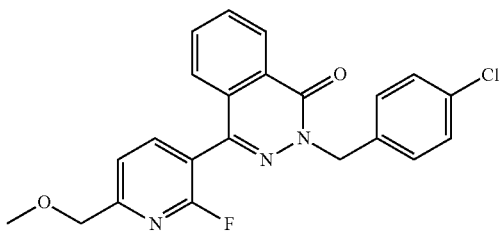 [SMILES: COCc1ccc(-c2nn(Cc3ccc(Cl)cc3)c(=O)c3ccccc23)c(F)n1]<br><br>Compound I-32 was prepared in the same method as that in Example 1, except that 2-fluoro-6-methoxymethyl-pyridine-3-boronic acid was used in place of pyridine-4-boronic acid. (White crystal, yield 47%)<br>$^1$H NMR (500 MHz, CDCl$_3$) δ 8.97 (s, 1H), 7.84 (d, J = 5.0 Hz, 2H), 7.65 (d, J = 5.0 Hz, 2H), 7.58 (s, 1H), 7.35 (d, J = 35.0 Hz, 4H), 4.87 (s, 2H), 4.44 (s, 2H), 3.27 (s, 3H). |
| I-33 | 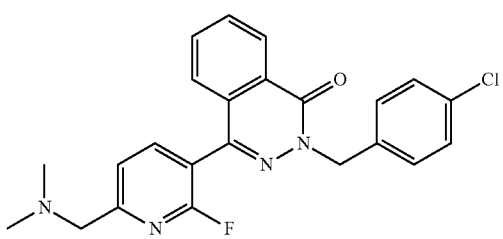 [SMILES: CN(C)Cc1ccc(-c2nn(Cc3ccc(Cl)cc3)c(=O)c3ccccc23)c(F)n1]<br><br>Compound I-33 was prepared in the same method as that in Example 1, except that 2-fluoro-6-(dimethylaminomethyl)-pyridine-3-boronic acid was |

| Compounds | Preparation methods and structures of the products |
|---|---|
| | used in place of pyridine-4-boronic acid. (White crystal, yield 63%)<br>¹H NMR (500 MHz, CDCl₃) δ 8.74 (s, 1H), 7.84 (s, 1H), 7.70-7.54 (m, 4H), 7.36 (d, J = 35.0 Hz, 4H), 4.87 (s, 2H), 3.94 (s, 2H), 2.16 (s, 6H). |
| I-34 | Compound I-34 was prepared in the same method as that in Example 1, except that 2-fluoro-6-(deuterated methyl)-pyridine-3-boronic acid was used in place of pyridine-4-boronic acid. (White crystal, yield 53%)<br>¹H NMR (400 MHz, CDCl₃) δ 8.55-8.49 (m, 1H), 7.85-7.76 (m, 3H), 7.49-7.43 (m, 3H), 7.33-7.30 (m, 2H), 7.25 (dd, J = 7.6, 1.7 Hz, 1H), 5.43 (s, 2H). |
| I-35 | Compound I-35 was prepared in the same method as that in Example 1, except that 2-fluoro-6-(methoxydeuterated methyl)-pyridine-3-boronic acid was used in place of pyridine-4-boronic acid. (White crystal, yield 63%)<br>¹H NMR (400 MHz, CDCl₃) δ 8.55-8.49 (m, 1H), 7.85-7.76 (m, 3H), 7.49-7.43 (m, 3H), 7.33-7.30 (m, 2H), 7.25 (dd, J = 7.6, 1.7 Hz, 1H), 5.43 (s, 2H). 3.86(s, 3H). |
| I-36 | Compound I-36 was prepared in the same method as that in Example 1, except that 2-fluoro-6-(deuterated methoxydeuterated methyl)-pyridine-3-boronic acid was used in place of pyridine-4-boronic acid. (White crystal, yield 41%)<br>¹H NMR (400 MHz, CDCl₃) δ 8.55-8.49 (m, 1H), 7.85-7.76 (m, 3H), 7.49-7.43 (m, 3H), 7.33-7.30 (m, 2H), 7.25 (dd, J = 7.6, 1.7 Hz, 1H), 5.43 (s, 2H). |
| I-37 | |

| Compounds | Preparation methods and structures of the products |
|---|---|
| | Compound I-37 was prepared in the same method as that in Example 1, except that 2-fluoro-6-(N, N-dimethyldimethylaminodeuterated methyl)-pyridine-3-boronic acid was used in place of pyridine-4-boronic acid. (White crystal, yield 33%)<br>$^1$H NMR (400 MHz, CDCl$_3$) δ 8.55-8.49 (m, 1H), 7.85-7.76 (m, 3H), 7.49-7.43 (m, 3H), 7.33-7.30 (m, 2H), 7.25 (dd, J = 7.6, 1.7 Hz, 1H), 5.43 (s, 2H), 2.16 (s, 6H). |
| I-38 | 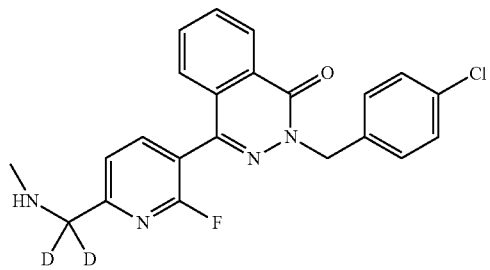 [SMILES: [2H]C([2H])(NC)c1ccc(-c2nn(Cc3ccc(Cl)cc3)c(=O)c3ccccc23)c(F)n1] |
| | Compound I-38 was prepared in the same method as that in Example 1, except that 2-fluoro-6-(N-methylaminodeuterated methyl)-pyridine-3-boronic acid was used in place of pyridine-4-boronic acid. (White crystal, yield 36%)<br>$^1$H NMR (400 MHz, CDCl$_3$) δ 8.55-8.49 (m, 1H), 7.85-7.76 (m, 3H), 7.49-7.43 (m, 3H), 7.33-7.30 (m, 2H), 7.25 (dd, J = 7.6, 1.7 Hz, 1H), 5.43 (s, 2H), 2.14 (s, 3H). |
| I-39 | 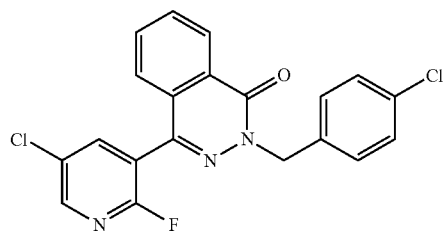 [SMILES: O=c1c2ccccc2c(-c2cc(Cl)cnc2F)nn1Cc1ccc(Cl)cc1] |
| | The above compound was prepared in the same method as that in Example 1, except that 2-fluoro-5-chloro-pyridine-3-boronic acid was used in place of pyridine-4-boronic acid. (White crystal, yield 68%)<br>$^1$H NMR (400 MHz, Chloroform-d) δ 8.54 (dd, J = 7.5, 1.9 Hz, 1H), 8.37 (dd, J = 2.8, 1.4 Hz, 1H), 7.94 (dd, J = 7.7, 2.7 Hz, 1H), 7.83 (tt, J = 7.4, 5.6 Hz, 2H), 7.50-7.41 (m, 3H), 7.35-7.30 (m, 2H), 5.43 (s, 2H). |
| I-40 | 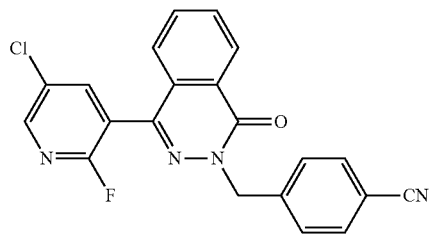 [SMILES: N#Cc1ccc(Cn2nc(-c3cc(Cl)cnc3F)c3ccccc3c2=O)cc1] |
| | The above compound was prepared in the same method as that in Example 1, except that 4-cyanobenzyl chloride was used in place of p-chlorobenzyl chloride and 2-fluoro-5-chloro-pyridine-3-boronic acid was used in place of pyridine-4-boronic acid. (White crystal, yield 73%)<br>$^1$H NMR (400 MHz, Chloroform-d) δ 8.57-8.50 (m, 1H), 8.38 (dd, J = 2.6, 1.4 Hz, 1H), 7.94 (dd, J = 7.7, 2.6 Hz, 1H), 7.90-7.82 (m, 2H), 7.66 (d, 2H), 7.60 (d, 2H), 7.49-7.44 (m, 1H), 5.50 (s, 2H). |

| Compounds | Preparation methods and structures of the products |
|---|---|
| I-41 | 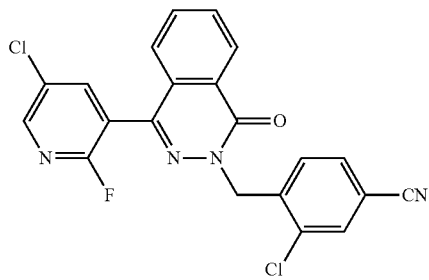 [SMILES: N#Cc1ccc(Cn2nc(-c3cc(Cl)cnc3F)c3ccccc3c2=O)c(Cl)c1]

The above compound was prepared in the same method as that in Example 1, except that 2-chloro-4-cyanobenzyl chloride was used in place of p-chlorobenzyl chloride and 2-fluoro-5-chloro-pyridine-3-boronic acid was used in place of pyridine-4-boronic acid. (White crystal, yield 65%)
$^1$H NMR (400 MHz, Chloroform-d) δ 8.61-8.53 (m, 1H), 8.37 (dd, J = 2.7, 1.4 Hz, 1H), 7.93 (dd, J = 7.7, 2.6 Hz, 1H), 7.91-7.86 (m, 2H), 7.73 (d, J = 1.6 Hz, 1H), 7.54-7.51 (m, 2H), 7.49 (td, J = 3.0, 2.2 Hz, 1H), 5.64 (s, 2H). |
| I-42 | 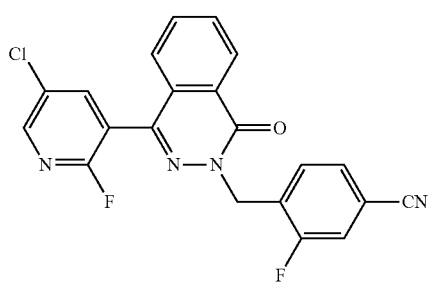 [SMILES: N#Cc1ccc(Cn2nc(-c3cc(Cl)cnc3F)c3ccccc3c2=O)c(F)c1]

The above compound was prepared in the same method as that in Example 1, except that 2-fluoro-4-cyanobenzyl chloride was used in place of p-chlorobenzyl chloride and 2-fluoro-5-chloro-pyridine-3-boronic acid was used in place of pyridine-4-boronic acid. (White crystal, 71% yield)
$^1$H NMR (400 MHz, Chloroform-d) δ 8.58-8.50 (m, 1H), 8.37 (dd, J = 2.6, 1.4 Hz, 1H), 7.93 (dd, J = 7.7, 2.7 Hz, 1H), 7.90-7.84 (m, 2H), 7.54-7.39 (m, 4H), 5.58 (s, 2H). |
| I-43 | 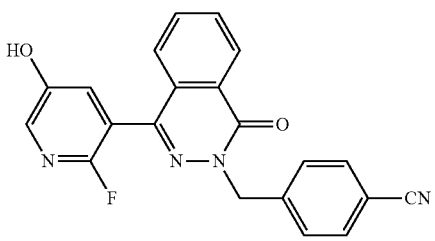 [SMILES: N#Cc1ccc(Cn2nc(-c3cc(O)cnc3F)c3ccccc3c2=O)cc1]

The above compound was prepared in the same method as that in Example 1, except that 4-cyanobenzyl chloride was used in place of p-chlorobenzyl chloride, and 2-fluoro-5-hydroxy-pyridine-3-boronic acid was used in place of pyridine-4-boronic acid. (White crystal, yield 55%)
$^1$H NMR (400 MHz, Chloroform-d) δ 8.66-8.57 (m, 1H), 8.10 (s, 1H), 7.99-7.83 (m, 3H), 7.69 (d, J = 8.1 Hz, 2H), 7.59 (d, J = 8.1 Hz, 2H), 7.09 (d, J = 2.7 Hz, 1H). |
| I-44 | 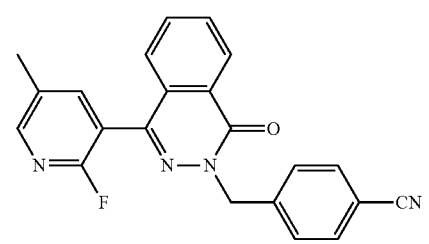 [SMILES: Cc1cnc(F)c(-c2nn(Cc3ccc(C#N)cc3)c(=O)c3ccccc23)c1]

The above compound was prepared in the same method as that in Example 1, except that 4-cyanobenzyl chloride was used in place of p-chlorobenzyl |

| Compounds | Preparation methods and structures of the products |
|---|---|
| | chloride, and 2-fluoro-5-methyl-pyridine-3-boronic acid was used in place of pyridine-4-boronic acid. (White crystal, yield 76%)<br>¹H NMR (400 MHz, Chloroform-d) δ 8.53 (dd, J = 7.1, 2.1 Hz, 1H), 8.23 (s, 1H), 7.83 (tt, J = 7.3, 6.0 Hz, 2H), 7.74 (dd, J = 8.8, 2.5 Hz, 1H), 7.66 (d, J = 8.2 Hz, 2H), 7.60 (d, J = 8.3 Hz, 2H), 7.47 (dd, J = 5.8, 3.5 Hz, 1H), 5.51 (s, 2H), 2.46 (s, 3H). |
| I-45 | 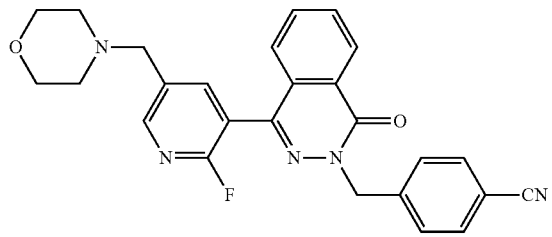 [SMILES: N#Cc1ccc(Cn2nc(-c3cc(CN4CCOCC4)cnc3F)c3ccccc3c2=O)cc1]<br>The above compound was prepared in the same method as that in Example 1, except that 4-cyanobenzyl chloride was used in place of p-chlorobenzyl chloride, and 2-fluoro-5-morpholinylmethyl-pyridine-3-boronic acid was used in place of pyridine-4-boronic acid. (White crystal, yield 61%)<br>¹H NMR (400 MHz, Chloroform-d) δ 8.54-8.49 (m, 1H), 8.33 (dd, J = 2.3, 1.1 Hz, 1H), 7.94 (dd, J = 8.9, 2.4 Hz, 1H), 7.82 (ddd, J = 7.9, 5.5, 1.7 Hz, 2H), 7.64 (d, J = 8.4 Hz, 2H), 7.58 (d, J = 8.3 Hz, 2H), 7.48-7.43 (m, 1H), 5.50 (s, 2H), 3.71 (dt, J = 7.0, 4.5 Hz, 4H), 3.61 (s, 2H), 2.51 (t, J = 4.6 Hz, 4H). |
| II-1 | 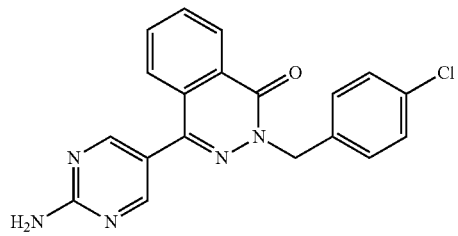 [SMILES: Nc1ncc(-c2nn(Cc3ccc(Cl)cc3)c(=O)c3ccccc23)cn1]<br>Compound II-1 was prepared in the same method as that in Example 1, except that 2-aminopyrimidine-5-boronic acid pinacol ester was used in place of pyridine-4-boronic acid. (White crystal, yield 56%)<br>¹H NMR (500 MHz, CDCl₃) δ 8.67 (s, 2H), 7.87-7.81 (m, 1H), 7.69-7.63 (m, 2H), 7.63-7.54 (m, 1H), 7.42-7.29 (m, 4H), 4.87 (s, 2H), 1.86 (s, 2H). |
| II-2 | 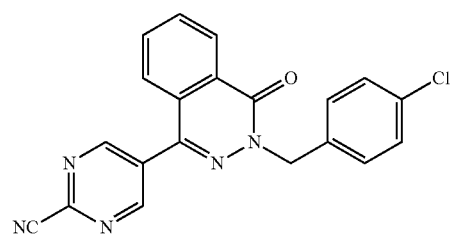 [SMILES: N#Cc1ncc(-c2nn(Cc3ccc(Cl)cc3)c(=O)c3ccccc23)cn1]<br>Compound II-2 was prepared in the same method as that in Example 1, except that 2-cyanopyrimidine-5-boronic acid pinacol ester was used in place of pyridine-4-boronic acid. (White crystal, yield 67%)<br>¹H NMR (500 MHz, CDCl₃) δ 9.33 (s, 2H), 7.87-7.80 (m, 1H), 7.70-7.63 (m, 2H), 7.62-7.54 (m, 1H), 7.44-7.28 (m, 4H), 4.87 (s, 2H). |
| II-3 | 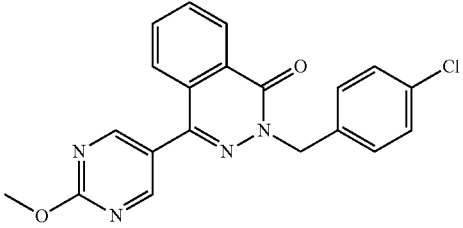 [SMILES: COc1ncc(-c2nn(Cc3ccc(Cl)cc3)c(=O)c3ccccc23)cn1]<br>Compound II-3 was prepared in the same method as that in Example 1, except that 2-methoxypyrimidine-5-boronic acid was used in place of pyridine- |

| Compounds | Preparation methods and structures of the products |
|---|---|
| | 4-boronic acid. (White crystal, yield 70%)<br>¹H NMR (400 MHz, CDCl₃) δ 9.01 (s, 2H), 7.87-7.81 (m, 1H), 7.67-7.63 (m, 2H), 7.63-7.54 (m, 1H), 7.44-7.24 (m, 4H), 4.87 (s, 2H), 3.85 (s, 3H). |
| II-4 | 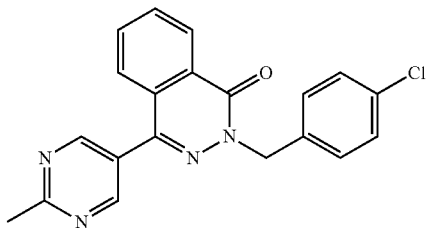 [SMILES: Cc1ncc(-c2nn(Cc3ccc(Cl)cc3)c(=O)c3ccccc23)cn1] |
| | Compound II-4 was prepared in the same method as that in Example 1, except that 2-methylpyrimidine-5-boronic acid was used in place of pyridine-4-boronic acid. (White crystal, yield 84%)<br>¹H NMR (300 MHz, CDCl₃) δ 8.92 (s, 2H), 7.87-7.81 (m, 1H), 7.68-7.63 (m, 2H), 7.62-7.54 (m, 1H), 7.42-7.28 (m, 4H), 4.87 (s, 2H), 2.18 (s, 3H). |
| III-1 | 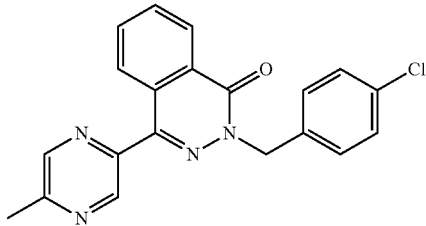 [SMILES: Cc1cnc(-c2nn(Cc3ccc(Cl)cc3)c(=O)c3ccccc23)cn1] |
| | Compound III-1 was prepared in the same method as that in Example 1, except that 2-methylpyrazine-5-boronic acid was used in place of pyridine-4-boronic acid. (White crystal, yield 33%)<br>¹H NMR (500 MHz, CDCl₃) δ 9.16 (s, 1H), 8.81 (s, 1H), 7.88-7.81 (m, 1H), 7.69-7.63 (m, 2H), 7.62-7.52 (m, 1H), 7.42-7.28 (m, 4H), 4.87 (s, 2H), 2.59 (s, 3H). |
| IV-1 | 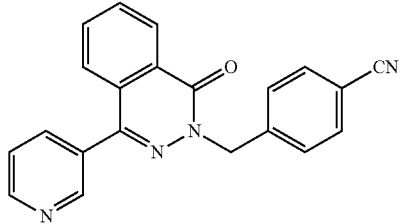 [SMILES: N#Cc1ccc(Cn2nc(-c3cccnc3)c3ccccc3c2=O)cc1] |
| | Compound IV-1 was prepared in the same method as that in Example 1, except that p-cyanobenzyl chloride was used in place of p-chlorobenzyl chloride. (White crystal, yield 85%)<br>¹H NMR (400 MHz, CDCl₃) δ 8.90 (t, J = 1.8 Hz, 1H), 8.75 (ddd, J = 4.6, 2.7, 1.8 Hz, 1H), 8.40 (dd, J = 7.8, 1.7 Hz, 1H), 7.99 (ddd, J = 7.9, 2.6, 1.8 Hz, 1H), 7.89 (dd, J = 7.7, 1.7 Hz, 1H), 7.77 (td, J = 7.7, 1.8 Hz, 1H), 7.71 (dd, J = 7.6, 1.7 Hz, 1H), 7.68 (dt, J = 7.3, 1.3 Hz, 2H), 7.64 (dt, J = 8.4, 1.0 Hz, 2H), 7.56 (dd, J = 7.9, 4.8 Hz, 1H), 5.41 (t, J = 1.0 Hz, 2H). |
| IV-2 | 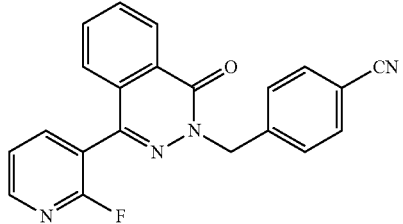 [SMILES: N#Cc1ccc(Cn2nc(-c3cccnc3F)c3ccccc3c2=O)cc1] |
| | Compound IV-2 was prepared in the same method as that in Example 1, except that p-cyanobenzyl chloride was used in place of p-chlorobenzyl chloride and 2-fluoro-pyridine-3-boronic acid was used in place of pyridine-4-boronic acid. (White crystal, yield 82%)<br>¹H NMR (400 MHz, CDCl₃) δ 8.56-8.52 (m, 1H), 8.45 (d, J = 4.9 Hz, 1H), |

| Compounds | Preparation methods and structures of the products |
|---|---|
| | 7.96 (ddd, J = 9.3, 7.4, 2.0 Hz, 1H), 7.89-7.79 (m, 2H), 7.68-7.58 (m, 4H), 7.51-7.40 (m, 2H), 5.51 (s, 2H). |
| IV-3 | 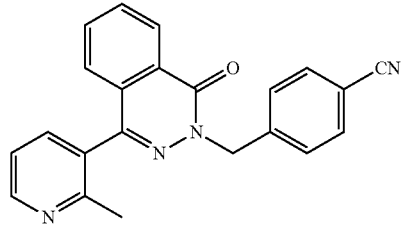 [SMILES: Cc1ncccc1-c1nn(Cc2ccc(C#N)cc2)c(=O)c2ccccc12]<br>Compound IV-3 was prepared in the same method as that in Example 1, except that p-cyanobenzyl chloride was used in place of p-chlorobenzyl chloride and 2-methyl-pyridine-3-boronic acid was used in place of pyridine-4-boronic acid. (White crystal, yield 77%)<br>$^1$H NMR (400 MHz, CDCl$_3$) δ 8.67 (dd, J = 3.5, 2.2 Hz, 1H), 8.37 (dd, J = 7.7, 1.7 Hz, 1H), 7.83-7.80 (m, 2H), 7.77 (td, J = 7.5, 1.6 Hz, 1H), 7.70-7.62 (m, 6H), 5.41 (t, J = 1.0 Hz, 2H). |
| IV-4 | 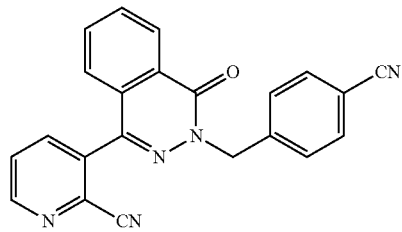<br>Compound IV-4 was prepared in the same method as in Example 1, except that p-cyanobenzyl chloride was used in place of p-chlorobenzyl chloride and 2-cyano-pyridine-3-boronic acid was used in place of pyridine-4-boronic acid. (White crystal, yield 85%)<br>$^1$H NMR (400 MHz, CDCl$_3$) δ 8.62 (dd, J = 3.5, 2.2 Hz, 1H), 8.35 (dd, J = 7.8, 1.7 Hz, 1H), 8.01 (dd, J = 7.9, 2.2 Hz, 1H), 7.90 (dd, J = 7.9, 3.5 Hz, 1H), 7.85 (dd, J = 7.7, 1.7 Hz, 1H), 7.78 (td, J = 7.5, 1.6 Hz, 1H), 7.71 (td, J = 7.6, 1.7 Hz, 1H), 7.69-7.60 (m, 4H), 5.39 (t, J = 1.0 Hz, 2H). |
| IV-5 | 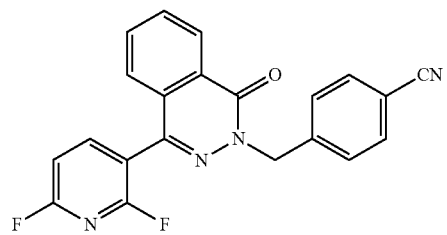 [SMILES: N#Cc1ccc(Cn2nc(-c3ccc(F)nc3F)c3ccccc3c2=O)cc1]<br>Compound IV-5 was prepared in the same method as that in Example 1, except that p-cyanobenzyl chloride was used in place of p-chlorobenzyl chloride and 2,6-difluoro-pyridine-3-boronic acid was used in place of pyridine-4-boronic acid. (White crystal, yield 75%)<br>$^1$H NMR (400 MHz, CDCl$_3$) δ 8.55 (dd, J = 6.9, 2.5 Hz, 1H), 8.05 (dd, J = 16.6, 7.8 Hz, 1H), 7.91-7.82 (m, 2H), 7.68-7.57 (m, 4H), 7.48-7.43 (m, 1H), 7.07 (dd, J = 8.1, 2.9 Hz, 1H), 5.50 (s, 2H). |
| IV-6 | 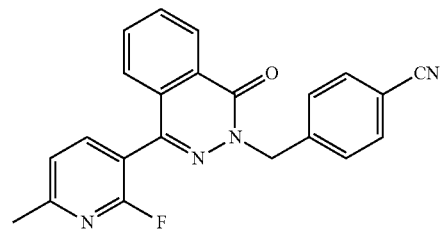 [SMILES: Cc1ccc(-c2nn(Cc3ccc(C#N)cc3)c(=O)c3ccccc23)c(F)n1]<br>Compound IV-6 was prepared in the same method as that in Example 1, except that p-cyanobenzyl chloride was used in place of p-chlorobenzyl chloride and 2-fluoro-6-methyl-pyridine-3-boronic acid was used in place of pyridine-4- |

| Compounds | Preparation methods and structures of the products |
|---|---|
| | boronic acid. (White crystal, 71% yield)<br>¹H NMR (400 MHz, CDCl₃) δ 8.50 (d, J = 6.8 Hz, 1H), 7.86-7.74 (m, 3H), 7.60 (q, J = 8.5 Hz, 4H), 7.47 (d, J = 6.9 Hz, 1H), 7.22 (s, 1H), 5.48 (s, 2H), 2.63 (s, 3H). |
| IV-7 | 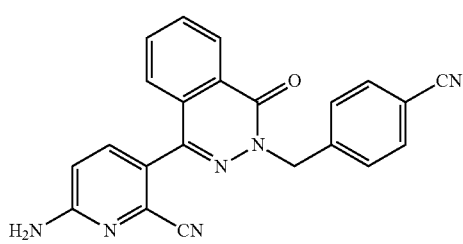 [SMILES: N#Cc1ccc(Cn2nc(-c3ccc(N)nc3C#N)c3ccccc3c2=O)cc1]<br>Compound IV-7 was prepared in the same method as that in Example 1, except that p-cyanobenzyl chloride was used in place of p-chlorobenzyl chloride and 2-fluoro-6-amino-pyridine-3-boronic acid pinacol ester was used in place of pyridine-4-boronic acid. (White crystal, yield 56%)<br>¹H NMR (400 MHz, CDCl₃) δ 8.55-8.46 (m, 1H), 7.85-7.79 (m, 2H), 7.63 (dt, J = 15.4, 5.5 Hz, 6H), 6.52 (dd, J = 8.0, 1.8 Hz, 1H), 5.50 (s, 2H), 4.81 (s, 2H). |
| IV-8 | 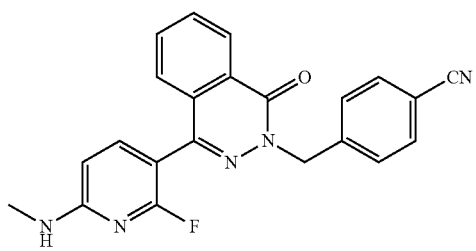 [SMILES: CNc1ccc(-c2nn(Cc3ccc(C#N)cc3)c(=O)c3ccccc23)c(F)n1]<br>Compound IV-8 was prepared in the same method as that in Example 1, except that p-cyanobenzyl chloride was used in place of p-chlorobenzyl chloride, and 2-fluoro-6-methylamino-pyridine-3-boronic acid pinacol ester was used in place of pyridine-4-boronic acid. (White crystal, yield 60%)<br>¹H NMR (400 MHz, CDCl₃) δ 8.36 (s, 1H), 7.85 (d, J = 5.0 Hz, 3H), 7.65 (d, J = 5.0 Hz, 2H), 7.59 (d, J = 5.0 Hz, 2H), 7.52 (s, 2H), 4.87 (s, 2H), 2.89 (s, 3H), 2.32 (s, 1H). |
| IV-9 | 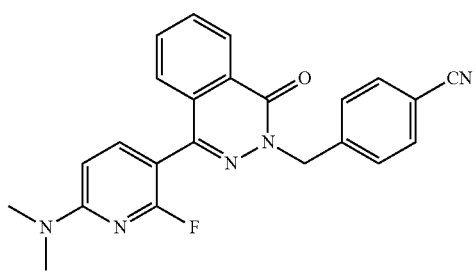 [SMILES: CN(C)c1ccc(-c2nn(Cc3ccc(C#N)cc3)c(=O)c3ccccc23)c(F)n1]<br>Compound IV-9 was prepared in the same method as that in Example 1, except that p-cyanobenzyl chloride was used in place of p-chlorobenzyl chloride, and 2-fluoro-6-dimethylamino-pyridine-3-boronic acid pinacol ester was used in place of pyridine-4-boronic acid. (White crystal, yield 77%)<br>¹H NMR (400 MHz, CDCl₃) δ 8.36 (dd, J = 15.0, 10.1 Hz, 1H), 7.87-7.82 (m, 3H), 7.67-7.63 (m, 2H), 7.63-7.56 (m, 2H), 7.55-7.49 (m, 2H), 4.87 (s, 2H), 3.15 (s, 6H). |
| IV-10 | 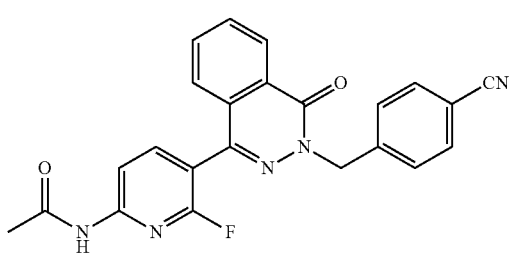 [SMILES: CC(=O)Nc1ccc(-c2nn(Cc3ccc(C#N)cc3)c(=O)c3ccccc23)c(F)n1] |

| Compounds | Preparation methods and structures of the products |
|---|---|
| | Compound IV-10 was prepared in the same method as that in Example 1, except that p-cyanobenzyl chloride was used in place of p-chlorobenzyl chloride, and 2-fluoro-6-acetamido-pyridine-3-boronic acid pinacol ester was used in place of pyridine-4-boronic acid. (White crystal, yield 43%)<br>$^1$H NMR (400 MHz, CDCl$_3$) δ 9.21 (d, J = 7.5 Hz, 1H), 8.83 (dd, J = 7.5, 5.0 Hz, 1H), 8.29 (s, 1H), 7.89-7.82 (m, 3H), 7.67-7.63 (m, 2H), 7.58 (ddd, J = 7.3, 6.2, 2.9 Hz, 1H), 7.52 (d, J = 7.5 Hz, 2H), 4.87 (s, 2H), 2.09 (s, 3H). |
| IV-11 | 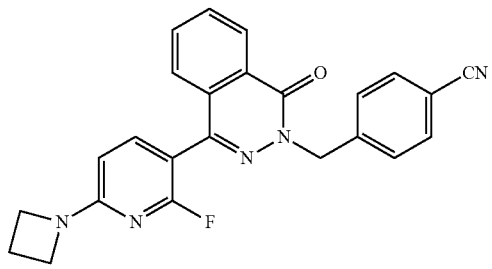 [SMILES: N#Cc1ccc(Cn2nc(-c3ccc(N4CCC4)nc3F)c3ccccc3c2=O)cc1] |
| | Compound IV-11 was prepared in the same method as that in Example 1, except that p-cyanobenzyl chloride was used in place of p-chlorobenzyl chloride and 2-fluoro-6-azetidinyl-pyridine-3-boronic acid was used in place of pyridine-4-boronic acid. (White crystal, yield 51%)<br>$^1$H NMR (400 MHz, CDCl$_3$) δ 8.51-8.46 (m, 1H), 7.83-7.75 (m, 2H), 7.60 (dt, J = 8.2, 5.8 Hz, 6H), 6.21 (d, J = 8.2 Hz, 1H), 5.49 (s, 2H), 4.16 (t, J = 7.5 Hz, 4H), 2.53-2.42 (m, 2H). |
| IV-12 | 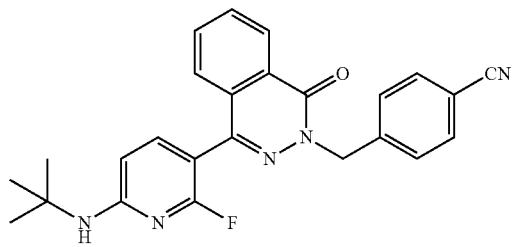 [SMILES: CC(C)(C)Nc1ccc(-c2nn(Cc3ccc(C#N)cc3)c(=O)c3ccccc23)c(F)n1] |
| | Compound IV-12 was prepared in the same method as that in Example 1, except that p-cyanobenzyl chloride was used in place of p-chlorobenzyl chloride and 2-fluoro-6-t-butylamino-pyridine-3-boronic acid pinacol ester was used in place of pyridine-4-boronic acid. (White crystal, yield 57%)<br>$^1$H NMR (400 MHz, CDCl$_3$) δ 8.36 (s, 1H), 7.85 (d, J = 5.0 Hz, 3H), 7.65 (d, J = 5.0 Hz, 2H), 7.59 (d, J = 5.0 Hz, 2H), 7.52 (s, 2H), 4.87 (s, 2H), 2.25 (s, 1H), 1.36 (s, 9H). |
| IV-13 | 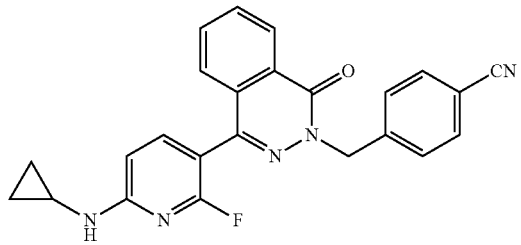 [SMILES: N#Cc1ccc(Cn2nc(-c3ccc(NC4CC4)nc3F)c3ccccc3c2=O)cc1] |
| | Compound IV-13 was prepared in the same method as that in Example 1, except that p-cyanobenzyl chloride was used in place of p-chlorobenzyl chloride, and 2-fluoro-6-cyclopropylamino-pyridine-3-boronic acid pinacol ester was used in place of pyridine-4-boronic acid. (White crystal, yield 49%)<br>$^1$H NMR (400 MHz, CDCl$_3$) δ 8.36 (s, 1H), 7.84 (d, J = 5.0 Hz, 3H), 7.65 (d, J = 5.0 Hz, 2H), 7.58 (d, J = 5.0 Hz, 2H), 7.52 (s, 2H), 4.87 (s, 2H), 3.19 (s, 1H), 2.36 (s, 1H), 0.82 (s, 2H), 0.57 (s, 2H). |

| Compounds | Preparation methods and structures of the products |
|---|---|
| IV-14 | 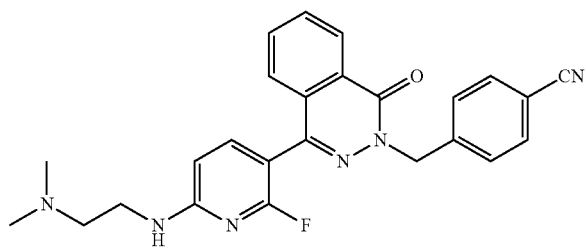 [SMILES: CN(C)CCNc1ccc(-c2nn(Cc3ccc(C#N)cc3)c(=O)c3ccccc23)c(F)n1]<br>Compound IV-14 was prepared in the same method as that in Example 1, except that p-cyanobenzyl chloride was used in place of p-chlorobenzyl chloride and 2-fluoro-6-(N,N-dimethylaminoethylamino)-pyridine-3-boronic acid was used in place of pyridine-4-boronic acid. (White crystal, yield 35%)<br>$^1$H NMR (400 MHz, CDCl$_3$) δ 8.36 (s, 1H), 7.85 (d, J = 5.0 Hz, 3H), 7.65 (d, J = 5.0 Hz, 2H), 7.59 (d, J = 5.0 Hz, 2H), 7.52 (s, 2H), 4.87 (s, 2H), 3.60 (s, 2H), 2.61 (s, 2H), 2.26 (s, 6H), 2.22 (s, 1H). |
| IV-15 | 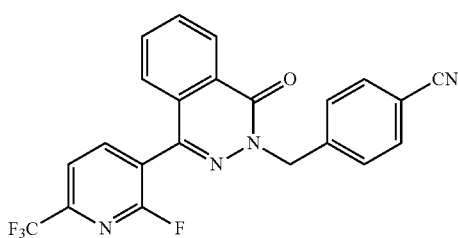<br>Compound IV-15 was prepared in the same method as that in Example 1, except that p-cyanobenzyl chloride was used in place of p-chlorobenzyl chloride and 2-fluoro-6-trifluoromethyl-pyridine-3-boronic acid was used in place of pyridine-4-boronic acid. (White crystal, yield 65%)<br>$^1$H NMR (400 MHz, CDCl$_3$) δ 8.58-8.54 (m, 1H), 8.16 (t, J = 8.1 Hz, 1H), 7.91-7.80 (m, 3H), 7.63 (dd, J = 23.4, 8.3 Hz, 4H), 7.45 (d, J = 7.4 Hz, 1H), 5.51 (s, 2H). |
| IV-16 | 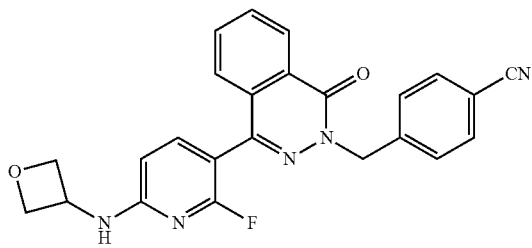 [SMILES: N#Cc1ccc(Cn2nc(-c3ccc(NC4COC4)nc3F)c3ccccc3c2=O)cc1]<br>Compound IV-16 was prepared in the same method as that in Example 1, except that p-cyanobenzyl chloride was used in place of p-chlorobenzyl chloride, and 2-fluoro-6-oxetanylamino-pyridine-3-boronic acid pinacol ester was used in place of pyridine-4-boronic acid. (White crystal, yield 33%)<br>$^1$H NMR (400 MHz, CDCl$_3$) δ 8.36 (s, 1H), 7.85 (d, J = 5.0 Hz, 3H), 7.65 (d, J = 5.0 Hz, 2H), 7.59 (d, J = 5.0 Hz, 2H), 7.52 (s, 2H), 4.87 (s, 2H), 5.24-5.21 (m, 1H), 4.98-4.96 (m, 2H), 4.53 (d, J = 5.7 Hz, 2H). |
| IV-19 | 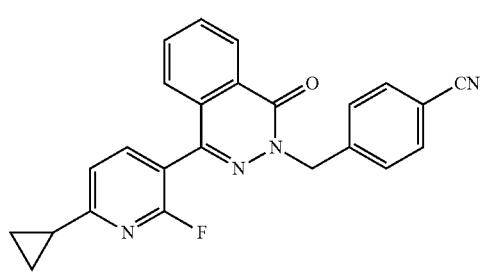 [SMILES: N#Cc1ccc(Cn2nc(-c3ccc(C4CC4)nc3F)c3ccccc3c2=O)cc1]<br>Compound IV-19 was prepared in the same method as that in Example 1, except that p-cyanobenzyl chloride was used in place of p-chlorobenzyl chloride and 2-fluoro-6-cyclopropyl-pyridine-3-boronic acid was used in place of |

| Compounds | Preparation methods and structures of the products |
|---|---|
| | pyridine-4-boronic acid. (White crystal, yield 37%)<br>¹H NMR (400 MHz, CDCl₃) δ 8.59 (s, 1H), 7.85 (d, J = 5.0 Hz, 3H), 7.66 (d, J = 5.0 Hz, 2H), 7.58 (s, 1H), 7.52 (s, 2H), 7.39 (s, 1H), 4.87 (s, 2H), 2.22 (s, 1H), 1.24 (s, 2H), 0.99 (s, 2H). |
| IV-20 | 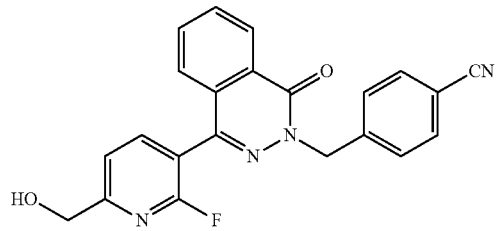 [SMILES: N#Cc1ccc(Cn2nc(-c3ccc(CO)nc3F)c3ccccc3c2=O)cc1]<br>Compound IV-20 was prepared in the same method as that in Example 1, except that p-cyanobenzyl chloride was used in place of p-chlorobenzyl chloride and 2-fluoro-6-hydroxymethyl-pyridine-3-boronic acid was used in place of pyridine-4-boronic acid. (White crystal, yield 25%)<br>¹H NMR (400 MHz, CDCl₃) δ 8.97 (s, 1H), 7.85 (d, J = 5.0 Hz, 4H), 7.65 (d, J = 5.0 Hz, 2H), 7.58 (s, 1H), 7.52 (s, 2H), 4.87 (s, 2H), 4.13 (s, 1H). |
| IV-21 | 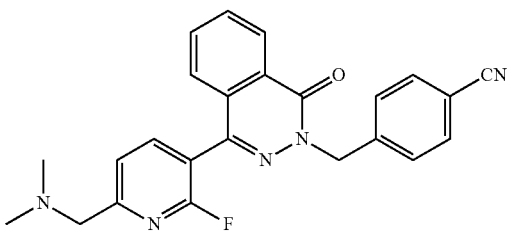 [SMILES: CN(C)Cc1ccc(-c2nn(Cc3ccc(C#N)cc3)c(=O)c3ccccc23)c(F)n1]<br>Compound IV-21 was prepared in the same method as that in Example 1, except that p-cyanobenzyl chloride was used in place of p-chlorobenzyl chloride, and 2-fluoro-6-(dimethylaminomethyl)-pyridine-3-boronic acid was used in place of pyridine-4-boronic acid. (White crystal, yield 41%)<br>¹H NMR (400 MHz, CDCl₃) δ 8.74 (s, 1H), 7.84 (d, J = 5.0 Hz, 3H), 7.70-7.63 (m, 3H), 7.58 (s, 1H), 7.52 (s, 2H), 4.87 (s, 2H), 3.94 (s, 2H), 2.16 (s, 6H). |
| IV-22 | 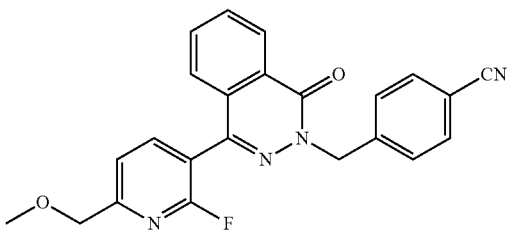 [SMILES: COCc1ccc(-c2nn(Cc3ccc(C#N)cc3)c(=O)c3ccccc23)c(F)n1]<br>Compound IV-22 was prepared in the same method as that in Example 1, except that p-cyanobenzyl chloride was used in place of p-chlorobenzyl chloride and 2-fluoro-6-methoxymethyl-pyridine-3-boronic acid was used in place of pyridine-4-boronic acid. (White crystal, yield 45%)<br>¹H NMR (400 MHz, CDCl₃) δ 8.97 (s, 1H), 7.85 (d, J = 5.0 Hz, 4H), 7.65 (d, J = 5.0 Hz, 2H), 7.58 (s, 1H), 7.52 (s, 2H), 4.87 (s, 2H), 4.44 (s, 2H), 3.27 (s, 3H). |
| IV-23 | 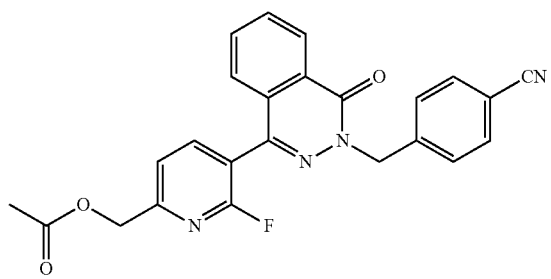 [SMILES: CC(=O)OCc1ccc(-c2nn(Cc3ccc(C#N)cc3)c(=O)c3ccccc23)c(F)n1]<br>Compound IV-23 was prepared in the same method as that in Example 1, except that p-cyanobenzyl chloride was used in place of p-chlorobenzyl chloride |

| Compounds | Preparation methods and structures of the products |
|---|---|
| | and 2-fluoro-6-acetoxymethylpyridine-3-boronic acid was used in place of pyridine-4-boronic acid. (White crystal, yield 30%)<br>¹H NMR (400 MHz, CDCl₃) δ 8.97 (s, 1H), 7.84 (d, J = 5.0 Hz, 4H), 7.65 (d, J = 5.0 Hz, 2H), 7.58 (s, 1H), 7.52 (s, 2H), 5.79 (s, 2H), 4.87 (s, 2H), 2.09 (s, 3H). |
| IV-24 | 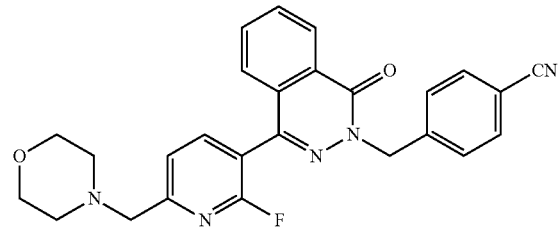 [SMILES: N#Cc1ccc(Cn2nc(-c3ccc(CN4CCOCC4)nc3F)c3ccccc3c2=O)cc1]<br>Compound IV-24 was prepared in the same method as that in Example 1, except that p-cyanobenzyl chloride was used in place of p-chlorobenzyl chloride and 2-fluoro-6-morpholinemethyl-pyridine-3-boronic acid pinacol ester was used in place of pyridine-4-boronic acid. (White crystal, yield 38%)<br>¹H NMR (400 MHz, CDCl₃) δ 8.74 (s, 1H), 7.84 (d, J = 5.0 Hz, 3H), 7.70-7.63 (m, 3H), 7.58 (s, 1H), 7.52 (s, 2H), 4.87 (s, 2H), 3.94 (s, 2H), 3.57 (s, 4H), 2.42 (s, 4H). |
| IV-25 | 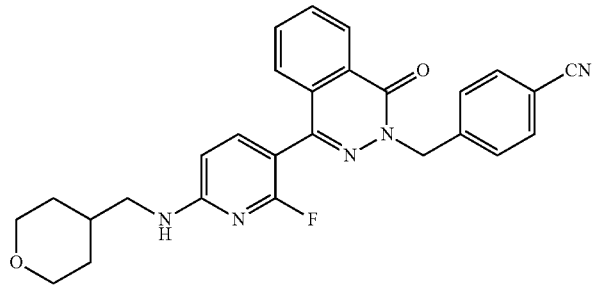 [SMILES: N#Cc1ccc(Cn2nc(-c3ccc(NCC4CCOCC4)nc3F)c3ccccc3c2=O)cc1]<br>Compound IV-25 was prepared in the same method as that in Example 1, except that p-cyanobenzyl chloride was used in place of p-chlorobenzyl chloride, 2-fluoro-6-(tetrahydrofuran-4-ylmethylamino)-pyridine-3-boronic acid pinacol ester was used in place of pyridine-4-boronic acid. (White crystal, yield 17%)<br>¹H NMR (400 MHz, CDCl₃) δ 8.36 (s, 1H), 7.84 (d, J = 5.0 Hz, 3H), 7.65 (d, J = 5.0 Hz, 2H), 7.58 (d, J = 5.0 Hz, 2H), 7.52 (s, 2H), 4.87 (s, 2H), 3.65 (d, J = 50.0 Hz, 4H), 3.36 (s, 2H), 2.29 (s, 1H), 1.68 (s, 1H), 1.55 (s, 2H), 1.30 (s, 2H). |

Example 2

The Scheme for Synthesizing Compound I-24 is Shown as Below:

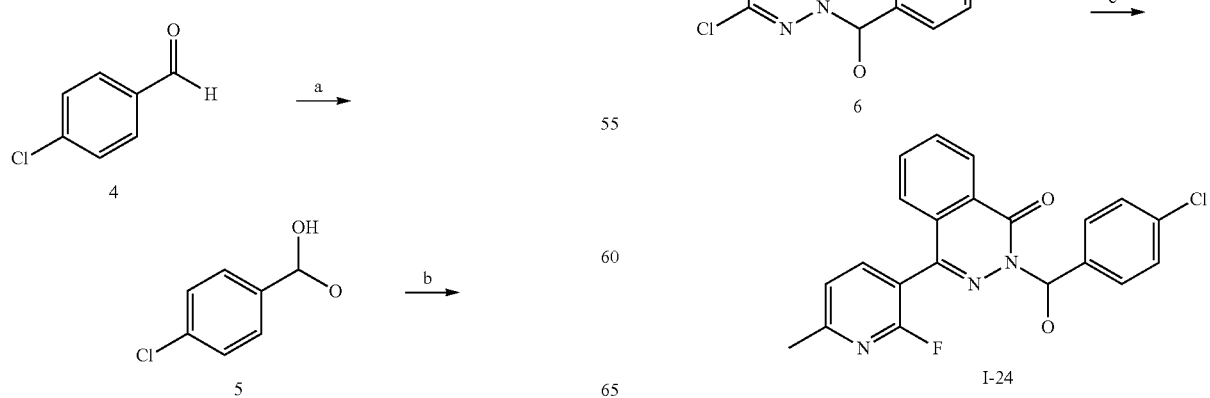

Step a:

p-chlorobenzaldehyde (1 g, 7.1 mmol) was dissolved in anhydrous methanol (50 ml), added with NaBD$_4$ (360 mg, 8.5 mmol), stirred at room temperature for 1 hour, and then rotary evaporated to remove the solvent. The residue was dissolved in ethyl acetate (100 ml) and water (100 ml), and the organic layer was washed with water (100 ml×4) and saturated brine (100 ml) in this order, dried over anhydrous sodium sulfate for half an hour and then concentrated to obtain a crude product. The crude product was separated and purified by column chromatography to obtain a white solid 5 (0.9 g, 90%).

Step b:

Compound 5 (500 mg, 3.5 mmol) was dissolved in toluene (20 ml), added with triethylamine (2 ml, 14 mmol) and methanesulfonyl chloride (0.32 ml, 4.2 mmol) in this order, stirred at room temperature for 2 hours, and then rotary evaporated to remove the solvent. The residue was dissolved in ethyl acetate (100 ml) and water (100 ml), and the organic layer was washed with water (100 ml×4) and saturated brine (100 ml) in this order, dried over anhydrous sodium sulfate for half an hour and then concentrated to obtain a crude product.

The above crude product (500 mg, 2.3 mmol) was dissolved in DMF (40 ml), and 6-chlorophthalazinone (compound 2) (407 mg, 2.3 mmol) and Cs$_2$CO$_3$ (750 mg, 2.3 mmol) were added in this order. After the reaction system was stirred at 50° C. for 5 hours, the reaction was completed as monitored by TLC. Ethyl acetate (100 ml) and water (100 ml) were added to the reaction solution, and the organic layer was washed with water (100 ml×4) and saturated brine (100 ml) in this order, dried over anhydrous sodium sulfate for half an hour, and concentrated to obtain a crude product. The crude product was separated and purified by column chromatography to obtain a white solid 6 (490 mg, 70%).

Step c:

Compound 6 (100 mg, 0.33 mmol) was dissolved in a mixed solvent of 1,4-dioxane (20 ml) and water (5 ml), and then 2-fluoro-6-methylpyridine-3-boronic acid (52.9 mg, 0.43 mmol), Pd(PPh$_3$)$_4$ (76.0 mg, 0.033 mmol), and K$_3$PO$_4$ (139 mg, 0.66 mmol) were added in this order. After the reaction system was purged with N$_2$ for 3 times, the reaction was performed at 100° C. overnight. Next day, after the reaction was completed as monitored by TLC, the reaction system was cooled to room temperature. After removing the solvent by rotary evaporation under reduced pressure, the residue was extracted and dissolved with ethyl acetate (30 ml). The organic layer was washed with water (30 ml×3) and saturated brine (30 ml) in this order, dried over anhydrous sodium sulfate, and concentrated to give a crude product. The crude product was separated and purified by column chromatography to obtain product I-24 (84 mg, 75%). $^1$H NMR (400 MHz, CDCl$_3$) δ 8.56-8.47 (m, 1H), 7.80 (tdd, J=8.9, 8.3, 4.5 Hz, 3H), 7.47 (dd, J=9.0, 2.6 Hz, 3H), 7.31 (d, J=8.4 Hz, 2H), 7.26 (dd, J=7.5, 1.5 Hz, 1H), 5.41 (s, 1H), 2.65 (s, 3H).

The following compounds were prepared in the same method as that in Example 2:

| Compounds | Preparation methods and structures of the products |
|---|---|
| I-25 | 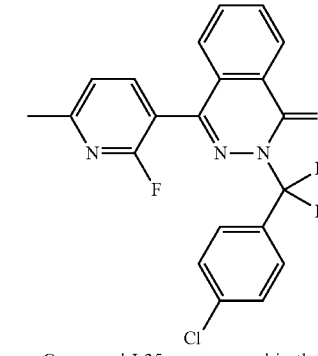<br>Compound I-25 was prepared in the same method as that in Example 2, except that methyl p-chlorobenzoate was used in place of p-chlorobenzaldehyde, and LiAlD$_4$ was used in place of NaBD$_4$.<br>(White crystal, yield 54%)<br>$^1$H NMR (400 MHz, CDCl$_3$) δ 8.50 (d, J = 7.3 Hz, 1H), 7.85-7.71 (m, 3H), 7.45 (d, J = 8.4 Hz, 3H), . 7.32-7.27 (m, 2H), 7.22 (s, 1H), 2.63 (s, 3H) |
| I-26 | 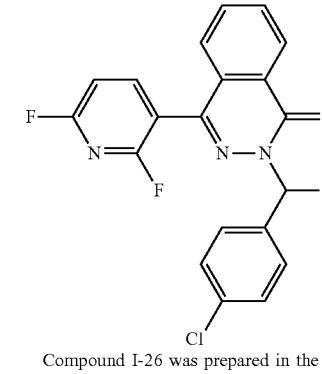<br>Compound I-26 was prepared in the same method as that in Example 2, except that 2,6-difluoropyridine-3-boronic acid was used in place of 2-fluoro-6-methylpyridine-3-boronic acid.<br>(White crystal, yield 58%)<br>$^1$H NMR (400 MHz, CDCl$_3$) δ 8.59-8.51 (m, 1H), 8.05 (dt, J = 8.8, 8.0 Hz, 1H), 7.88-7.74 (m, 2H), 7.49-7.42 (m, 3H), 7.35-7.31 (m, 2H), 7.06 (dd, J = 8.0, 2.8 Hz, 1H), 5.41 (s, 1H). |
| I-27 | 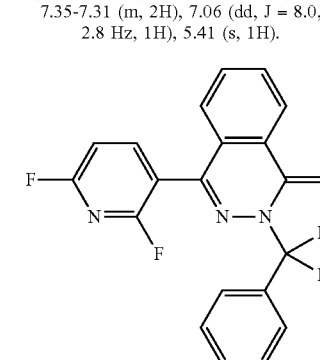<br>Compound I-27 was prepared in the same method as that in Example 2, except that 2,6-difluoropyridine-3-boronic acid was used in place of 2-fluoro-6-methylpyridine-3-boronic acid, methyl p-chlorobenzoate was used in place of p-chlorobenzaldehyde, and LiAlD$_4$ |

| Compounds | Preparation methods and structures of the products |
|---|---|
| | was used in place of NaBD$_4$.<br>(White crystal, yield 61%)<br>$^1$H NMR (400 MHz, CDCl$_3$) δ 8.56-8.50 (m, 1H), 8.05 (dd, J = 16.6, 7.8 Hz, 1H), 7.87-7.78 (m, 2H), 7.48-7.42 (m, 3H), 7.36-7.31 (m, 2H), 7.06 (dd, J = 7.9, 2.6 Hz, 1H). |
| IV-17 | 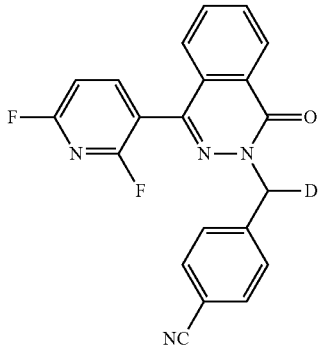 [SMILES: [2H]C(c1ccc(C#N)cc1)n1nc(-c2ccc(F)nc2F)c2ccccc2c1=O]<br>Compound IV-17 was prepared in the same method as that in Example 2, except that p-cyanobenzaldehyde was used in place of p-chlorobenzaldehyde, and 2,6-difluoropyridine-3-boronic acid was used in place of 2-fluoro-6-methylpyridine-3-boronic acid.<br>(White crystal, yield 66%)<br>$^1$H NMR (300 MHz, CDCl$_3$) δ 9.07 (s, 1H), 7.85 (d, J = 5.0 Hz, 3H), 7.65 (d, J = 5.0 Hz, 2H), 7.58 (s, 1H), 7.51 (d, J = 8.7 Hz, 3H), 5.68 (s, 1H). |
| IV-18 | 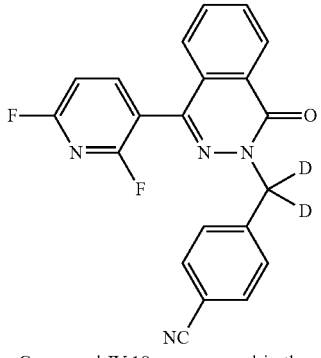<br>Compound IV-18 was prepared in the same method as that in Example 2, except that methyl p-cyanobenzoate was used in place of p-chlorobenzaldehyde, LiAlD$_4$ was used in place of NaBD$_4$, and 2,6-difluoropyridine-3-boronic acid was used in place of 2-fluoro-6-methylpyridine-3-boronic acid.<br>(White crystal, yield 59%)<br>$^1$H NMR (300 MHz, CDCl$_3$) δ 9.07 (s, 1H), 7.85 (d, J = 5.0 Hz, 3H), 7.65 (d, J = 5.0 Hz, 2H), 7.58 (s, 1H), 7.51 (d, J = 10.7 Hz, 3H). |

Example 3

The Scheme for Synthesizing Compound V-1 is Shown as Below:

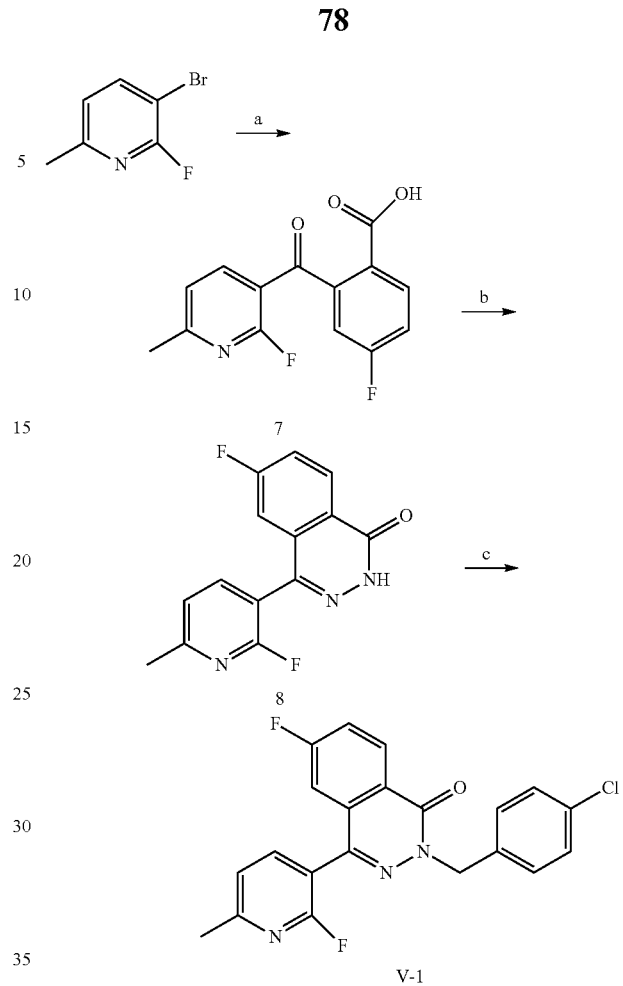

Step a:

2-fluoro-3-bromo-6-methylpyridine (500 mg, 2.6 mmol) was dissolved in anhydrous THF (50 ml), magnesium strips (126 mg, 5.2 mmol) was added thereto. The reaction system was purged with N$_2$ for 3 times, and stirred at room temperature for 1 hour, and then a solution of 4-fluorophthalic anhydride (474 mg, 2.8 mmol) in THF was added and reacted at room temperature overnight. The solvent was rotary evaporated in the next day. The residue was dissolved in ethyl acetate (100 ml) and water (100 ml). The organic layer was washed with water (100 ml×4) and saturated brine (100 ml) in this order, dried over anhydrous sodium sulfate for half an hour, and then concentrated to obtain a crude product. The crude product was separated and purified by column chromatography to obtain a white solid 7 (0.6 g, 80%).

Step b:

Compound 7 (0.6 g, 2.1 mmol) was dissolved in absolute ethanol (30 ml), added with 85% hydrazine hydrate (79 μl), and refluxed for 5 hours. The solvent was rotary evaporated to obtain a crude product 8 (384 mg, 67%).

Step c:

The above crude product (300 mg, 1.1 mmol) was dissolved in DMF (40 ml), and the halide (1.3 mmol) and Cs$_2$CO$_3$ (429 mg, 1.3 mmol) were added in this order. After the reaction system was stirred at 50° C. for 5 hours, the reaction was completed as monitored by TLC. Ethyl acetate (100 ml) and water (100 ml) were added to the reaction solution, and the organic layer was washed with water (100 ml×4) and saturated brine (100 ml) in this order, dried over anhydrous sodium sulfate for half an hour, and concentrated to obtain a crude product. The crude product was separated and purified by column chromatography to obtain a white crystal V-1 (327 mg, 75%). $^1$H NMR (500 MHz, CDCl$_3$) δ 8.66 (s, 1H), 7.98 (s, 1H), 7.82 (s, 1H), 7.54 (s, 1H), 7.47 (s, 1H), 7.35 (d, J=35.0 Hz, 4H), 4.87 (s, 2H), 2.68 (s, 3H).

The following compounds were prepared in the same method as that in Example 3:

| Compounds | Preparation methods and structures of the products |
|---|---|
| V-2 | 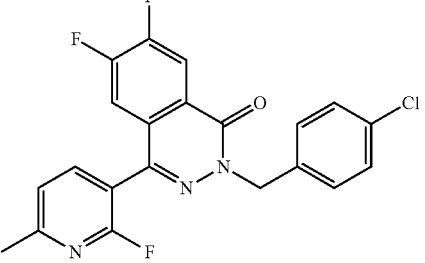<br>Compound V-2 was prepared in the same method as in Example 3, except that 4,5-difluorophthalic anhydride was used in place of 4-fluorophthalic anhydride.<br>(White crystal, yield 74%)<br>$^1$H NMR (400 MHz, CDCl$_3$) δ 8.66 (s, 1H), 8.14 (s, 1H), 7.96 (s, 1H), 7.47 (s, 1H), 7.36 (d, J = 35.0 Hz, 4H), 4.87 (s, 2H), 2.68 (s, 3H). |
| V-3 | 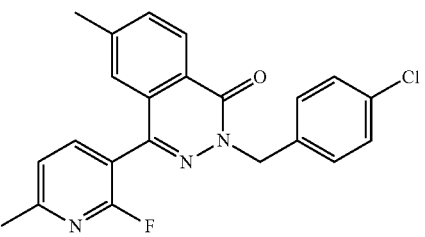 [SMILES: Cc1ccc2c(=O)n(Cc3ccc(Cl)cc3)nc(-c3ccc(C)nc3F)c2c1]<br>Compound V-3 was prepared in the same method as in Example 3, except that 4-methylphthalic anhydride was used in place of 4-fluorophthalic anhydride.<br>(White crystal, 71% yield)<br>$^1$H NMR (400 MHz, CDCl$_3$) δ 8.66 (s, 1H), 7.92 (s, 1H), 7.79 (s, 1H), 7.46 (d, J = 10.0 Hz, 2H), 7.36 (d, J = 35.0 Hz, 4H), 4.87 (s, 2H), 2.68 (s, 3H), 2.42 (s, 3H). |
| V-4 | 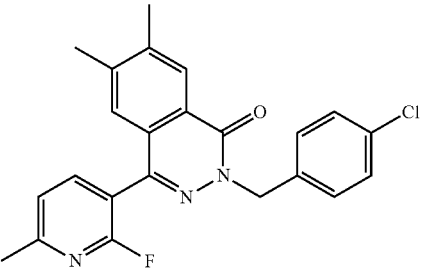 [SMILES: Cc1ccc(-c2nn(Cc3ccc(Cl)cc3)c(=O)c3cc(C)c(C)cc23)c(F)n1]<br>Compound V-4 was prepared in the same method as in Example 3, except that 4,5-dimethylphthalic anhydride was used in place of 4-fluorophthalic anhydride.<br>(White crystal, yield 64%)<br>$^1$H NMR (400 MHz, CDCl$_3$) δ 8.66 (s, 1H), 8.05 (s, 1H), 7.87 (s, 1H), 7.47 (s, 1H), 7.36 (d, J = 35.0 Hz, 4H), 4.87 (s, 2H), 2.68 (s, 3H), 2.31 (s, 6H). |
| V-5 | 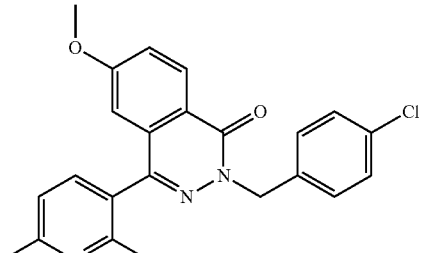<br>Compound V-5 was prepared in the same method as that in Example 3, except that 4-methoxyphthalic anhydride was used in place of 4-fluorophthalic anhydride.<br>(White crystal, yield 69%)<br>$^1$H NMR (300 MHz, CDCl$_3$) δ 8.66 (s, 1H), 7.84 (s, 1H), 7.58 (s, 1H), 7.47 (s, 1H), 7.36 (d, J = 35.0 Hz, 4H), 7.23 (s, 1H), 4.87 (s, 2H), 3.77 (s, 3H), 2.68 (s, 3H). |
| V-6 | 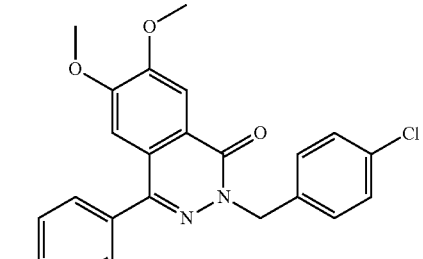<br>Compound V-6 was prepared in the same method as in Example 3, except that 4,5-dimethoxyphthalic anhydride was used in place of 4-fluorophthalic anhydride.<br>(White crystal, yield 80%)<br>$^1$H NMR (400 MHz, CDCl$_3$) δ 8.66 (s, 1H), 7.76 (s, 1H), 7.58 (s, 1H), 7.47 (s, 1H), 7.36 (d, J = 35.0 Hz, 4H), 4.87 (s, 2H), 3.85 (s, 6H), 2.68 (s, 3H). |
| V-7 | 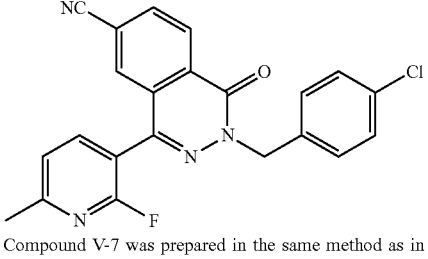<br>Compound V-7 was prepared in the same method as in Example 3, except that 4-cyanophthalic anhydride was used in place of 4-fluorophthalic anhydride.<br>(White crystal, yield 51%)<br>$^1$H NMR (400 MHz, CDCl$_3$) δ 8.66 (s, 1H), 8.02 (s, 1H), 7.85 (s, 1H), 7.59 (s, 1H), 7.47 (s, 1H), 7.36 (d, J = 35.0 Hz, 4H), 4.87 (s, 2H), 2.68 (s, 3H). |

-continued

| Compounds | Preparation methods and structures of the products |
|---|---|
| V-8 | 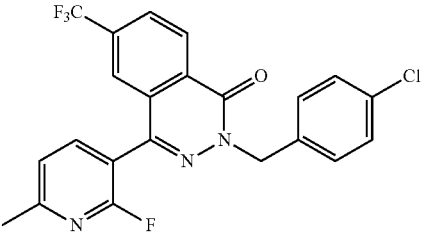 [SMILES: Cc1ccc(-c2nn(Cc3ccc(Cl)cc3)c(=O)c3ccc(C(F)(F)F)cc23)c(F)n1]<br>Compound V-8 was prepared in the same method as in Example 3, except that 4-trifluoromethylphthalic anhydride was used in place of 4-fluorophthalic anhydride. (White crystal, yield 45%)<br>$^1$H NMR (400 MHz, CDCl$_3$) δ 8.66 (s, 1H), 8.23 (s, 1H), 7.77 (s, 1H), 7.63 (s, 1H), 7.47 (s, 1H), 7.36 (d, J = 35.0 Hz, 4H), 4.87 (s, 2H), 2.68 (s, 3H). |
| V-9 | 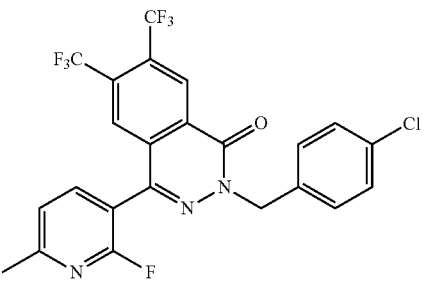 [SMILES: Cc1ccc(-c2nn(Cc3ccc(Cl)cc3)c(=O)c3cc(C(F)(F)F)c(C(F)(F)F)cc23)c(F)n1]<br>Compound V-9 was prepared in the same method as that in Example 3, except that 4,5-di-trifluoromethylphthalic anhydride was used in place of 4-fluorophthalic anhydride. (White crystal, yield 37%)<br>$^1$H NMR (400 MHz, CDCl$_3$) δ 8.87 (s, 1H), 8.66 (s, 1H), 7.84 (s, 1H), 7.47 (s, 1H), 7.35 (d, J = 35.0 Hz, 4H), 4.87 (s, 2H), 2.68 (s, 3H). |
| V-10 | 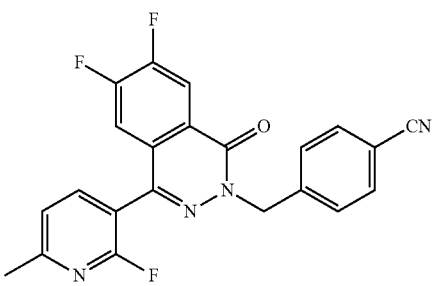 [SMILES: Cc1ccc(-c2nn(Cc3ccc(C#N)cc3)c(=O)c3cc(F)c(F)cc23)c(F)n1]<br>Compound V-10 was prepared in the same method as in Example 3, except that 4,5-difluorophthalic anhydride was used in place of 4-fluorophthalic anhydride and p-cyanobenzyl chloride was used in place of p-chlorobenzyl chloride. (White crystal, yield 75%)<br>$^1$H NMR (400 MHz, CDCl$_3$) δ 8.66 (s, 1H), 8.14 (s, 1H), 7.96 (s, 1H), 7.85 (s, 2H), 7.52 (s, 2H), 7.47 (s, 1H), 4.87 (s, 2H), 2.68 (s, 3H). |

| Compounds | Preparation methods and structures of the products |
|---|---|
| V-11 | 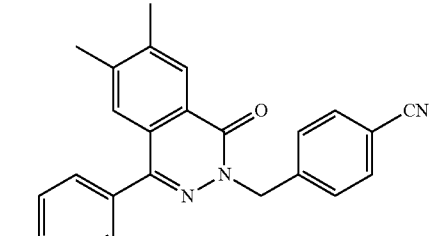<br>Compound V-11 was prepared in the same method as in Example 3, except that 4,5-dimethylphthalic anhydride was used in place of 4-fluorophthalic anhydride and p-cyanobenzyl chloride was used in place of p-chlorobenzyl chloride. (White crystal, yield 60%)<br>$^1$H NMR (400 MHz, CDCl$_3$) δ 8.66 (s, 1H), 8.05 (s, 1H), 7.86 (d, J = 10.0 Hz, 3H), 7.52 (s, 2H), 7.47 (s, 1H), 4.87 (s, 2H), 2.68 (s, 3H), 2.31 (s, 6H). |
| V-12 | 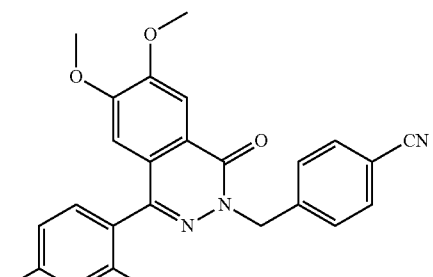<br>Compound V-12 was prepared in the same method as that in Example 3, except that 4,5-dimethoxyphthalic anhydride was used in place of 4-fluorophthalic anhydride, and p-cyanobenzyl chloride was used in place of p-chlorobenzyl chloride. (White crystal, yield 69%)<br>$^1$H NMR (400 MHz, CDCl$_3$) δ 8.66 (s, 1H), 7.85 (s, 2H), 7.76 (s, 1H), 7.58 (s, 1H), 7.49 (d, J = 25.0 Hz, 3H), 4.87 (s, 2H), 3.85 (s, 6H), 2.68 (s, 3H). |

Example 4

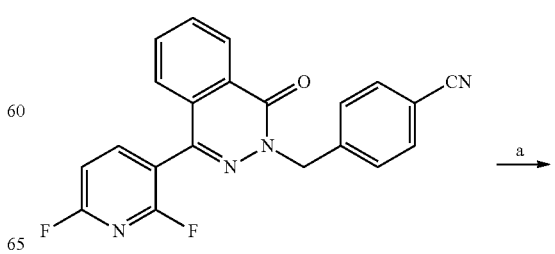

IV-5

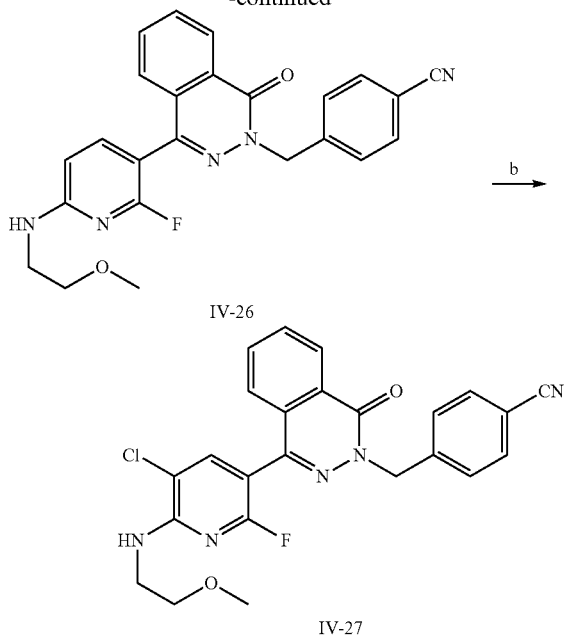

Step a:

Compound IV-5 (150 mg, 0.4 mmol) was dissolved in absolute ethanol (10 ml), added with 2-methoxyethylamine (0.35 ml, 4 mmol), and refluxed overnight. The solvent was rotary evaporated in the next day, and the residue was dissolved in ethyl acetate (50 ml) and water (50 ml). The organic layer was washed with saturated brine (50 ml), dried over anhydrous sodium sulfate for half an hour and concentrated to obtain a crude product. The crude product was separated and purified by column chromatography to obtain a white solid IV-26 (0.9 g, 52%), $^1$H NMR (400 MHz, Chloroform-d) δ 8.52-8.47 (m, 1H), 7.83-7.76 (m, 2H), 7.67-7.52 (m, 7H), 6.43 (dd, J=8.2, 1.8 Hz, 1H), 5.49 (s, 2H), 5.26 (d, J=6.1 Hz, 1H), 3.72-3.53 (m, 4H), 3.43 (s, 3H).

Step b:

Compound IV-26 (80 mg, 0.19 mmol) was dissolved in anhydrous acetonitrile (10 ml), added with N-chlorosuccinimide (25 mg, 0.19 mmol), and refluxed for 5 hours. The solvent was rotary evaporated to obtain a crude product. The crude product was separated and purified by column chromatography to obtain a white solid IV-27 (73 mg, 85%). $^1$H NMR (400 MHz, Chloroform-d) δ 8.52-8.45 (m, 1H), 7.85-7.77 (m, 2H), 7.66-7.61 (m, 3H), 7.59-7.56 (m, 3H), 5.71 (t, J=5.4 Hz, 1H), 5.47 (s, 2H), 3.76-3.69 (m, 2H), 3.63 (dd, J=5.3, 4.2 Hz, 2H), 3.44 (s, 3H).

| Compounds | Preparation methods and structures of the products |
|---|---|
| IV-28 | 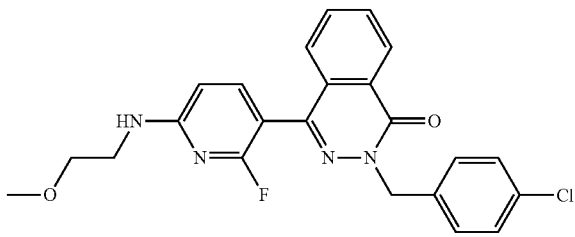 [SMILES: COCCNc1ccc(-c2nn(Cc3ccc(Cl)cc3)c(=O)c3ccccc23)c(F)n1]<br>The above compound was prepared in the same method as that in Example 4, except that 4-chlorobenzyl chloride was used in place of 4-cyanobenzyl chloride. (White crystal, yield 70%)<br>$^1$H NMR (400 MHz, Chloroform-d) δ 8.54-8.47 (m, 1H), 7.83-7.74 (m, 2H), 7.64-7.55 (m, 2H), 7.50-7.42 (m, 2H), 7.31 (d, J = 8.4 Hz, 2H), 6.42 (dd, J = 8.2, 1.8 Hz, 1H), 5.42 (s, 2H), 5.21 (s, 1H), 3.62 (pd, J = 6.2, 1.9 Hz, 4H), 3.44 (s, 3H). |
| IV-29 | 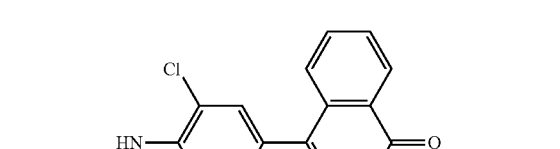<br>The above compound was prepared in the same method as that in Example 4, except that 4-chlorobenzyl chloride was used in place of 4-cyanobenzyl chloride. (White crystal, yield 85%)<br>$^1$H NMR (400 MHz, Chloroform-d) δ 8.53-8.48 (m, 1H), 7.83-7.76 (m, 2H), 7.67 (d, J = 7.9 Hz, 1H), 7.57 (dq, J = 7.2, 3.3 Hz, 1H), 7.49-7.44 (m, 2H), 7.35-7.29 (m, 2H), 5.71 (t, J = 5.1 Hz, 1H), 5.41 (s, 2H), 3.74 (q, J = 5.1 Hz, 2H), 3.65 (t, J = 5.0 Hz, 2H), 3.45 (s, 3H). |

| Compounds | Preparation methods and structures of the products |
|---|---|
| IV-30 | 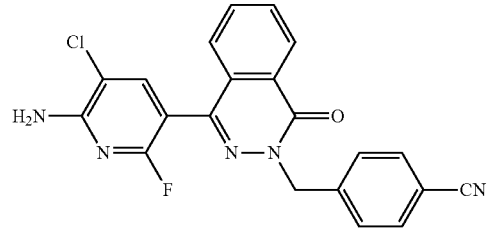 [SMILES: N#Cc1ccc(Cn2nc(-c3cc(Cl)c(N)nc3F)c3ccccc3c2=O)cc1]<br>The above compound was prepared in the same method as that in Example 4, except that ammonia gas was used in place of 2-methoxyethylamine. (White crystal, yield 81%)<br>$^1$H NMR (400 MHz, Chloroform-d) δ 8.52-8.46 (m, 1H), 7.85-7.78 (m, 2H), 7.70 (d, J = 7.9 Hz, 1H), 7.65-7.61 (m, 2H), 7.59-7.50 (m, 3H), 5.47 (s, 2H), 5.22 (s, 2H). |
| IV-31 | 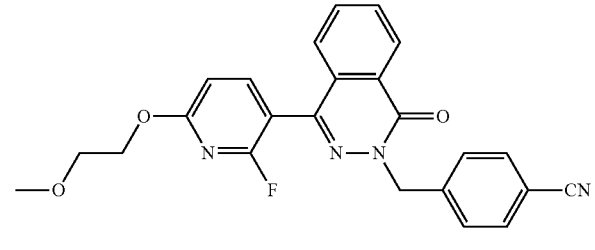 [SMILES: COCCOc1ccc(-c2nn(Cc3ccc(C#N)cc3)c(=O)c3ccccc23)c(F)n1]<br>The above compound was prepared in the same method as that in Example 4, except that 2-methoxyethanol was used in place of 2-methoxyethylamine. (White crystal, yield 56%)<br>$^1$H NMR (400 MHz, Chloroform-d) δ 8.55-8.49 (m, 1H), 7.91-7.76 (m, 3H), 7.65 (d, J = 8.5 Hz, 2H), 7.59 (d, J = 8.3 Hz, 2H), 7.54-7.49 (m, 1H), 6.89 (dd, J = 8.2, 1.1 Hz, 1H), 5.50 (s, 2H), 4.61-4.51 (m, 2H), 3.85-3.78 (m, 2H), 3.49 (s, 3H). |
| IV-32 | 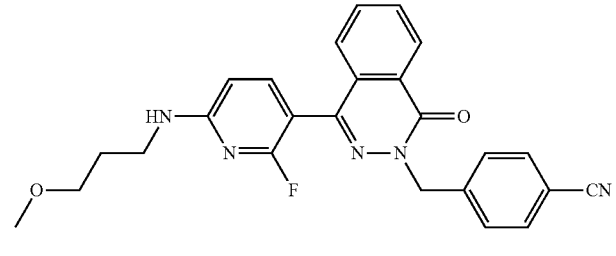<br>The above compound was prepared in the same method as that in Example 4, except that 3-methoxypropylamine was used in place of 2-methoxyethylamine. (White crystal, yield 61%)<br>$^1$H NMR (400 MHz, Chloroform-d) δ 8.66-8.39 (m, 1H), 7.86-7.73 (m, 2H), 7.72-7.47 (m, 6H), 6.39 (d, J = 8.5 Hz, 1H), 5.50 (s, 2H), 5.35 (s, 1H), 3.57 (t, J = 5.7 Hz, 2H), 3.50 (q, J = 6.2 Hz, 2H), 3.40 (d, J = 1.6 Hz, 3H), 1.95 (p, J = 6.2 Hz, 2H). |
| IV-33 | 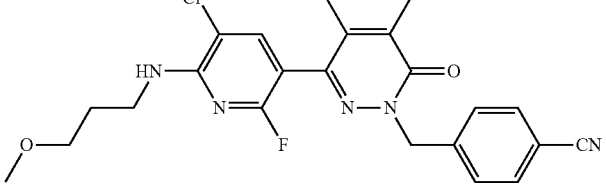<br>The above compound was prepared in the same method as that in Example 4, except that 3-methoxypropylamine was used in place of 2-methoxyethylamine. (White crystal, yield 86%)<br>$^1$H NMR (400 MHz, Chloroform-d) δ 8.54-8.47 (m, 1H), 7.85-7.78 (m, 2H), 7.67-7.62 (m, 3H), 7.59 (d, J = 8.4 Hz, 2H), 6.14 (t, J = 5.2 Hz, 1H), 5.49 (s, 2H), 3.72-3.53 (m, 4H), 3.43 (s, 3H), 2.05-1.86 (m, 2H). |

| Compounds | Preparation methods and structures of the products |
|---|---|
| IV-34 | 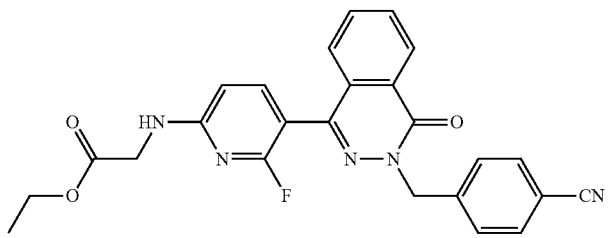 [SMILES: CCOC(=O)CNc1ccc(-c2nn(Cc3ccc(C#N)cc3)c(=O)c3ccccc23)c(F)n1]<br>The above compound was prepared in the same method as that in Example 4, except that glycine ethyl ester was used in place of 2-methoxyethylamine. (White crystal, yield 67%)<br>$^1$H NMR (400 MHz, Chloroform-d) δ 8.53-8.49 (m, 1H), 7.85-7.77 (m, 2H), 7.68-7.56 (m, 6H), 6.50 (dd, J = 8.2, 1.7 Hz, 1H), 5.49 (s, 2H), 5.35 (t, J = 5.3 Hz, 1H), 4.30 (q, J = 7.1 Hz, 2H), 4.22 (d, J = 5.2 Hz, 2H), 1.35 (t, J = 7.1 Hz, 3H). |
| IV-35 | 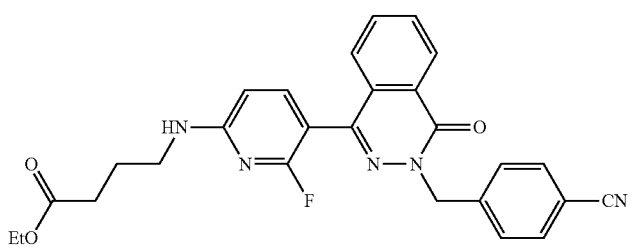 [SMILES: CCOC(=O)CCCNc1ccc(-c2nn(Cc3ccc(C#N)cc3)c(=O)c3ccccc23)c(F)n1]<br>The above compound was prepared in the same method as that in Example 4, except that ethyl 4-aminobutyrate was used in place of 2-methoxyethylamine. (White crystal, yield 79%)<br>$^1$H NMR (400 MHz, Chloroform-d) δ 8.53-8.48 (m, 1H), 7.85-7.77 (m, 2H), 7.67-7.57 (m, 6H), 6.41 (dd, J = 8.2, 1.9 Hz, 1H), 5.50 (s, 2H), 5.07 (t, J = 5.9 Hz, 1H), 4.19 (q, J = 7.1 Hz, 2H), 3.46 (q, J = 6.7 Hz, 2H), 2.47 (t, J = 7.1 Hz, 2H), 2.02 (p, J = 7.0 Hz, 2H), 1.30 (t, J = 7.1 Hz, 3H). |
| IV-36 | 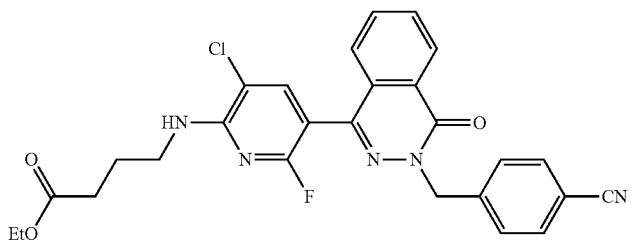 [SMILES: CCOC(=O)CCCNc1nc(F)c(-c2nn(Cc3ccc(C#N)cc3)c(=O)c3ccccc23)cc1Cl]<br>The above compound was prepared in the same method as that in Example 4, except that ethyl 4-aminobutyrate was used in place of 2-methoxyethylamine. (White crystal, yield 81%)<br>$^1$H NMR (400 MHz, Chloroform-d) δ 8.50-8.48 (m, 1H), 7.86-7.79 (m, 2H), 7.69-7.56 (m, 6H), 5.58 (s, 1H), 5.49 (s, 2H), 4.23-4.15 (m, 2H), 3.67-3.54 (m, 2H), 2.48 (t, J = 7.1 Hz, 2H), 2.06 (d, J = 5.3 Hz, 2H), 1.30 (t, J = 7.1 Hz, 3H). |
| IV-37 | 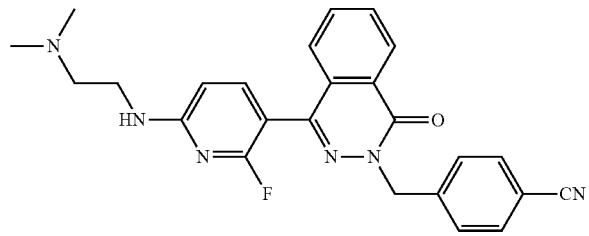 [SMILES: CN(C)CCNc1ccc(-c2nn(Cc3ccc(C#N)cc3)c(=O)c3ccccc23)c(F)n1]<br>The above compound was prepared in the same method as that in Example 4, except that N,N-dimethylethylenediamine was used in place of 2-methoxyethylamine. (White crystal, yield 59%)<br>$^1$H NMR (400 MHz, Chloroform-d) δ 8.54-8.46 (m, 1H), 7.86-7.75 (m, 2H), 7.67-7.53 (m, 6H), 6.50 (dd, J = 8.3, 1.9 Hz, 1H), 6.01 (s, 1H), 5.49 (s, 2H), 3.58 (q, J = 5.4 Hz, 2H), 2.81 (t, J = 5.7 Hz, 2H), 2.48 (s, 6H). |

| Compounds | Preparation methods and structures of the products |
|---|---|
| IV-38 | 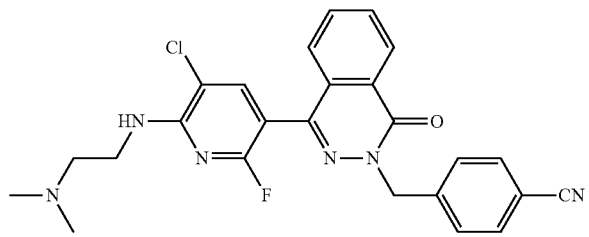 [SMILES: CN(C)CCNc1nc(F)c(-c2nn(Cc3ccc(C#N)cc3)c(=O)c3ccccc23)cc1Cl]<br>The above compound was prepared in the same method as that in Example 4, except that N,N-dimethylethylenediamine was used in place of 2-methoxyethylamine. (White crystal, 71% yield)<br>$^1$H NMR (400 MHz, Chloroform-d) δ 8.50 (t, J = 4.7 Hz, 1H), 7.82 (dd, J = 6.3, 3.0 Hz, 2H), 7.72-7.53 (m, 6H), 6.04 (s, 1H), 5.49 (s, 2H), 3.57 (q, J = 5.7 Hz, 2H), 2.62 (t, J = 6.0 Hz, 2H), 2.34 (s, 6H). |
| IV-39 | 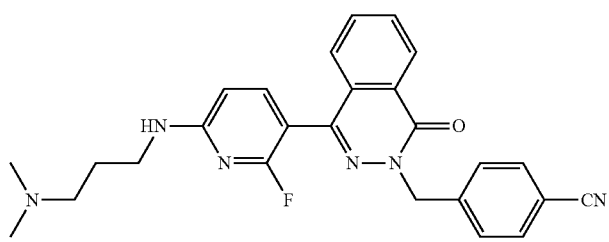 [SMILES: CN(C)CCCNc1ccc(-c2nn(Cc3ccc(C#N)cc3)c(=O)c3ccccc23)c(F)n1]<br>The above compound was prepared in the same method as that in Example 4, except that N,N-dimethylpropanediamine was used in place of 2-methoxyethylamine. (White crystal, yield 57%)<br>$^1$H NMR (400 MHz, Chloroform-d) δ 8.52-8.43 (m, 1H), 7.82-7.73 (m, 2H), 7.60 (q, J = 8.5 Hz, 6H), 6.37 (dd, J = 8.2, 1.9 Hz, 1H), 6.19 (d, J = 5.5 Hz, 1H), 5.48 (s, 2H), 3.45 (q, J = 6.0 Hz, 2H), 2.48 (t, J = 6.5 Hz, 2H), 2.29 (s, 6H), 1.84 (q, J = 6.4 Hz, 2H). |
| IV-40 | 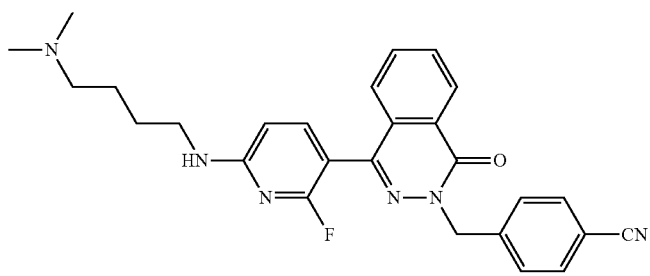 [SMILES: CN(C)CCCCNc1ccc(-c2nn(Cc3ccc(C#N)cc3)c(=O)c3ccccc23)c(F)n1]<br>The above compound was prepared in the same method as that in Example 4, except that N,N-dimethylbutanediamine was used in place of 2-methoxyethylamine. (White crystal, yield 67%)<br>$^1$H NMR (400 MHz, Chloroform-d) δ 8.51-8.45 (m, 1H), 7.81-7.76 (m, 2H), 7.68-7.51 (m, 6H), 6.33 (dd, J = 8.2, 1.9 Hz, 1H), 5.83 (s, 1H), 5.48 (s, 2H), 3.36 (d, J = 5.7 Hz, 2H), 2.34 (t, J = 6.9 Hz, 2H), 2.26 (s, 6H), 1.78-1.58 (m, 4H). |
| IV-41 | 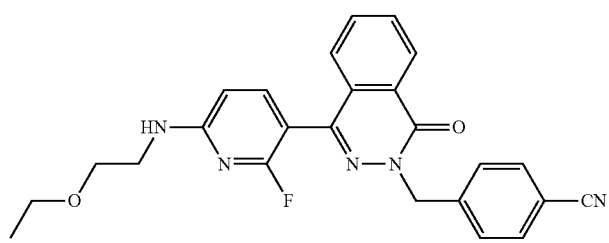 [SMILES: CCOCCNc1ccc(-c2nn(Cc3ccc(C#N)cc3)c(=O)c3ccccc23)c(F)n1]<br>The above compound was prepared in the same method as that in Example 4, except that 2-ethoxyethylamine was used in place of 2-methoxyethylamine. (White crystal, yield 69%)<br>$^1$H NMR (400 MHz, Chloroform-d) δ 8.51-8.46 (m, 1H), 7.81-7.76 |

| Compounds | Preparation methods and structures of the products |
|---|---|
| | (m, 2H), 7.64-7.55 (m, 6H), 6.41 (dd, J = 8.2, 1.9 Hz, 1H), 5.48 (s, 2H), 5.23 (t, J = 5.5 Hz, 1H), 3.66 (dd, J = 5.5, 4.4 Hz, 2H), 3.61-3.53 (m, 4H), 1.25 (t, J = 7.0 Hz, 3H). |
| IV-42 | 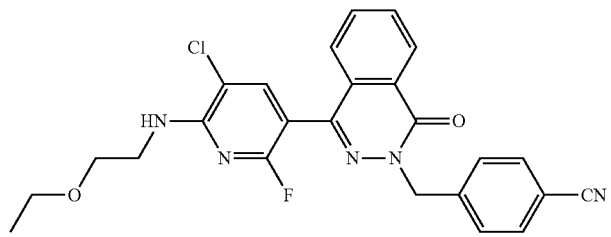 [SMILES: CCOCCNc1nc(F)c(-c2nn(Cc3ccc(C#N)cc3)c(=O)c3ccccc23)cc1Cl]<br>The above compound was prepared in the same method as that in Example 4, except that 2-ethoxyethylamine was used in place of 2-methoxyethylamine. (White crystal, yield 86%)<br>$^1$H NMR (400 MHz, Chloroform-d) δ 8.51-8.46 (m, 1H), 7.84-7.76 (m, 2H), 7.68-7.52 (m, 6H), 5.75 (t, J = 5.3 Hz, 1H), 5.47 (s, 2H), 3.77-3.64 (m, 4H), 3.58 (q, J = 7.0 Hz, 2H), 1.26 (t, J = 7.0 Hz, 3H). |
| IV-43 | 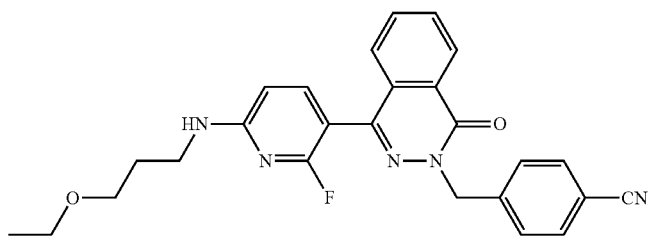 [SMILES: CCOCCCNc1ccc(-c2nn(Cc3ccc(C#N)cc3)c(=O)c3ccccc23)c(F)n1]<br>The above compound was prepared in the same method as that in Example 4, except that 3-ethoxypropylamine was used in place of 2-methoxyethylamine. (White crystal, yield 68%)<br>$^1$H NMR (400 MHz, Chloroform-d) δ 8.50-8.46 (m, 1H), 7.81-7.75 (m, 2H), 7.65-7.51 (m, 6H), 6.36 (dd, J = 8.3, 1.9 Hz, 1H), 5.48 (s, 2H), 5.37 (s, 1H), 3.59 (t, J = 5.7 Hz, IV-442H), 3.54-3.44 (m, 4H), 1.93 (p, J = 6.0 Hz, 2H), 1.21 (t, J = 7.1 Hz, 3H). |
| IV-44 | 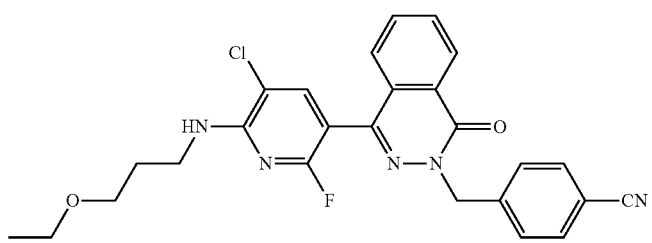 [SMILES: CCOCCCNc1nc(F)c(-c2nn(Cc3ccc(C#N)cc3)c(=O)c3ccccc23)cc1Cl]<br>The above compound was prepared in the same method as that in Example 4, except that 3-ethoxypropylamine was used in place of 2-methoxyethylamine. (White crystal, yield 88%)<br>$^1$H NMR (400 MHz, Chloroform-d) δ 8.51-8.45 (m, 1H), 7.82-7.77 (m, 2H), 7.65-7.55 (m, 6H), 6.30 (t, J = 5.1 Hz, 1H), 5.47 (s, 2H), 3.64 (dt, J = 9.1, 5.5 Hz, 4H), 3.55 (q, J = 7.0 Hz, 2H), 2.01-1.92 (m, 2H), 1.27 (t, J = 7.0 Hz, 3H). |
| IV-45 | 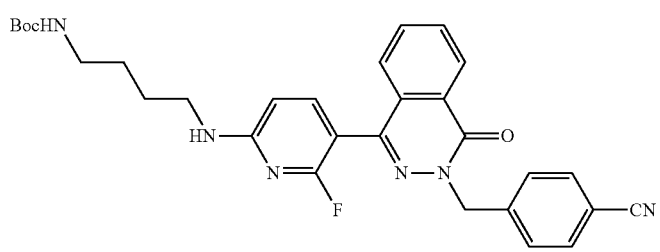 [SMILES: CC(C)(C)OC(=O)NCCCCNc1ccc(-c2nn(Cc3ccc(C#N)cc3)c(=O)c3ccccc23)c(F)n1]<br>The above compound was prepared in the same method as that in Example 4, except that 4-t-butoxycarbonylbutanediamine was used in place of 2-methoxyethylamine. (White crystal, yield 75%) |

| Compounds | Preparation methods and structures of the products |
|---|---|
| | ¹H NMR (400 MHz, Chloroform-d) δ 8.51-8.45 (m, 1H), 7.83-7.74 (m, 2H), 7.65-7.54 (m, 6H), 6.38 (dd, J = 8.2, 1.8 Hz, 1H), 5.48 (s, 2H), 3.40 (q, J = 6.5 Hz, 2H), 3.20 (q, J = 6.6 Hz, 2H), 1.74-1.65 (m, 2H), 1.60 (d, J = 7.5 Hz, 2H), 1.45 (s, 9H). |
| IV-46 | 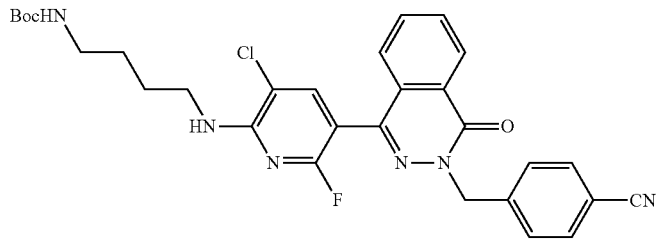 [SMILES: CC(C)(C)OC(=O)NCCCCNc1nc(F)c(-c2nn(Cc3ccc(C#N)cc3)c(=O)c3ccccc23)cc1Cl]<br>The above compound was prepared in the same method as that in Example 4, except that 4-t-butoxycarbonylbutanediamine was used in place of 2-methoxyethylamine. (White crystal, yield 81%)<br>¹H NMR (400 MHz, Chloroform-d) δ 8.52-8.45 (m, 1H), 7.84-7.75 (m, 2H), 7.67-7.53 (m, 6H), 5.47 (s, 2H), 5.40 (s, 1H), 4.64 (s, 1H), 3.55 (td, J = 7.0, 5.8 Hz, 2H), 3.21 (q, J = 6.7 Hz, 2H), 1.73 (ddd, J = 8.7, 7.5, 5.3 Hz, 2H), 1.64-1.57 (m, 2H), 1.45 (s, 9H). |
| IV-47 | 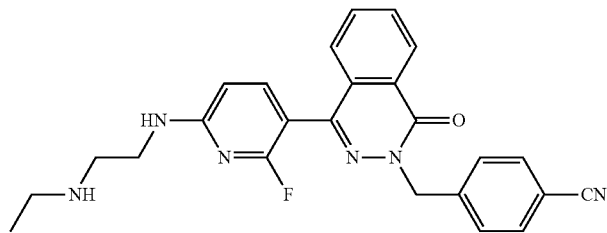 [SMILES: CCNCCNc1nc(F)c(-c2nn(Cc3ccc(C#N)cc3)c(=O)c3ccccc23)cc1Cl]<br>The above compound was prepared in the same method as that in Example 4, except that 2-ethylethylenediamine was used in place of 2-methoxyethylamine. (White crystal, yield 61%)<br>¹H NMR (400 MHz, Chloroform-d) δ 8.54-8.46 (m, 1H), 7.84-7.75 (m, 2H), 7.66-7.54 (m, 6H), 6.45 (dd, J = 8.2, 1.9 Hz, 1H), 5.69 (t, J = 5.4 Hz, 1H), 5.49 (s, 2H), 3.53 (q, J = 5.6 Hz, 2H), 2.98 (dd, J = 6.3, 5.2 Hz, 2H), 2.77 (q, J = 7.1 Hz, 2H), 1.19 (t, J = 7.2 Hz, 3H). |
| IV-48 | 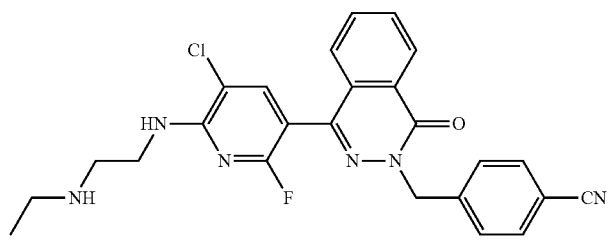<br>The above compound was prepared in the same method as that in Example 4, except that 2-ethylethylenediamine was used in place of 2-methoxyethylamine. (White crystal, yield 74%)<br>¹H NMR (400 MHz, Chloroform-d) δ 8.53-8.49 (m, 1H), 7.85-7.79 (m, 2H), 7.71-7.62 (m, 3H), 7.58 (d, J = 8.3 Hz, 3H), 6.93 (s, 1H), 5.48 (s, 2H), 4.04 (d, J = 5.2 Hz, 2H), 3.36-3.28 (m, 2H), 3.14 (q, J = 7.2 Hz, 2H), 1.51 (t, J = 7.2 Hz, 3H). |

| Compounds | Preparation methods and structures of the products |
|---|---|
| IV-49 | 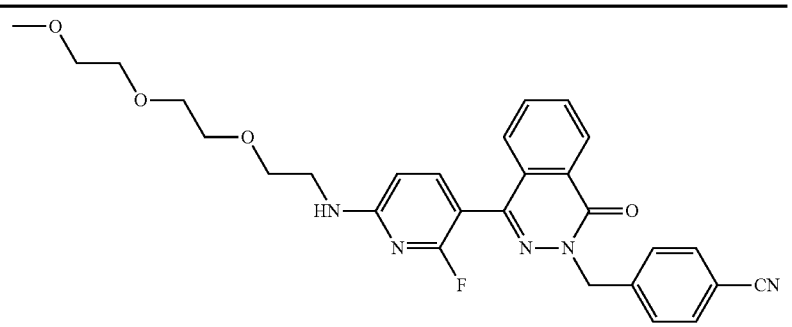

The above compound was prepared in the same method as that in Example 4, except that 2-(2-(2-methoxyethoxy)ethoxy)ethyl-1-amine was used in place of 2-methoxyethylamine. (White crystal, yield 76%)
$^1$H NMR (400 MHz, Chloroform-d) δ 8.50-8.46 (m, 1H), 7.80-7.77 (m, 2H), 7.63-7.56 (m, 6H), 6.43 (dd, J = 8.2, 1.8 Hz, 1H), 5.57 (t, J = 5.6 Hz, 1H), 5.48 (s, 2H), 3.75-3.66 (m, 8H), 3.62-3.57 (m, 4H), 3.41 (s, 3H). |
| IV-50 | 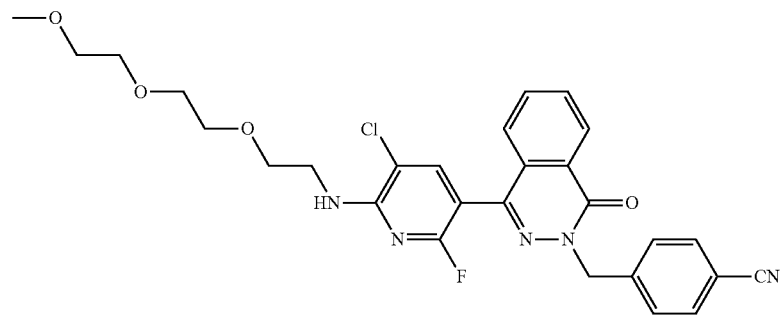 [SMILES: COCCOCCOCCNc1nc(F)c(-c2nn(Cc3ccc(C#N)cc3)c(=O)c3ccccc23)cc1Cl]

The above compound was prepared in the same method as that in Example 4, except that 2-(2-(2-methoxyethoxy)ethoxy)ethyl-1-amine was used in place of 2-methoxyethylamine. (White crystal, yield 84%)
$^1$H NMR (400 MHz, Chloroform-d) δ 8.51-8.46 (m, 1H), 7.83-7.77 (m, 2H), 7.66-7.55 (m, 6H), 5.84 (s, 1H), 5.47 (s, 2H), 3.75-3.66 (m, 10H), 3.60-3.56 (m, 2H), 3.40 (s, 3H). |
| IV-51 | 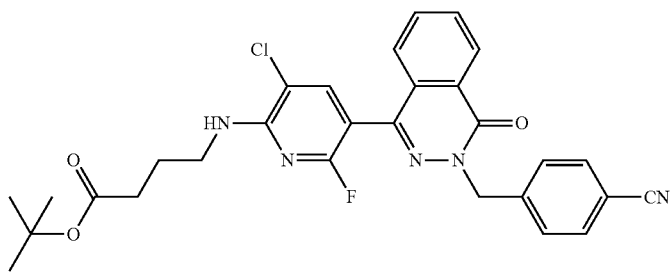 [SMILES: CC(C)(C)OC(=O)CCCNc1nc(F)c(-c2nn(Cc3ccc(C#N)cc3)c(=O)c3ccccc23)cc1Cl]

The above compound was prepared in the same method as that in Example 4, except that t-butyl 4-aminobutyrate was used in place of 2-methoxyethylamine. (White crystal, yield 83%)
$^1$H NMR (400 MHz, Chloroform-d) δ 8.52-8.45 (m, 1H), 7.84-7.76 (m, 2H), 7.68-7.55 (m, 6H), 5.63 (t, J = 5.7 Hz, 1H), 5.47 (s, 2H), 3.57 (td, J = 6.8, 5.6 Hz, 2H), 2.38 (t, J = 7.1 Hz, 2H), 1.99 (p, J = 7.0 Hz, 2H), 1.48 (d, J = 1.2 Hz, 9H). |
| IV-52 | 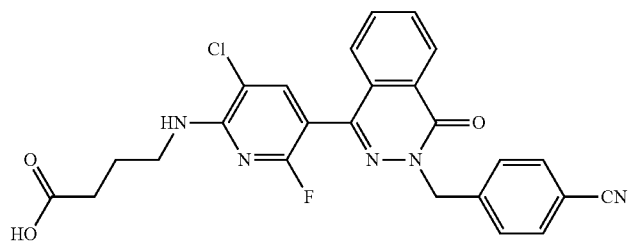 [SMILES: N#Cc1ccc(Cn2nc(-c3cc(Cl)c(NCCCC(=O)O)nc3F)c3ccccc3c2=O)cc1] |

| Compounds | Preparation methods and structures of the products |
|---|---|
| | The above compound was prepared in the same method as that in Example 4, except that 4-aminobutyric acid was used in place of 2-methoxyethylamine. (White crystal, 71% yield)<br>¹H NMR (400 MHz, Chloroform-d) δ 8.53-8.46 (m, 1H), 7.80 (dd, J = 6.2, 3.2 Hz, 2H), 7.66-7.55 (m, 6H), 5.56 (d, J = 5.8 Hz, 1H), 5.47 (s, 2H), 3.61 (q, J = 6.5 Hz, 2H), 2.53 (t, J = 7.1 Hz, 2H), 2.08-2.03 (m, 2H). |
| IV-53 | 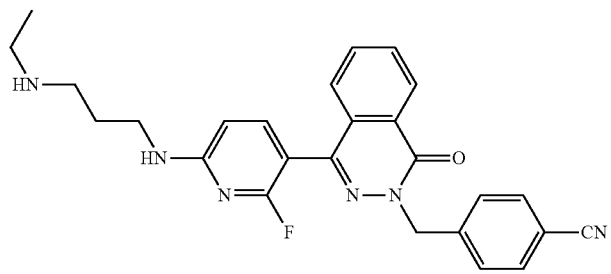 [SMILES: CCNCCCNc1ccc(-c2nn(Cc3ccc(C#N)cc3)c(=O)c3ccccc23)c(F)n1]<br>The above compound was prepared in the same method as that in Example 4, except that N-ethylpropanediamine was used in place of 2-methoxyethylamine. (White crystal, yield 58%)<br>¹H NMR (400 MHz, Chloroform-d) δ 8.53-8.44 (m, 1H), 7.84-7.73 (m, 2H), 7.64-7.53 (m, 6H), 6.39 (dd, J = 8.2, 1.9 Hz, 1H), 6.07 (s, 1H), 5.48 (s, 2H), 3.55-3.46 (m, 2H), 2.87 (t, J = 6.4 Hz, 2H), 2.77 (q, J = 7.2 Hz, 2H), 1.92 (p, J = 6.4 Hz, 2H), 1.22 (t, J = 7.2 Hz, 3H). |
| IV-54 | 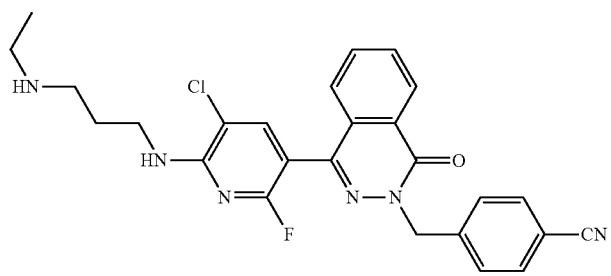 [SMILES: CCNCCCNc1nc(F)c(-c2nn(Cc3ccc(C#N)cc3)c(=O)c3ccccc23)cc1Cl]<br>The above compound was prepared in the same method as that in Example 4, except that N-ethylpropanediamine was used in place of 2-methoxyethylamine. (White crystal, yield 82%)<br>¹H NMR (400 MHz, Chloroform-d) δ 8.55-8.46 (m, 1H), 7.86-7.78 (m, 2H), 7.70-7.55 (m, 6H), 6.26 (t, J = 6.1 Hz, 1H), 5.48 (s, 2H), 3.80-3.72 (m, 2H), 3.11 (q, J = 7.0 Hz, 4H), 2.26 (t, J = 6.5 Hz, 2H), 1.48 (t, J = 7.2 Hz, 3H). |
| IV-55 | 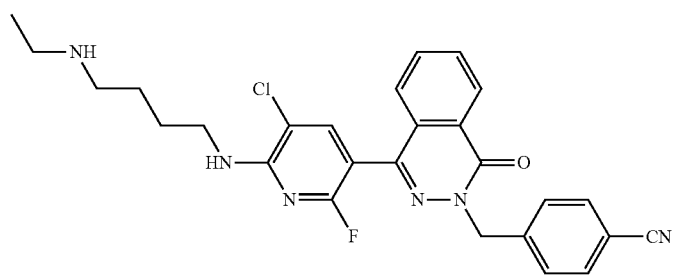 [SMILES: CCNCCCCNc1nc(F)c(-c2nn(Cc3ccc(C#N)cc3)c(=O)c3ccccc23)cc1Cl]<br>The above compound was prepared in the same method as that in Example 4, except that N-ethylbutanediamine was used in place of 2-methoxyethylamine. (White crystal, 71% yield)<br>¹H NMR (400 MHz, Chloroform-d) δ 8.51-8.44 (m, 1H), 7.82-7.76 (m, 2H), 7.65-7.53 (m, 6H), 5.57 (t, J = 5.9 Hz, 1H), 5.46 (s, 2H), 3.54 (q, J = 6.4 Hz, 2H), 3.05 (q, J = 7.1 Hz, 4H), 1.84 (ddq, J = 35.4, 14.5, 7.1 Hz, 4H), 1.35 (t, J = 7.3 Hz, 3H). |

| Compounds | Preparation methods and structures of the products |
|---|---|
| IV-56 | 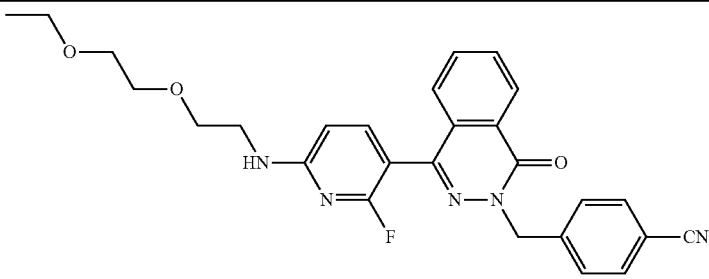<br>The above compound was prepared in the same method as that in Example 4, except that 2-(2-ethoxyethoxy)ethyl-1-amine was used in place of 2-methoxyethylamine. (White crystal, yield 64%)<br>¹H NMR (400 MHz, Chloroform-d) δ 8.53-8.47 (m, 1H), 7.84-7.77 (m, 2H), 7.66-7.54 (m, 6H), 6.42 (dd, J = 8.2, 1.8 Hz, 1H), 5.49 (s, 2H), 5.43 (t, J = 5.5 Hz, 1H), 3.75 (dd, J = 5.6, 4.5 Hz, 2H), 3.72-3.68 (m, 2H), 3.66-3.61 (m, 4H), 3.61-3.55 (m, 2H), 1.27 (t, J = 7.0 Hz, 3H). |
| IV-57 | 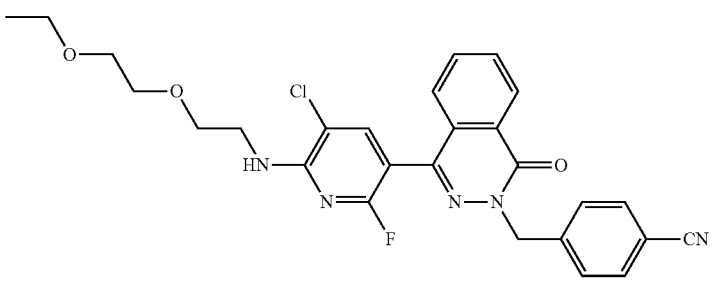 [SMILES: CCOCCOCCNc1nc(F)c(-c2nn(Cc3ccc(C#N)cc3)c(=O)c3ccccc23)cc1Cl]<br>The above compound was prepared in the same method as that in Example 4, except that 2-(2-ethoxyethoxy)ethyl-1-amine was used in place of 2-methoxyethylamine. (White crystal, yield 84%)<br>¹H NMR (400 MHz, Chloroform-d) δ 7.84-7.76 (m, 2H), 7.67-7.52 (m, 6H), 5.81 (s, 1H), 5.47 (s, 2H), 3.74 (d, J = 2.7 Hz, 4H), 3.71-3.67 (m, 2H), 3.64 (dt, J = 6.1, 2.1 Hz, 2H), 3.57 (q, J = 7.0 Hz, 2H), 1.24 (t, J = 7.0 Hz, 3H). |
| IV-58 | 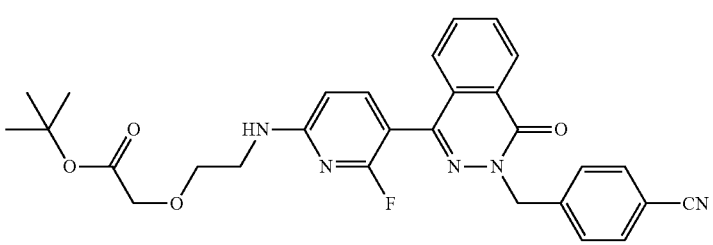 [SMILES: CC(C)(C)OC(=O)COCCNc1ccc(-c2nn(Cc3ccc(C#N)cc3)c(=O)c3ccccc23)c(F)n1]<br>The above compound was prepared in the same method as that in Example 4, except that t-butyl 2-(2-aminoethoxy)acetate was used in place of 2-methoxyethylamine. (White crystal, yield 67%)<br>¹H NMR (400 MHz, Chloroform-d) δ 8.53-8.48 (m, 1H), 7.83-7.78 (m, 2H), 7.66-7.54 (m, 6H), 6.47 (dd, J = 8.3, 1.9 Hz, 1H), 5.81 (d, J = 5.2 Hz, 1H), 5.50 (s, 2H), 4.06 (s, 2H), 3.80 (dd, J = 5.5, 4.5 Hz, 2H), 3.64 (q, J = 5.1 Hz, 2H), 1.53 (s, 9H). |
| IV-59 | 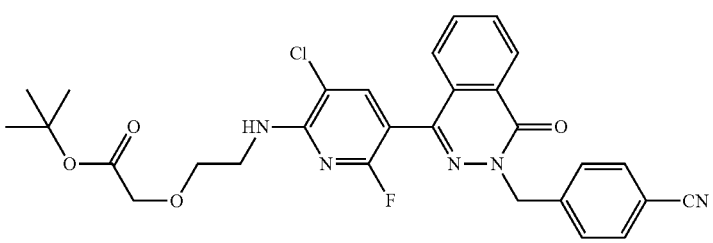 [SMILES: CC(C)(C)OC(=O)COCCNc1nc(F)c(-c2nn(Cc3ccc(C#N)cc3)c(=O)c3ccccc23)cc1Cl]<br>The above compound was prepared in the same method as that in Example 4, except that t-butyl 2-(2-aminoethoxy)acetate was used in |

| Compounds | Preparation methods and structures of the products |
|---|---|
| | place of 2-methoxyethylamine. (White crystal, yield 86%)<br>¹H NMR (400 MHz, Chloroform-d) δ 7.84-7.80 (m, 2H), 7.68-7.63 (m, 3H), 7.60 (d, J = 8.4 Hz, 3H), 6.24 (s, 1H), 5.49 (s, 2H), 4.07 (s, 2H), 3.83 (dd, J = 5.5, 4.3 Hz, 2H), 3.76 (t, J = 5.1 Hz, 2H), 1.53 (s, 9H). |
| IV-60 | 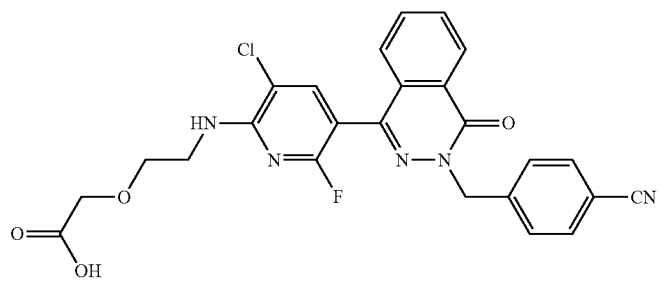 [SMILES: N#Cc1ccc(Cn2nc(-c3cc(Cl)c(NCCOCC(=O)O)nc3F)c3ccccc3c2=O)cc1]<br>The above compound was prepared in the same method as that in Example 4, except that 2-(2-aminoethoxy)acetic acid was used in place of 2-methoxyethylamine. (White crystal, yield 73%)<br>¹H NMR (400 MHz, DMSO-d6) δ 8.33 (dd, J = 7.3, 2.2 Hz, 1H), 7.93 (dq, J = 6.0, 3.6, 2.7 Hz, 3H), 7.84-7.76 (m, 2H), 7.62 (d, J = 6.9 Hz, 1H), 7.51 (d, J = 7.9 Hz, 2H), 7.28 (s, 1H), 5.45 (s, 2H), 3.66 (t, J = 5.7 Hz, 2H), 3.53 (d, J = 5.6 Hz, 2H). |
| IV-61 | 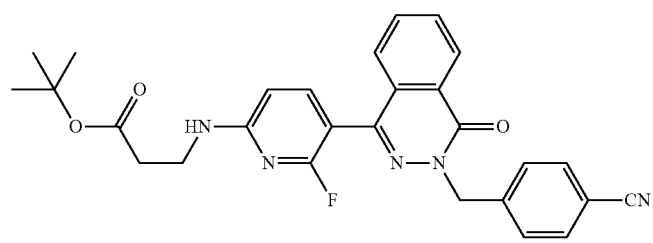 [SMILES: CC(C)(C)OC(=O)CCNc1ccc(-c2nn(Cc3ccc(C#N)cc3)c(=O)c3ccccc23)c(F)n1]<br>The above compound was prepared in the same method as that in Example 4, except that t-butyl 3-aminopropionate was used in place of 2-methoxyethylamine. (White crystal, yield 60%)<br>¹H NMR (400 MHz, Chloroform-d) δ 8.53-8.47 (m, 1H), 7.83-7.79 (m, 2H), 7.68-7.55 (m, 7H), 6.41 (dd, J = 8.2, 1.8 Hz, 1H), 5.50 (d, J = 2.9 Hz, 2H), 5.36 (t, J = 6.2 Hz, 1H), 3.69 (q, J = 6.1 Hz, 2H), 2.61 (t, J = 6.0 Hz, 2H), 1.50 (s, 9H). |
| IV-62 | 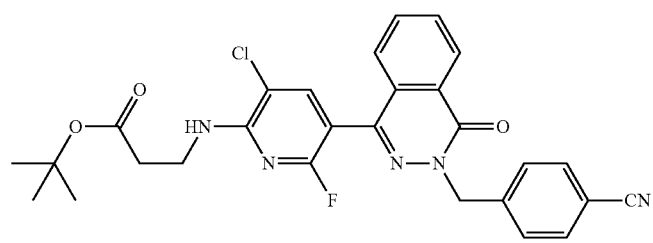 [SMILES: CC(C)(C)OC(=O)CCNc1nc(F)c(-c2nn(Cc3ccc(C#N)cc3)c(=O)c3ccccc23)cc1Cl]<br>The above compound was prepared in the same method as that in Example 4, except that t-butyl 3-aminopropionate was used in place of 2-methoxyethylamine. (White crystal, yield 75%)<br>¹H NMR (400 MHz, Chloroform-d) δ 8.50 (s, 1H), 7.82 (s, 2H), 7.70-7.55 (m, 6H), 5.95 (s, 1H), 5.49 (s, 2H), 3.81 (d, J = 6.0 Hz, 2H), 2.63 (t, J = 6.0 Hz, 2H), 1.52 (s, 9H). |
| IV-63 | 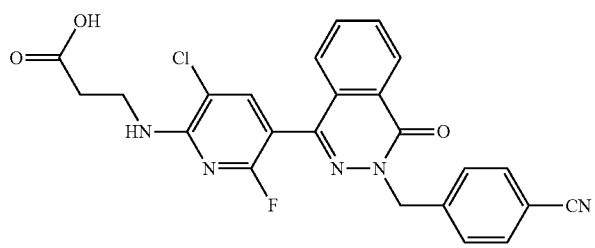 [SMILES: N#Cc1ccc(Cn2nc(-c3cc(Cl)c(NCCC(=O)O)nc3F)c3ccccc3c2=O)cc1] |

| Compounds | Preparation methods and structures of the products |
|---|---|
| | The above compound was prepared in the same method as that in Example 4, except that 3-aminopropionic acid was used in place of 2-methoxyethylamine. (White crystal, yield 76%)<br>¹H NMR (400 MHz, Chloroform-d) δ 8.53-8.46 (m, 1H), 7.80 (s, 2H), 7.68-7.60 (m, 3H), 7.57 (d, J = 7.9 Hz, 3H), 5.86 (s, 1H), 5.47 (s, 2H), 3.85 (q, J = 6.0 Hz, 2H), 2.80 (t, J = 6.0 Hz, 2H). |
| IV-64 | 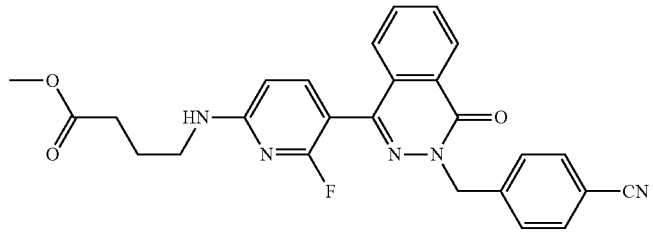 [SMILES: COC(=O)CCCNc1ccc(-c2nn(Cc3ccc(C#N)cc3)c(=O)c3ccccc23)c(F)n1] |
| | The above compound was prepared in the same method as that in Example 4, except that methyl 4-aminobutyrate was used in place of 2-methoxyethylamine. (White crystal, yield 59%)<br>¹H NMR (400 MHz, Chloroform-d) δ 8.51-8.45 (m, 1H), 7.83-7.74 (m, 2H), 7.64-7.54 (m, 6H), 6.40 (dd, J = 8.2, 1.9 Hz, 1H), 5.48 (s, 2H), 5.09 (t, J = 5.9 Hz, 1H), 3.71 (s, 3H), 3.44 (q, J = 6.6 Hz, 2H), 2.47 (t, J = 7.1 Hz, 2H), 2.00 (p, J = 7.0 Hz, 2H). |
| IV-65 | 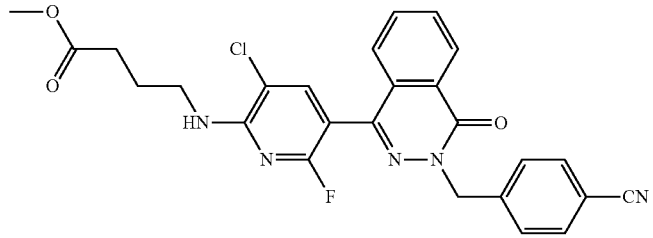 [SMILES: COC(=O)CCCNc1nc(F)c(-c2nn(Cc3ccc(C#N)cc3)c(=O)c3ccccc23)cc1Cl] |
| | The above compound was prepared in the same method as that in Example 4, except that methyl 4-aminobutyrate was used in place of 2-methoxyethylamine. (White crystal, yield 77%)<br>¹H NMR (400 MHz, Chloroform-d) δ 8.52-8.47 (m, 1H), 7.84-7.79 (m, 2H), 7.67-7.57 (m, 6H), 5.57 (t, J = 5.8 Hz, 1H), 5.49 (s, 2H), 3.73 (s, 3H), 3.60 (td, J = 6.8, 5.7 Hz, 2H), 2.49 (t, J = 7.1 Hz, 2H), 2.06 (p, J = 7.0 Hz, 2H). |
| IV-66 | 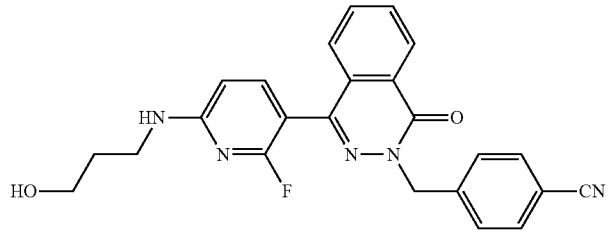 [SMILES: N#Cc1ccc(Cn2nc(-c3ccc(NCCCO)nc3F)c3ccccc3c2=O)cc1] |
| | The above compound was prepared in the same method as that in Example 4, except that 3-aminopropanol was used in place of 2-methoxyethylamine. (White crystal, yield 61%)<br>¹H NMR (400 MHz, Chloroform-d) δ 8.58-8.44 (m, 1H), 7.86-7.76 (m, 2H), 7.64 (d, J = 8.4 Hz, 2H), 7.62-7.56 (m, 5H), 6.42 (dd, J = 8.3, 1.8 Hz, 1H), 5.50 (s, 2H), 5.20 (t, J = 6.1 Hz, 1H), 3.81 (t, J = 5.6 Hz, 2H), 3.60 (q, J = 6.2 Hz, 2H), 2.59 (s, 1H), 1.94-1.86 (m, 2H). |
| IV-67 | 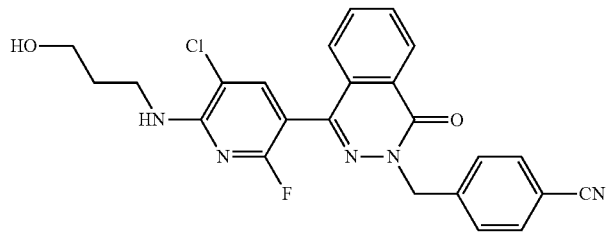 [SMILES: N#Cc1ccc(Cn2nc(-c3cc(Cl)c(NCCCO)nc3F)c3ccccc3c2=O)cc1] |

| Compounds | Preparation methods and structures of the products |
|---|---|
| | The above compound was prepared in the same method as that in Example 4, except that 3-aminopropanol was used in place of 2-methoxyethylamine. (White crystal, yield 81%)<br>$^1$H NMR (400 MHz, Chloroform-d) δ 8.53-8.46 (m, 1H), 7.85-7.78 (m, 2H), 7.68-7.51 (m, 6H), 5.87 (t, J = 5.9 Hz, 1H), 5.48 (s, 2H), 3.80 (t, J = 5.6 Hz, 2H), 3.69 (q, J = 6.1 Hz, 2H), 1.96-1.85 (m, 2H). |
| IV-68 | 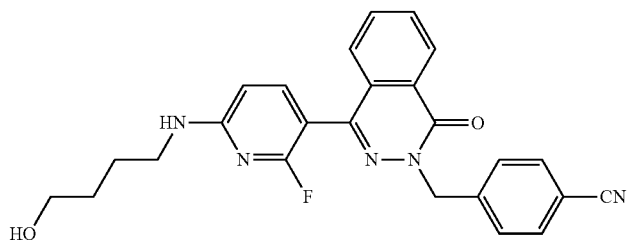 [SMILES: N#Cc1ccc(Cn2nc(-c3ccc(NCCCCO)nc3F)c3ccccc3c2=O)cc1] |
| | The above compound was prepared in the same method as that in Example 4, except that 4-aminobutanol was used in place of 2-methoxyethylamine. (White crystal, yield 70%)<br>$^1$H NMR (400 MHz, Chloroform-d) δ 8.52-8.43 (m, 1H), 7.83-7.74 (m, 2H), 7.69-7.49 (m, 6H), 6.36 (dd, J = 8.2, 1.9 Hz, 1H), 5.47 (s, 2H), 5.08 (t, J = 5.7 Hz, 1H), 3.73 (t, J = 6.1 Hz, 2H), 3.40 (q, J = 6.7 Hz, 2H), 1.80-1.66 (m, 4H). |
| IV-69 | 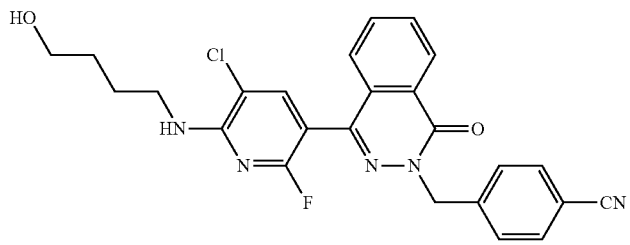 [SMILES: N#Cc1ccc(Cn2nc(-c3cc(Cl)c(NCCCCO)nc3F)c3ccccc3c2=O)cc1] |
| | The above compound was prepared in the same method as that in Example 4, except that 4-aminobutanol was used in place of 2-methoxyethylamine. (White crystal, yield 85%)<br>$^1$H NMR (400 MHz, Chloroform-d) δ 8.51-8.44 (m, 1H), 7.84-7.76 (m, 2H), 7.67-7.53 (m, 6H), 5.57 (t, J = 5.7 Hz, 1H), 5.47 (s, 2H), 3.75 (t, J = 6.1 Hz, 2H), 3.57 (td, J = 6.8, 5.6 Hz, 2H), 1.84-1.77 (m, 2H), 1.75-1.67 (m, 2H). |
| IV-70 | 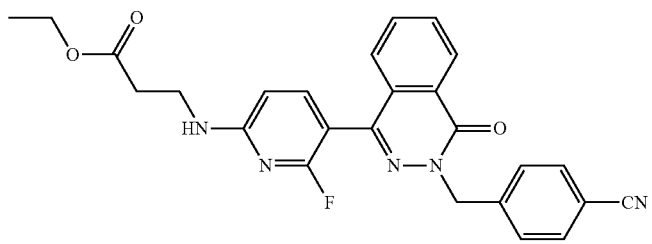 [SMILES: CCOC(=O)CCNc1ccc(-c2nn(Cc3ccc(C#N)cc3)c(=O)c3ccccc23)c(F)n1] |
| | The above compound was prepared in the same method as that in Example 4, except that ethyl 3-aminopropionate was used in place of 2-methoxyethylamine. (White crystal, yield 66%)<br>$^1$H NMR (400 MHz, Chloroform-d) δ 8.54-8.47 (m, 1H), 7.85-7.76 (m, 2H), 7.67-7.54 (m, 6H), 6.41 (dd, J = 8.2, 1.8 Hz, 1H), 5.49 (s, 2H), 5.36 (t, J = 6.3 Hz, 1H), 4.21 (q, J = 7.2 Hz, 2H), 3.74 (q, J = 6.1 Hz, 2H), 2.70 (t, J = 6.0 Hz, 2H), 1.31 (t, J = 7.1 Hz, 3H). |

| Compounds | Preparation methods and structures of the products |
|---|---|
| IV-71 | 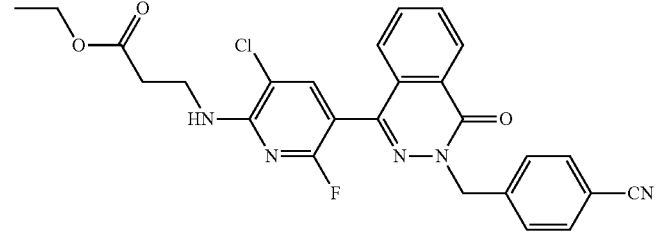 [SMILES: CCOC(=O)CCNc1nc(F)c(-c2nn(Cc3ccc(C#N)cc3)c(=O)c3ccccc23)cc1Cl]<br>The above compound was prepared in the same method as that in Example 4, except that ethyl 3-aminopropionate was used in place of 2-methoxyethylamine. (White crystal, yield 79%)<br>¹H NMR (400 MHz, Chloroform-d) δ 8.53-8.47 (m, 1H), 7.85-7.78 (m, 2H), 7.68-7.62 (m, 3H), 7.62-7.55 (m, 3H), 5.96 (t, J = 6.1 Hz, 1H), 5.48 (s, 2H), 4.22 (q, J = 7.1 Hz, 2H), 3.85 (q, J = 6.1 Hz, 2H), 2.72 (t, J = 6.0 Hz, 2H), 1.32 (t, J = 7.1 Hz, 3H). |
| IV-72 | 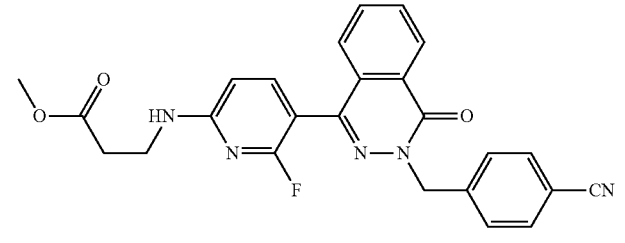 [SMILES: COC(=O)CCNc1ccc(-c2nn(Cc3ccc(C#N)cc3)c(=O)c3ccccc23)c(F)n1]<br>The above compound was prepared in the same method as that in Example 4, except that methyl 3-aminopropionate was used in place of 2-methoxyethylamine. (White crystal, yield 70%)<br>¹H NMR (400 MHz, Chloroform-d) δ 8.52-8.44 (m, 1H), 7.82-7.74 (m, 2H), 7.64-7.53 (m, 6H), 6.39 (dd, J = 8.2, 1.8 Hz, 1H), 5.47 (s, 2H), 5.30 (t, J = 6.1 Hz, 1H), 3.70-3.75 (m, 5H), 2.70 (t, J = 6.0 Hz, 2H). |
| IV-73 | 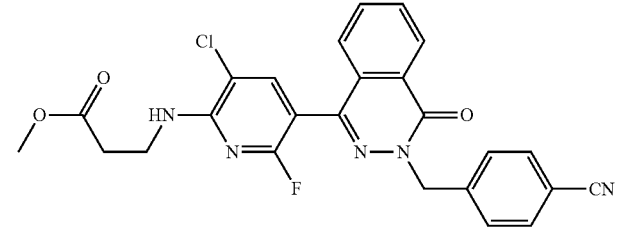 [SMILES: COC(=O)CCNc1nc(F)c(-c2nn(Cc3ccc(C#N)cc3)c(=O)c3ccccc23)cc1Cl]<br>The above compound was prepared in the same method as that in Example 4, except that methyl 3-aminopropionate was used in place of 2-methoxyethylamine. (White crystal, 78% yield)<br>¹H NMR (400 MHz, Chloroform-d) δ 8.52-8.45 (m, 1H), 7.83-7.77 (m, 2H), 7.66-7.55 (m, 6H), 5.91 (t, J = 6.2 Hz, 1H), 5.47 (s, 2H), 3.83 (q, J = 6.1 Hz, 2H), 3.75 (s, 3H), 2.73 (t, J = 6.0 Hz, 2H). |
| IV-74 | 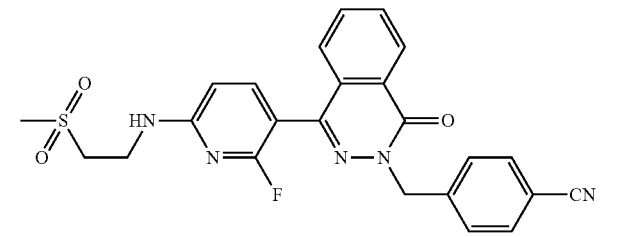 [SMILES: CS(=O)(=O)CCNc1ccc(-c2nn(Cc3ccc(C#N)cc3)c(=O)c3ccccc23)c(F)n1]<br>The above compound was prepared in the same method as that in Example 4, except that 2-aminoethyl sulfone was used in place of 2-methoxyethylamine. (White crystal, yield 67%)<br>¹H NMR (400 MHz, Chloroform-d) δ 8.55-8.48 (m, 1H), 7.84-7.78 (m, 2H), 7.67-7.56 (m, 6H), 6.50 (dd, J = 8.2, 1.6 Hz, 1H), 5.52 (d, J = 6.3 Hz, 1H), 5.50 (s, 2H), 4.04 (q, J = 6.0 Hz, 2H), 3.48-3.40 (m, 2H), 3.04 (s, 3H). |

| Compounds | Preparation methods and structures of the products |
|---|---|
| IV-75 | 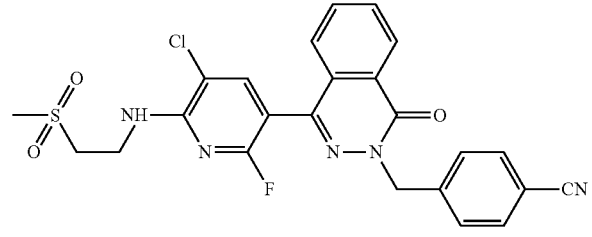 [SMILES: CS(=O)(=O)CCNc1nc(F)c(-c2nn(Cc3ccc(C#N)cc3)c(=O)c3ccccc23)cc1Cl]<br>The above compound was prepared in the same method as that in Example 4, except that 2-aminoethyl sulfone was used in place of 2-methoxyethylamine. (White crystal, yield 83%)<br>$^1$H NMR (400 MHz, Chloroform-d) δ 8.54-8.50 (m, 1H), 7.85-7.82 (m, 2H), 7.72 (d, J = 7.9 Hz, 1H), 7.67-7.63 (m, 2H), 7.62-7.55 (m, 3H), 6.03 (d, J = 6.1 Hz, 1H), 5.49 (s, 2H), 4.12 (q, J = 6.0 Hz, 2H), 3.47-3.42 (m, 2H), 3.05 (s, 3H). |
| IV-76 | 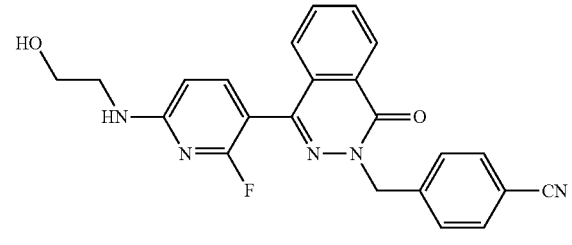 [SMILES: N#Cc1ccc(Cn2nc(-c3ccc(NCCO)nc3F)c3ccccc3c2=O)cc1]<br>The above compound was prepared in the same method as that in Example 4, except that 2-aminoethanol was used in place of 2-methoxyethylamine. (White crystal, yield 66%)<br>$^1$H NMR (400 MHz, Methanol-d4) δ 8.47-8.42 (m, 1H), 7.95-7.89 (m, 2H), 7.75-7.71 (m, 2H), 7.69-7.58 (m, 4H), 6.55 (dd, J = 8.3, 1.9 Hz, 1H), 5.53 (s, 2H), 3.76 (t, J = 5.8 Hz, 2H), 3.52 (t, J = 5.8 Hz, 2H). |
| IV-77 | 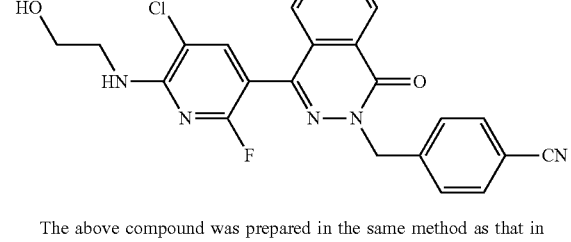<br>The above compound was prepared in the same method as that in Example 4, except that 2-aminoethanol was used in place of 2-methoxyethylamine. (White crystal, 78% yield)<br>$^1$H NMR (400 MHz, Chloroform-d) δ 8.53-8.49 (m, 1H), 7.87-7.80 (m, 2H), 7.74-7.49 (m, 6H), 5.76 (s, 1H), 5.49 (s, 3H), 3.94 (q, J = 5.1 Hz, 2H), 3.75 (q, J = 5.3 Hz, 2H). |
| IV-78 | 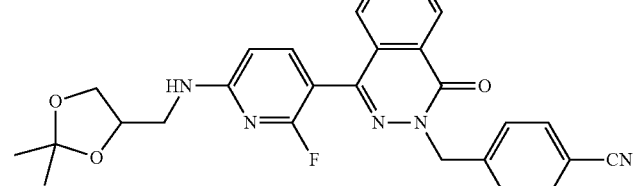<br>The above compound was prepared in the same method as that in Example 4, except that (2,2-dimethyl-[1,3]-dioxolane-4-yl)-methylamine was used in place of 2-methoxyethylamine. (White crystal, yield 69%)<br>$^1$H NMR (400 MHz, Chloroform-d) δ 8.54-8.48 (m, 1H), 7.84-7.77 (m, 2H), 7.67-7.55 (m, 6H), 6.45 (dd, J = 8.4, 1.7 Hz, 1H), 5.50 (s, 2H), 5.15 (t, J = 5.8 Hz, 1H), 4.15 (dd, J = 8.3, 6.5 Hz, 1H), 3.82-3.70 (m, 2H), 3.49 (dt, J = 13.9, 5.9 Hz, 1H), 1.41 (s, 3H). |

| Compounds | Preparation methods and structures of the products |
|---|---|
| IV-79 | 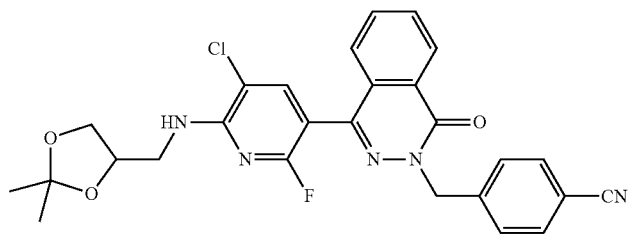 [SMILES: CC1(C)OCC(CNc2nc(F)c(-c3nn(Cc4ccc(C#N)cc4)c(=O)c4ccccc34)cc2Cl)O1]<br>The above compound was prepared in the same method as that in Example 4, except that (2,2-dimethyl-[1,3]-dioxolane-4-yl)-methylamine was used in place of 2-methoxyethylamine. (White crystal, yield 78%)<br>$^1$H NMR (400 MHz, Chloroform-d) δ 8.53-8.48 (m, 1H), 7.85-7.79 (m, 2H), 7.70-7.63 (m, 3H), 7.62-7.55 (m, 3H), 5.72 (t, J = 5.7 Hz, 1H), 5.49 (s, 2H), 4.45 (qd, J = 6.0, 3.5 Hz, 1H), 4.15 (dd, J = 8.6, 6.7 Hz, 1H), 3.82-3.75 (m, 2H), 3.69 (dt, J = 14.2, 5.9 Hz, 1H), 1.54 (s, 3H), 1.42 (s, 3H). |
| IV-80 | 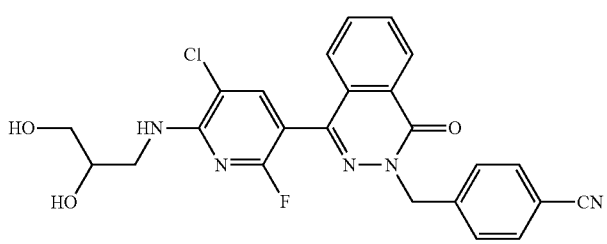 [SMILES: N#Cc1ccc(Cn2nc(-c3cc(Cl)c(NCC(O)CO)nc3F)c3ccccc3c2=O)cc1]<br>The above compound was prepared in the same method as that in Example 4, except that 3-amino-1,2-propanediol was used in place of 2-methoxyethylamine. (White crystal, yield 76%)<br>$^1$H NMR (400 MHz, Chloroform-d) δ 8.55-8.48 (m, 1H), 7.86-7.80 (m, 2H), 7.70 (d, J = 7.9 Hz, 1H), 7.67-7.63 (m, 2H), 7.61-7.54 (m, 3H), 5.79 (t, J = 6.0 Hz, 1H), 5.49 (s, 2H), 4.00 (p, J = 5.0 Hz, 1H), 3.82-3.75 (m, 2H), 3.71-3.60 (m, 2H). |
| IV-81 | 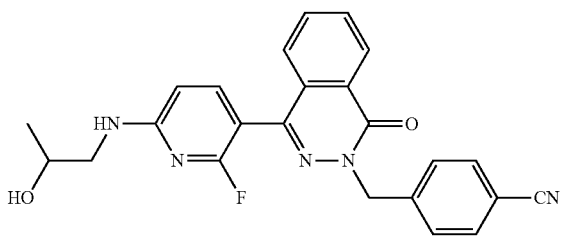 [SMILES: CC(O)CNc1ccc(-c2nn(Cc3ccc(C#N)cc3)c(=O)c3ccccc23)c(F)n1]<br>The above compound was prepared in the same method as that in Example 4, except that 1-amino-2-propanol was used in place of 2-methoxyethylamine. (White crystal, yield 61%)<br>$^1$H NMR (400 MHz, Chloroform-d) δ 8.53-8.48 (m, 1H), 7.84-7.77 (m, 2H), 7.68-7.56 (m, 6H), 6.45 (dd, J = 8.2, 1.6 Hz, 1H), 5.50 (s, 2H), 5.24 (s, 1H), 4.12 (s, 1H), 3.62 (ddd, J = 13.8, 6.6, 3.2 Hz, 1H), 3.31 (ddd, J = 13.4, 7.8, 5.2 Hz, 1H), 2.24 (d, J = 4.4 Hz, 1H), 1.32 (d, J = 6.3 Hz, 3H). |
| IV-82 | 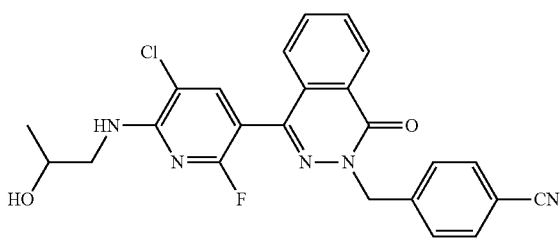<br>The above compound was prepared in the same method as that in Example 4, except that 1-amino-2-propanol was used in place of 2-methoxyethylamine. (White crystal, yield 79%)<br>$^1$H NMR (400 MHz, Chloroform-d) δ 8.54-8.49 (m, 1H), 7.85-7.79 (m, 2H), 7.70-7.63 (m, 3H), 7.59 (d, J = 8.1 Hz, 3H), 5.78 (s, 1H), 5.49 (s, |

| Compounds | Preparation methods and structures of the products |
|---|---|
| | 2H), 4.14 (d, J = 6.4 Hz, 1H), 3.77 (ddd, J = 13.9, 6.5, 3.3 Hz, 1H), 3.41 (ddd, J = 13.4, 7.8, 5.1 Hz, 1H), 2.17 (d, J = 4.5 Hz, 1H), 1.33 (d, J = 6.3 Hz, 3H). |
| IV-83 | 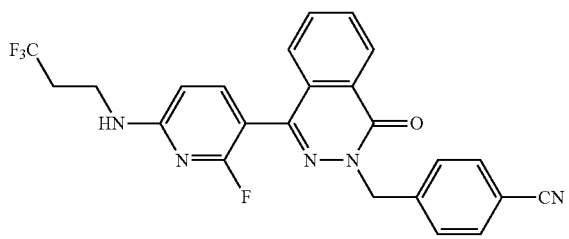 [SMILES: N#Cc1ccc(Cn2nc(-c3ccc(NCCC(F)(F)F)nc3F)c3ccccc3c2=O)cc1]<br>The above compound was prepared in the same method as that in Example 4, except that 1-amino-3,3,3-trifluoropropane was used in place of 2-methoxyethylamine. (White crystal, yield 76%)<br>$^1$H NMR (400 MHz, Chloroform-d) δ 8.54-8.48 (m, 1H), 7.85-7.78 (m, 2H), 7.68-7.56 (m, 6H), 6.44 (dd, J = 8.2, 1.7 Hz, 1H), 5.50 (s, 2H), 5.04 (t, J = 6.3 Hz, 1H), 3.75 (q, J = 6.4 Hz, 2H), 2.53 (qt, J = 10.9, 6.5 Hz, 2H). |
| IV-84 | 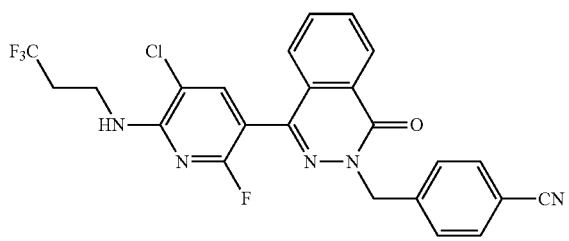<br>The above compound was prepared in the same method as that in Example 4, except that 1-amino-3,3,3-trifluoropropane was used in place of 2-methoxyethylamine. (White crystal, yield 86%)<br>$^1$H NMR (400 MHz, Chloroform-d) δ 8.51 (dd, J = 6.3, 3.1 Hz, 1H), 7.87-7.80 (m, 2H), 7.70 (d, J = 7.8 Hz, 1H), 7.65 (d, J = 8.1 Hz, 2H), 7.62-7.55 (m, 3H), 5.58 (t, J = 6.2 Hz, 1H), 5.49 (s, 2H), 3.85 (q, J = 6.4 Hz, 2H), 2.56 (qt, J = 10.8, 6.5 Hz, 2H). |

Test Example 1: Effect of Compounds Prepared in the Examples on DNA Replication Ability of HBV 1. Experimental Materials 1.1. Screening System Human hepatoblastoma cell line HepG2.2.15 stably transfected with full-length HBV (provided by Shanghai Institute of Materia Medica, Chinese Academy of Sciences)

1.2 Experimental Instruments

Incubator (ThermoForma3111); Microplate reader (Molecular Devices Spectra Max 190); Electronic balance; Microscope; Biosafety cabinet (Heal Force safe15);

Centrifuge (Eppendorf Centrifuge 5810R); Real-Time PCR (FASTA GEN-DNA fast2000)

1.3 Experimental Drugs and Reagents

Positive drug and formulation: Lamivudine (3TC), synthesized by department of medicinal chemistry, the Shanghai Institute of Materia Medica, Chinese Academy of Sciences, was formulated into a 40 mM stock solution with DMEM/High Glucose culture solution (Dulbecco's modified Eagle's medium, Hyclone).

Other Solutions and Formulations:

DMEM/High Glucose medium: Dulbecco's modified Eagle's medium 1× (Hyclone) phosphate buffer (PBS, pH7.3, 1 L): NaCl, 8.0 g; $Na_2HPO_4$, 1.16 g; $KH_2PO_4$, 0.2 g; KCl: 0.2 g;

MTT solution: MTT (Sigma), formulated to 5 mg/ml with PBS;

DNA extraction kit: DNeasy® Blood & Tissue (Qiagen)

2. Experimental Methods 2.1 Cell Culture

HepG2.2.15 cells were cultured and passaged according to conventional methods. DMEM containing 10% (v/v) bovine serum and the selective antibiotic G418 was used as a medium, the cells were cultured in an incubator at 37° C. under 5% $CO_2$ for 8 days (the medium was exchanged on the 4th day).

2.2 Formulation of the Test Compounds and the Positive Drug

The test compounds were formulated with DMSO into a 40 mM stock solution, which was then prepared into a solution at the defined highest concentration using a DMEM medium containing 10% Hyclone™ Fetal Bovine Serum, followed by diluting the same; the positive drug was lamivudine, which was also prepared into a solution at the defined concentration with the DMEM medium containing 10% Hyclone™ Fetal Bovine Serum.

2.3 MTT Assay for Cytotoxicity

HepG2.2.15 cells were seeded at 5×10³ cells/well in a 96-well plate, and cultured for eight days in the presence of the compounds according to the above method, and then 200 μl of the supernatant was taken out, followed by addition of the MTT solution. After 4 hours of culture, a lysate was added. After 12 hours of culture, the $OD_{570}$ was measured on a microplate reader. By comparing with the absorbance of the control well, the percentage of viable cells was calculated, and $CC_{50}$, the concentration required for the reduction of cell viability by 50%, was calculated.

2.4 Measurement of HBV DNA Content in the Supernatant of Cell Culture

HepG2.2.15 cells were treated with compounds at different concentrations for 8 days (the medium was exchanged on the 4th day), and the supernatant was aspirated, and the HBV DNA contained in the mature virus particles in the supernatant was quantitated by using a real-time PCR method.

DNA in the Supernatant of HepG2.2.15 Cell Cuturewas Extracted by a Column (Qiagen, DNeasy® Blood & Tissue Handbook)

1) The supernatant DNA from a 96-well plate, 200 μl/well, was collected, wherein the contents in the duplicate wells were collected into a same EP tube, and centrifuged at 4000 rcf for 5 min, and the supernatant was collected;

2) 200 μl of the supernatant was added into a 1.5 ml EP tube, added with 20 μl of proteinase K and 200 μl of Buffer AL (Qiagen, DNeasy® Blood & Tissue Kit), vortexed to be mixed thoroughly, and incubated at 56° C. for 10 min;

3) 200 μl of ethanol was added and vortexed to be mixed thoroughly;

4) all the liquid obtained from step 3) was added into a DNeasy Mini spin column (Qiagen, DNeasy® Blood & Tissue Kit) placed in a 2 ml waste liquid collection tube, and centrifuged at 6000 rcf for 1 min, and the supernatant was discarded;

5) the DNeasy Mini spin column was placed in a new 2 ml waste liquid collection tube, added with 500 μl of Buffer AW1 (Qiagen, DNeasy® Blood & Tissue Kit), and centrifuged at 6000 rcf for 1 min, and the supernatant was discarded;

6) the DNeasy Mini spin column was placed in a new 2 ml waste liquid collection tube, added with 500 μl of Buffer AW2, (Qiagen, DNeasy® Blood & Tissue Kit), and centrifuged at 20000 rcf for 3 min, and the supernatant was discarded;

7) the DNeasy Mini spin column was placed in anew 1.5 ml EP tube, 50 μl of Buffer AE (Qiagen, DNeasy® Blood & Tissue Kit) was pipetted and directly applied onto the membrane of the DNeasy Mini spin column, which was then left at room temperature for 5 min, and centrifuged at 6000 rcf for 1 min to elute the DNA from the membrane, the DNeasy Mini spin column was discarded, and the DNA sample was collected and stored at −20° C.

Real-Time PCR Detection of HBV DNA in Supernatant (HBV Nucleic Acid Quantitative Detection Kit, DAAN Gene)

1) Standard curve: $1e^7$-$1e^4$ IU/ml, the sample amount was 1 μl, a blank well was set so as to check whether the reaction system is polluted or not;

2) 1 μl of a DNA sample was added in sequence;

3) Addition of enzyme and reaction buffer: two tubes of the reaction solution were first added into the enzyme, mixed well and centrifuged slightly, placed on ice, added with the sample, followed by addition of 19 μl of the enzyme reaction solution, wherein, during the addition, the DNA sample should be sure of not being touched to cause contamination;

4) the sample was sealed with a sealing film and centrifuged;

5) PCR reaction:
Stage 1: 93° C., 2 min
Stage 2: 10 cycles
Step 1: 93° C., 45 s
Step 2: 55° C., 1 min
Stage 3: 45 cycles
Step 1: 93° C., 30 s
Step 2: 55° C., 45 s
Sample: 20l
Detection: data were collected after completing the step 2 (55° C., 45 s) of the stage 3.

2.8 Data Processing

The experimental data were processed by using the Origin software and $IC_{50}$ was calculated.

Experimental Results:

The experimental results are shown in Table 1.

TABLE 1

Toxicity against HepG2.2.15 cells and the activity of inhibiting HBV DNA of the compounds of formula I in the examples

| Compounds | $CC_{50}$(μM) | $IC_{50}$(μM) |
| --- | --- | --- |
| I-1 | >100 | 7.3 |
| I-2 | 98.7 | 3.1 |
| I-3 | >100 | 0.5 |
| I-4 | >100 | 3.1 |
| I-5 | 51.8 | 1.5 |
| I-6 | >100 | 1.7 |
| I-7 | 48.9 | 3.8 |
| I-8 | >100 | 5.2 |
| I-9 | 40.7 | 0.3 |
| I-10 | 81.8 | 0.1 |
| I-11 | 22.6 | 0.9 |
| I-12 | 15.7 | 0.6 |
| I-13 | 32.7 | 1.2 |
| I-14 | 10.3 | 2.1 |
| I-15 | >100 | 6.2 |
| I-16 | 20.1 | 0.5 |
| I-17 | >100 | 1.6 |
| I-18 | 42.9 | 1.2 |
| I-19 | 77.5 | 0.2 |
| I-20 | 33.3 | 1.3 |
| I-21 | >100 | 1.6 |
| I-22 | >100 | 0.4 |
| I-23 | >100 | 0.6 |
| I-24 | >100 | 0.4 |
| I-25 | >100 | 1.3 |
| I-26 | >100 | 0.9 |
| I-27 | >100 | 0.3 |
| I-28 | 73.1 | 1.0 |
| I-29 | >100 | 4.6 |
| I-30 | >100 | 0.4 |
| I-31 | >100 | 0.6 |
| I-32 | >100 | 1.0 |
| I-33 | >100 | 1.3 |
| I-34 | >100 | 0.2 |
| I-35 | >100 | 0.3 |
| I-36 | 89 | 1.5 |
| I-37 | 95 | 2.7 |
| I-38 | 81 | 0.8 |
| I-39 | >25 | 0.21 |
| I-40 | >100 | 0.051 |
| I-41 | 46.6 | 0.108 |
| I-42 | 33.5 | 0.378 |
| I-43 | >100 | 1.5733 |
| I-44 | 31.54 | 0.294 |
| I-45 | >100 | 2.017 |
| II-1 | 41.5 | 3.8 |
| II-2 | 32.4 | 4.5 |
| II-3 | >100 | 8.8 |
| II-4 | 97.6 | 7.1 |
| III-1 | 87.8 | 6.2 |
| IV-1 | >100 | 5.4 |
| IV-2 | >100 | 1.18 |
| IV-3 | >100 | 5.5 |
| IV-4 | >100 | 3.3 |
| IV-5 | >100 | 0.12 |
| IV-6 | >100 | 0.8 |
| IV-7 | >100 | 0.8 |

TABLE 1-continued

Toxicity against HepG2.2.15 cells and the activity of inhibiting HBV DNA of the compounds of formula I in the examples

| Compounds | $CC_{50}(\mu M)$ | $IC_{50}(\mu M)$ |
|---|---|---|
| IV-8 | >100 | 0.9 |
| IV-9 | >100 | 1.3 |
| IV-10 | 47.9 | 1.7 |
| IV-11 | 98.5 | 0.4 |
| IV-12 | 46.3 | 3.7 |
| IV-13 | 78.5 | 3.8 |
| IV-14 | >100 | 1.5 |
| IV-15 | >100 | 0.27 |
| IV-16 | 88.3 | 1.0 |
| IV-17 | >100 | 0.13 |
| IV-18 | >100 | 0.21 |
| IV-19 | >100 | 0.27 |
| IV-20 | >100 | 0.30 |
| IV-21 | >100 | 1.30 |
| IV-22 | >100 | 3.5 |
| IV-23 | >100 | 4.5 |
| IV-24 | >100 | 0.35 |
| IV-25 | 54.1 | 1.2 |
| IV-26 | >100 | 0.43 |
| IV-27 | >100 | 0.0142 |
| IV-28 | 21.32 | 0.191 |
| IV-29 | 26.57 | 0.0439 |
| IV-30 | 10.16 | <0.0977 |
| IV-31 | 108.7 | 0.452 |
| IV-32 | 43.73 | 0.191 |
| IV-33 | 180.87 | <0.0977 |
| IV-34 | >100 | 15.7 |
| IV-35 | >100 | 1.233 |
| IV-36 | >100 | 0.482 |
| IV-37 | 86.5 | 2.18 |
| IV-38 | 9.759 | 0.343 |
| IV-39 | 18.43 | 0.684 |
| IV-40 | 18.63 | 0.66 |
| IV-41 | >100 | 0.3253 |
| IV-42 | 29.76 | 0.2923 |
| IV-43 | 89.82 | 0.2877 |
| IV-44 | 54.83 | <0.09766 |
| IV-45 | >100 | 0.3681 |
| IV-46 | >100 | 0.014 |
| IV-47 | 12.97 | 1.72 |
| IV-48 | 7.383 | 0.5163 |
| IV-49 | 93.57 | 0.1655 |
| IV-50 | >100 | 0.00965 |
| IV-51 | 89.88 | 0.092 |
| IV-52 | >100 | 0.0845 |
| IV-53 | 18.1 | 1.0686 |
| IV-54 | 8.554 | 0.4698 |
| IV-55 | 2.561 | 0.09 |
| IV-56 | >100 | 0.2145 |
| IV-57 | 100 | 0.0878 |
| IV-58 | >100 | 5.3023 |
| IV-59 | >100 | 0.7803 |
| IV-60 | >100 | 0.7663 |
| IV-61 | 195.26 | 0.4651 |
| IV-62 | >100 | 0.4445 |
| IV-63 | >100 | 0.2624 |
| IV-64 | >100 | 1.2202 |
| IV-65 | >100 | 0.1165 |
| IV-66 | 94.05 | 0.1802 |
| IV-67 | >100 | 0.0042 |
| IV-68 | >100 | 0.332 |
| IV-69 | 25.02 | 0.0081 |
| IV-70 | >100 | 3.3199 |
| IV-71 | >100 | 2.7798 |
| IV-72 | >100 | 1.721 |
| IV-73 | >100 | 0.215 |
| IV-74 | >100 | 0.13 |
| IV-75 | >100 | 0.0366 |
| IV-76 | >100 | 0.2022 |
| IV-77 | 32.14 | 0.0277 |
| IV-78 | >100 | 0.3408 |
| IV-79 | >100 | 0.3468 |
| IV-80 | >100 | <0.098 |
| IV-81 | 65.21 | 0.334 |
| IV-82 | 71.88 | 0.209 |
| IV-83 | >100 | 0.413 |
| IV-84 | 63.54 | <0.098 |
| V-1 | >100 | 0.7 |
| V-2 | >100 | 0.3 |
| V-3 | >100 | 1.5 |
| V-4 | >100 | 1.3 |
| V-5 | >100 | 3.7 |
| V-6 | >100 | 2.6 |
| V-7 | >100 | 0.9 |
| V-8 | >100 | 1.1 |
| V-9 | >100 | 1.3 |
| V-10 | 47.9 | 0.7 |
| V-11 | >100 | 1.2 |
| V-12 | >100 | 4.5 |

Note:
$CC_{50}$ reflects the effect of the compounds in the examples on the growth of HepG2.2.15 cells, and is half (50%) lethal concentration.

$IC_{50}$ is the concentration at which the compounds in the examples inhibit DNA replication of HBV by half (50%).

It can be seen from the test results that the compounds in the examples all have an $IC_{50}$ less than 10 μM, demonstrating that each of them has high activity of inhibiting HBV DNA replication at the cellular level, and is less toxic to the growth of HepG2.2.15 cells.

Test Example 2: Effects of Compounds Prepared in the Examples on HBV Capsid Assembly Non-Denaturing Agarose Gel Electrophoresis $1\times10^6$ dispersed cells were added with 100l of cell lysate (50 mM Tris-HCl pH 7.5, 1 mM EDTA, 0.5% Nonidet P-40), and lysed on ice for 15 min, with vortexing every 5 min to make sure that the cells were sufficiently lysed. The lysed cells were centrifuged at 10,000×g for 10 min at 4° C. to remove nuclei and cell debris. 20 μl of the cell lysate was added into the well of 1.2% or 1.8% agarose gel. Electrophoresis was run at 70V for 2.5 h at 4° C. Every sample had a duplicate. After electrophoresis, the membrane-transferring was performed by siphon overnight. One sample was transferred to a nitrocellulose membrane (Amersham™ Hybond-ECL, GE), and the capsid was detected with anti-HBcAg antibody (Abcam) using Western blot method; another sample was in situ denatured with a denaturing solution (1.5 M NaCl, 0.5 M NaOH) for 45 min, neutralized with a neutralizing solution (1.5 M NaCl, 1 M Tris-HCl pH 7.4) for 45 min, and transferred to a nylon membrane (Amersham™ Hybond-N+, GE), and then the level of nucleic acid in the capsid was detected with HBV-specific probes by using Southern blot method. The results were shown in FIG. 1.

As shown in FIG. 1, all of the compounds I-11, I-26, I-10, I-9, I-24, I-3, and I-12 can induce the generation of an abnormal capsid with faster electrophoretic migration speed, and the content of HBV DNA in the capsid was significantly reduced, demonstrating that the compounds exert their anti-HBV activity by interfering with the assembly of the virus capsid.

Test Example 3: Tissue Distribution of the Compounds Prepared in the Examples in Mice 1. Sample Pretreatment Method 10 μl of a plasma and tissue sample was placed in a 1.5 ml centrifuge tube, added with 100 μl of an internal standard solution (5.00 ng/ml verapamil and 50.0 ng/ml Glibenclamide solution in acetonitrile), vortexed for 60 seconds, and then centrifuged for 3 min (at 12000 rpm); 75 μl of the supernatant was transferred to a 96-well plate loaded with an equal volume of water, and shaken for mixing well and then analyzed. The injection volume was 10 μl.

2. Standard Curve and Sample Preparation for Quality Control

Internal standard: an appropriate amount of verapamil and glibenclamide standards were dissolved and diluted in dimethyl sulfoxide (DMSO), shaken for mixing well, and prepared into a stock solution with a mass concentration of 2000 μg/ml, which was further diluted into internal standard working solutions of 5.00 ng/ml and 50.0 ng/ml.

Stock solution: an appropriate amount of the compound was weighted and formulated into a 2.00 mg/ml stock solution with DMSO.

Working solution: The stock solution was stepwisely diluted to obtain the solutions at each gradient concentration. 5.00 μl of reference standard working solution was added to 45.0 μl of a mice blank plasma and blank tissue. Then it was treated according to the method described in the section of "Sample pretreatment method".

3. Formulation of the Preparations of the Test Compounds

Administration solution: a certain amount of a compound was precisely weighed and formulated into a 2.00 mg/ml milky white suspension in a ratio of 2.5% DMSO+97.5% (0.5% MC).

Approximately 0.1 ml of orbital blood and liver was collected in EDTAK2 for anticoagulation from each animal that had been anesthetized with isoflurane. For the PO group, the blood was collected at 1 h, 3 h, and 8 h after administration of the test compound. After collection, the blood sample was analyzed by using comparative compounds I-70 and I-88. The results are shown in Table 2 below.

I-70

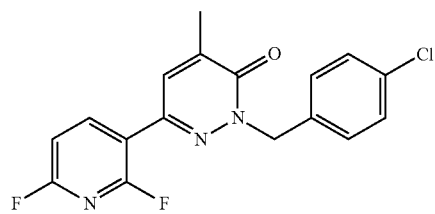

I-88

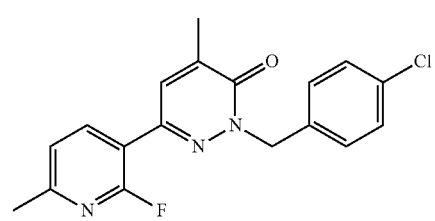

TABLE 2

Mean drug concentrations of the example compounds and the comparative compounds in different tissues of mice (po 10 mg/kg)

| Compounds | time (h) | Plasma (ng/ml) | Liver (ng/g) |
|---|---|---|---|
| comparative compound I-70 | 1 | 161 | BLQ[a] |
|  | 3 | 71.7 | BLQ |
|  | 8 | 17.3 | BLQ |
| comparative compound I-88 | 1 | 169 | 34.2 |
|  | 3 | 180 | 9.64 |
|  | 8 | 0.993 | BLQ |
| I-10 | 1 | 61.0 | 476 |
|  | 3 | 12.5 | 318 |
|  | 8 | BLQ | 2.91 |
| I-11 | 1 | 33.3 | 1224 |
|  | 3 | 32.5 | 1413 |
|  | 8 | 23.0 | 815 |
| IV-5 | 1 | 154 | 1029 |
|  | 3 | 63.2 | 1047 |
|  | 8 | 80.1 | 1188 |
| IV-15 | 1 | 549 | 7270 |
|  | 3 | 437 | 4461 |
|  | 8 | 257 | 2800 |

Note:
[a]BLQ means that the content is below the minimum detection limit of the instrument.

As shown in Table 2, the example compounds show metabolic properties (i.e., metabolic stability in the liver) much superior to those of the comparative compounds. Compounds I-10, I-11, IV-5 and IV-15 have good liver targeting in mice, and can be stably present and enriched in liver, with a low content in plasma.

The example compounds exert their antiviral activity by interfering with the nucleocapsidization of viral RNA. They showed high activity of inhibiting HBV DNA replication at the cellular level, with little toxicity to the growth of HepG2.2.15 cells, and have good liver targeting, and can be stably present and enriched in the liver, and thus they are effective HBV inhibitors.

The preferred embodiments of the present invention have been described in details as above. However, the present invention is not limited to the specific details of the above embodiments. A variety of simple modifications can be made to the technical solution of the present invention within the scope of the technical concept of the present invention, and all of these simple modifications are within the protection scope of the present invention.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula I, or a pharmaceutically acceptable salt, solvate or prodrug thereof, wherein:

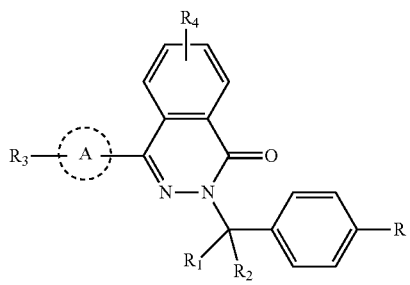

R is Cl or CN;
$R_1$ and $R_2$ are each independently H or D;
A is pyridyl, pyrimidinyl or pyrazinyl;
$R_3$ represents one or more substituents, each being independently selected from the group consisting of H, D, halogen, cyano, hydroxyl, trifluoromethyl, methyl optionally substituted by one or more D, methylol, methoxymethyl optionally substituted by one or more D, acetoxymethyl, methoxy optionally substituted by one or more D, methoxyethoxy, amino, methylamino, dimethylamino, t-butylamino, cyclopropylamino, epoxypropylamino, acetylamino, oxetanylamino, methoxymethylamino, methoxyethylamino, methoxypropylamino, ethoxyethylamino, ethoxypropylamino, methoxycarbonylethylamino, methoxycarbonylpropylamino, ethoxycarbonylmethylamino, ethoxycarbonylethylamino, ethoxycarbonylpropylamino, hydroxyethylamino, hydroxypropylamino, hydroxybutylamino, cyclobutylamino, azetidinyl, N,N-dimethylaminomethylamino, N,N-dimethylaminoethylamino, N,N-dimethylaminopropylamino, N,N-dimethylaminobutylamino, t-butoxyacylaminobutylamino, 5-morpholinylmethyl, ethylaminoethylamino, ethylaminopropylamino, ethylaminobutylamino, methoxyethoxyethoxyethylamino, ethoxyethoxyethylamino, t-butoxycarbonylethylamino, t-butoxycarbonylpropylamino, t-butoxycarbonylmethoxyethylamino, carboxylethylamino, carboxylpropylamino, carboxymethoxyethylamino, 6-morpholinylmethyl, 6-(tetrahydrofuranyl)methylamino, methylsulfonylethylamino, (2,2-dimethyl-[1,3]-dioxolan-4-yl)-methylamino, 2,3-dihydroxypropylamino, 2-hydroxypropylamino, trifluoromethylethylamino, with the proviso that when A is pyridyl and R is Cl, $R_3$ is not H or D;

$R_4$ represents one or more substituents, each being independently selected from the group consisting of H, halogen, methyl, methoxy, cyano and trifluoromethyl.

2. The compound of formula I, or a pharmaceutically acceptable salt, solvate or prodrug thereof according to claim 1, wherein the compound of formula I is selected from the group consisting of the compounds having a structure represented by one of the following formulae I-I to I-V:

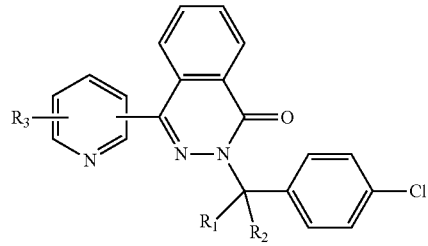

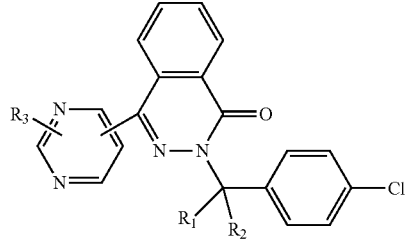

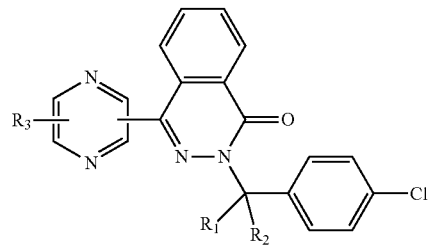

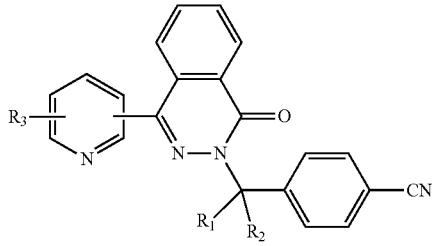

I-V

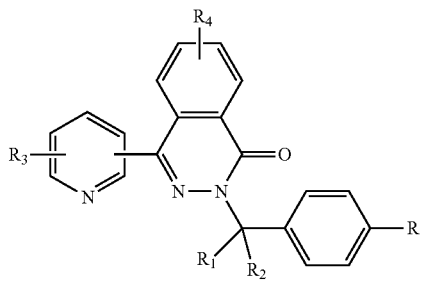

wherein, R, R₁, R₂, R₃ and R₄ are each independently defined as those in claim 1, except that R₄ is not H.

3. The compound of formula I, or a pharmaceutically acceptable salt, solvate or prodrug thereof according to claim 1, wherein:

the compound of formula I includes one or more optical isomers enantiomers, diastereoisomers or racemate mixtures of the compound of formula I;

the pharmaceutically acceptable salt includes an anionic salt and a cationic salt of the compound of formula I;

the solvate is a complex formed by the compound of formula I or a salt thereof and a pharmaceutically acceptable solvent.

4. The compound of formula I, or a pharmaceutically acceptable salt, solvate or prodrug thereof according to claim 1, wherein the compound of formula I is one of the following compounds:

I-3

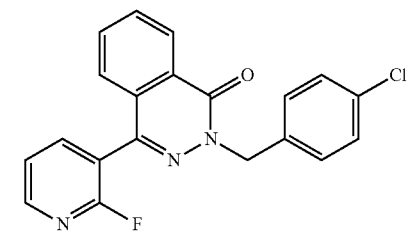

I-4

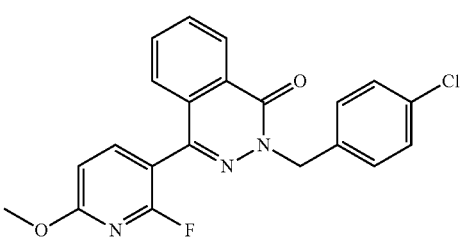

I-5

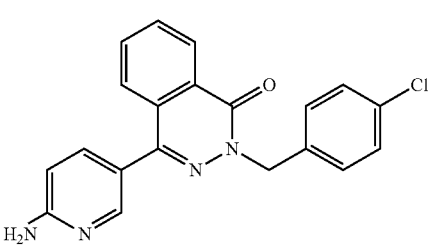

I-6

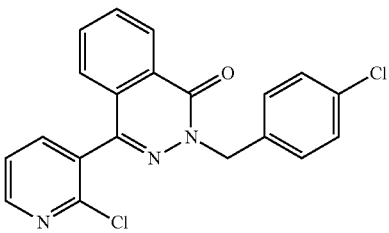

I-7

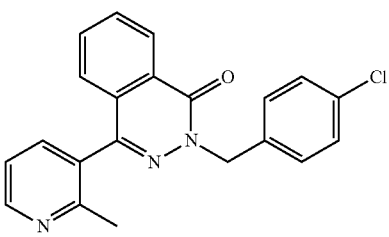

I-8

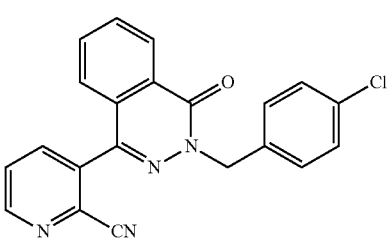

I-9

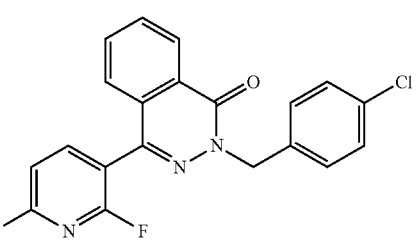

I-10

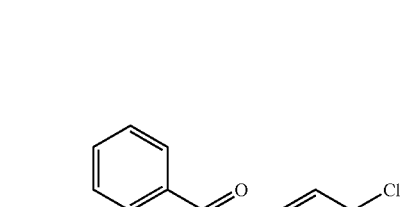

I-11

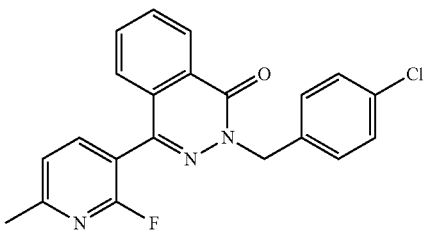

I-12
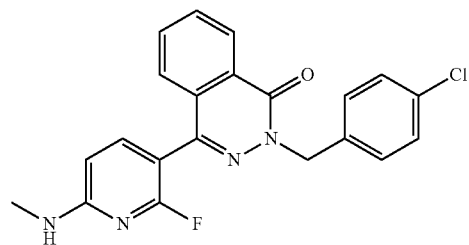
I-13
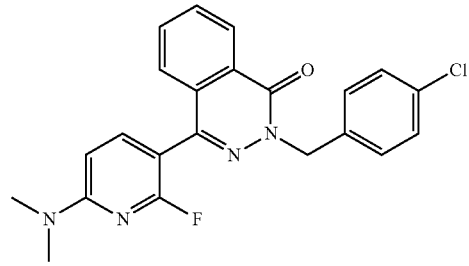
I-14
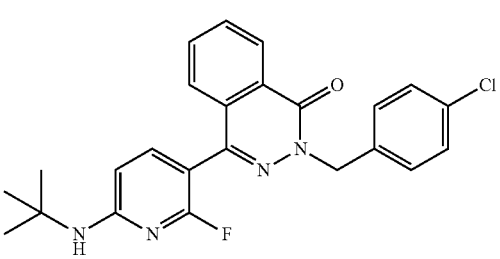
I-15
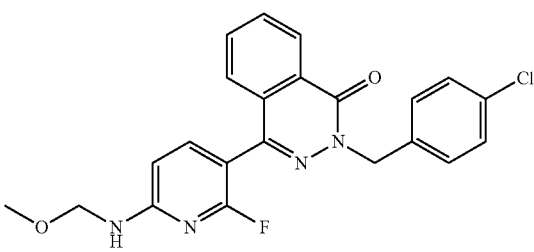
I-16
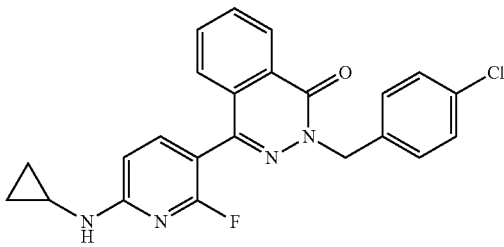
I-17
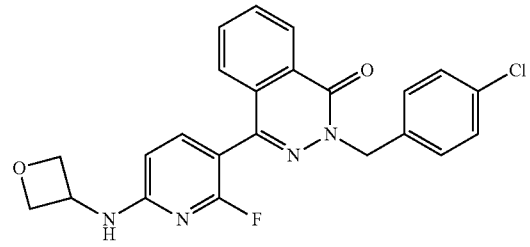
I-18
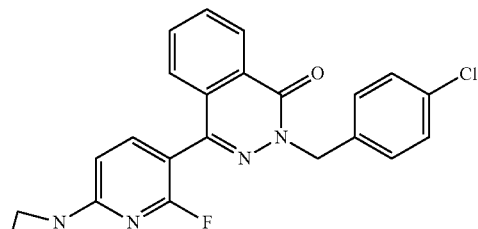
I-19
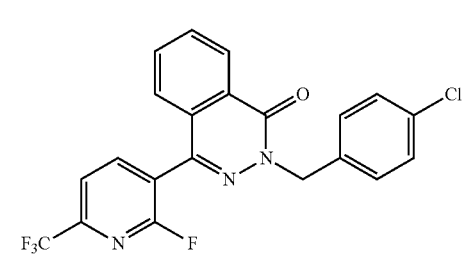
I-20
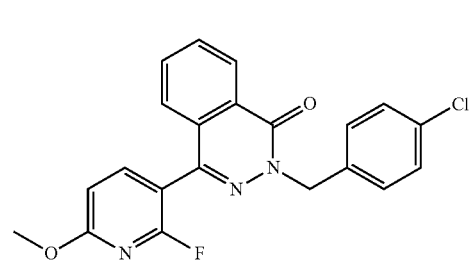
I-21
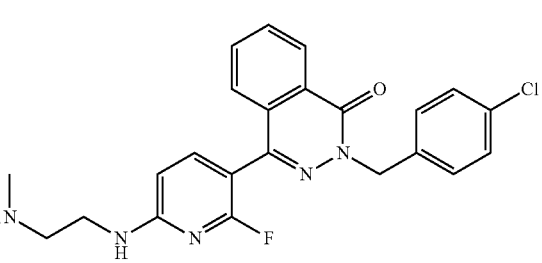
I-22
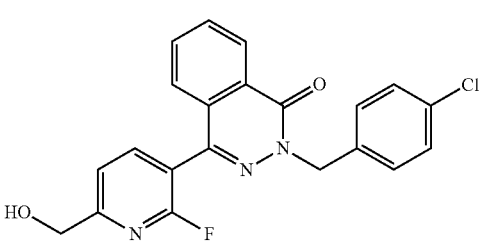
I-23
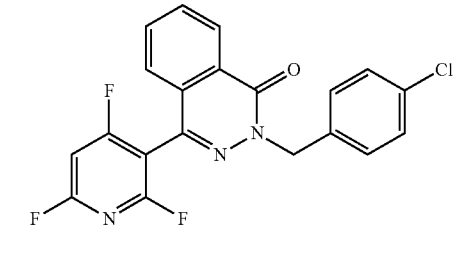

I-24
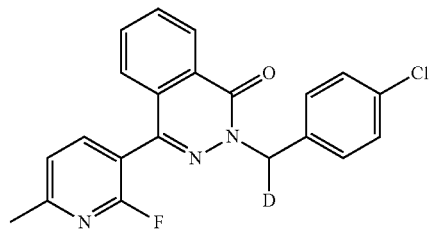
I-25
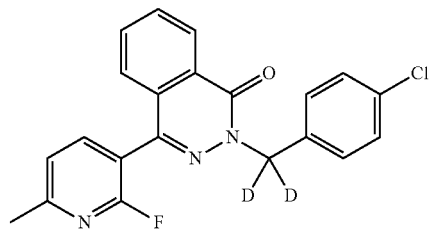
I-26
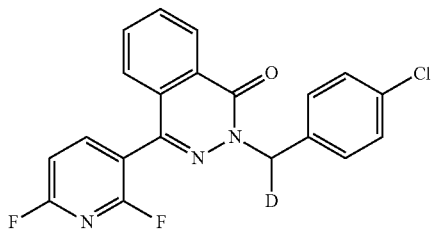
I-27
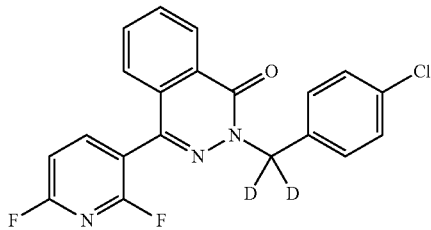
I-28
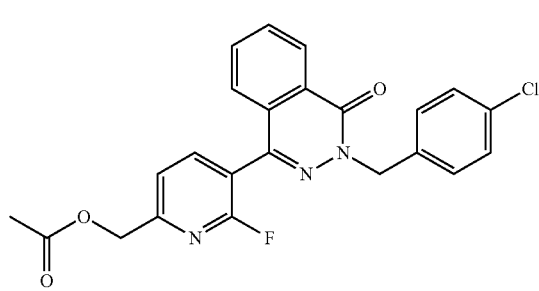
I-29
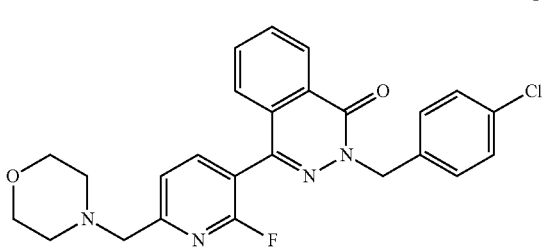
I-30
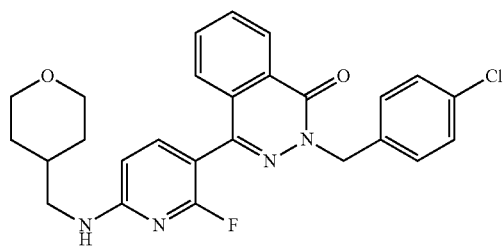
I-31
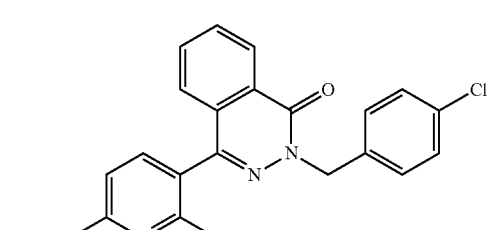
I-32
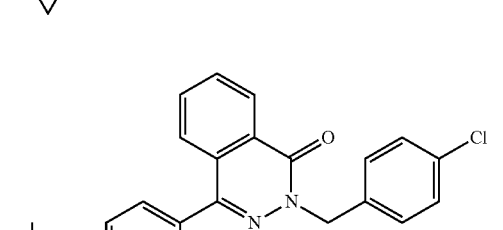
I-33
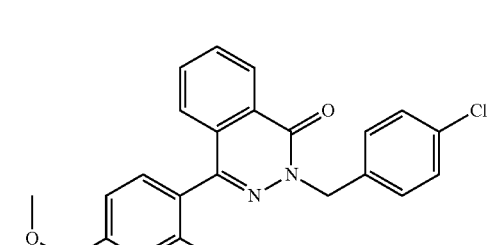
I-34
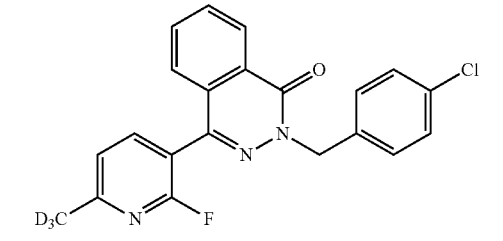
I-35
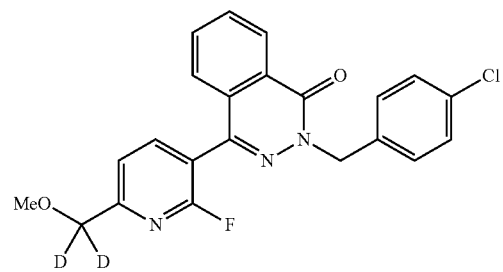

I-36
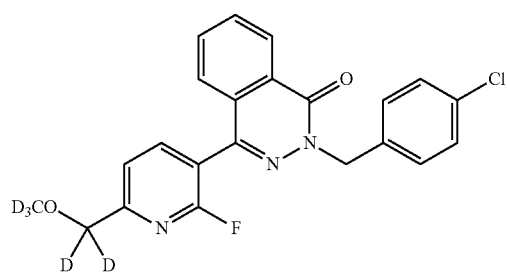
I-37
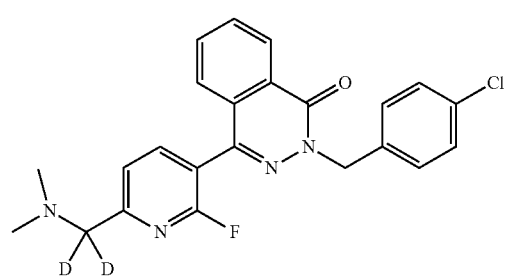
I-38
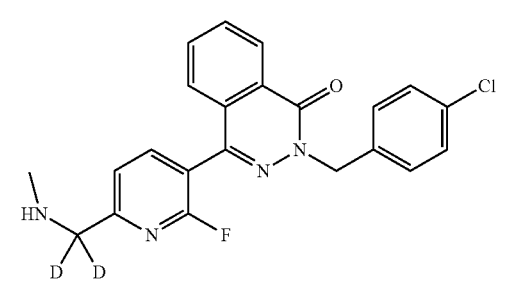
I-39
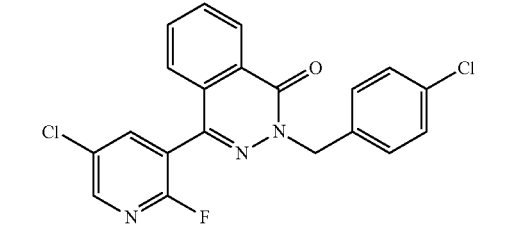
I-40
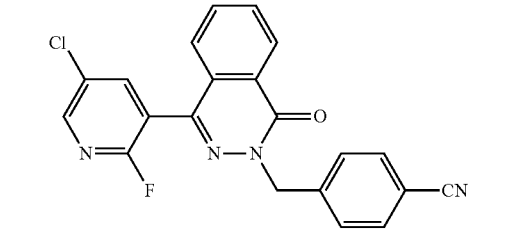
I-41
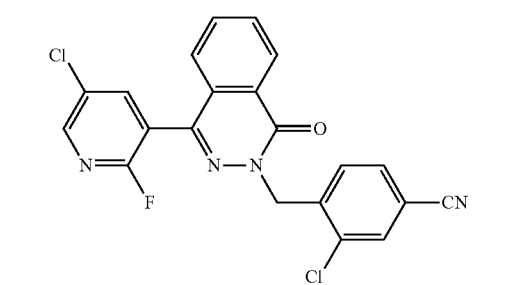
I-42
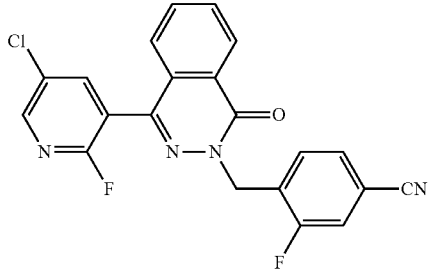
I-43
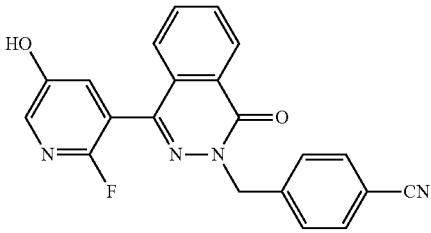
I-44
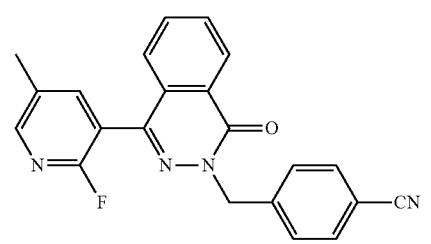
I-45
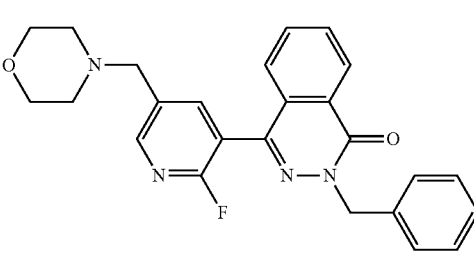
II-1
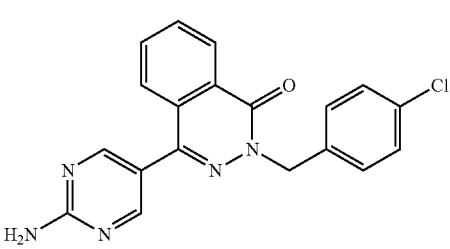
II-2
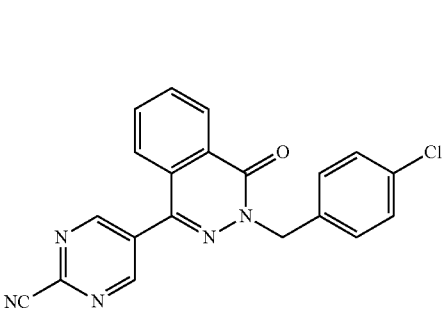

II-3
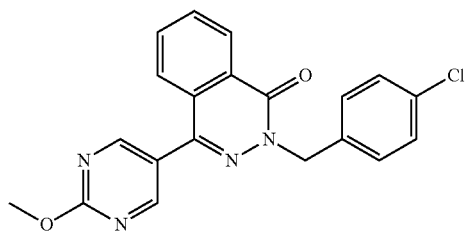
II-4
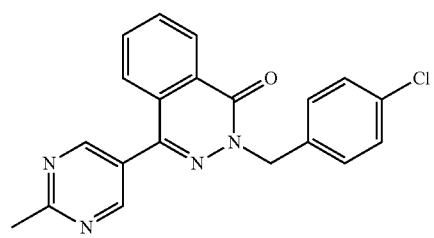
III-1
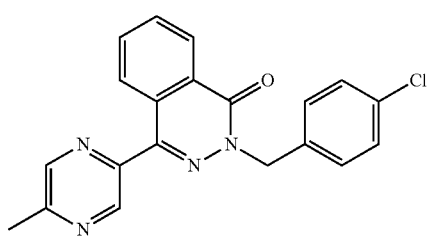
IV-1
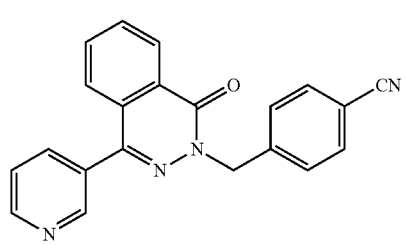
IV-2
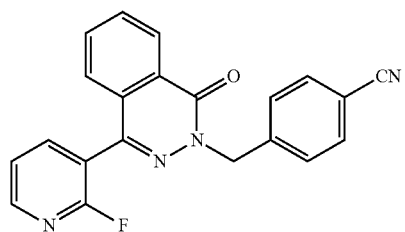
IV-3
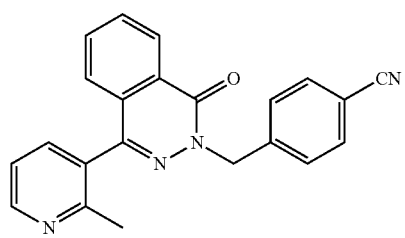
IV-4
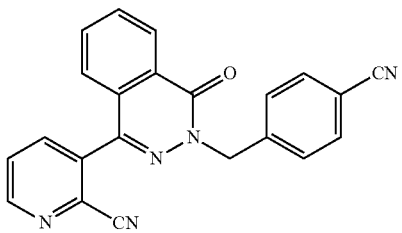
IV-5
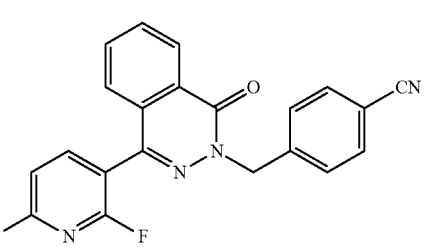
IV-6
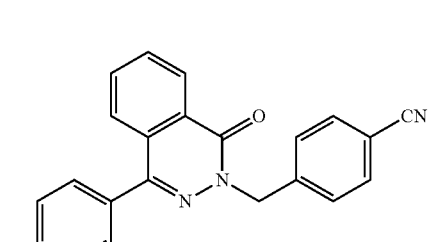
IV-7
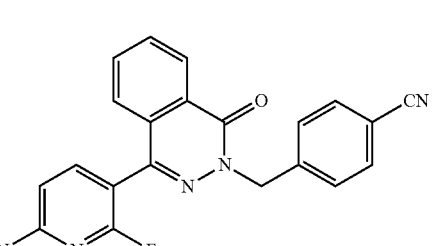
IV-8
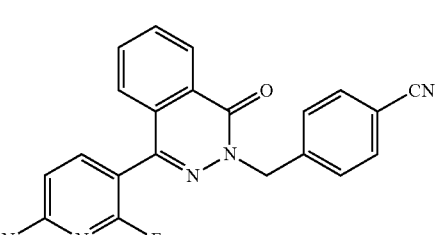
IV-9
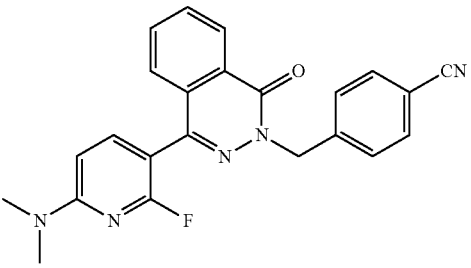

IV-10
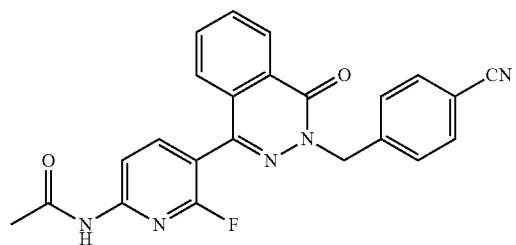
IV-11
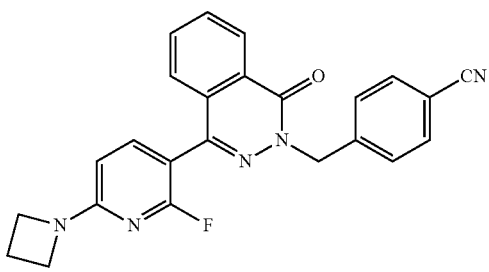
IV-12
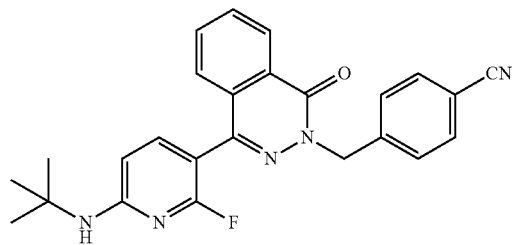
IV-13
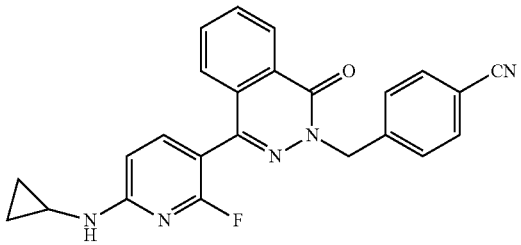
IV-14
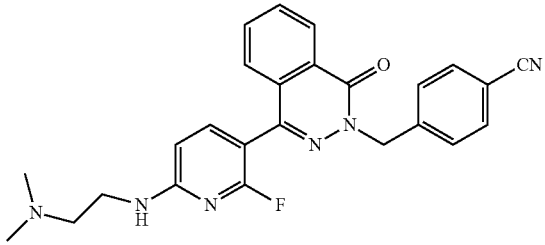
IV-15
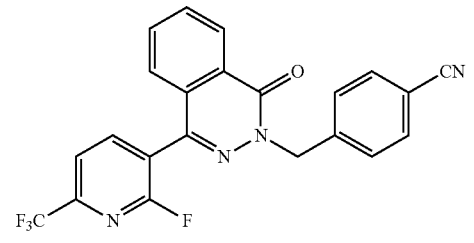
IV-16
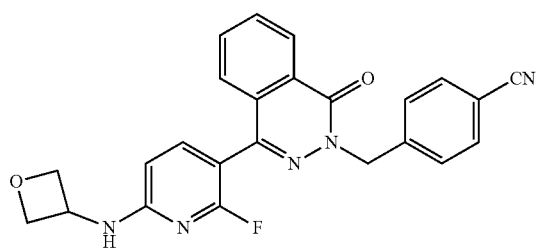
IV-17
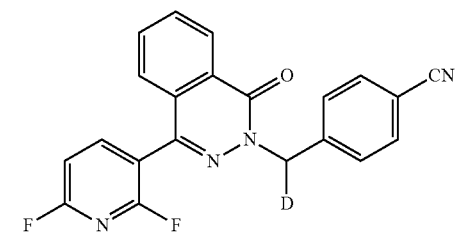
IV-18
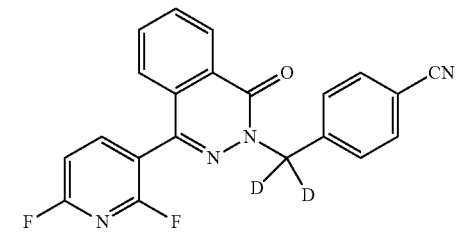
IV-19
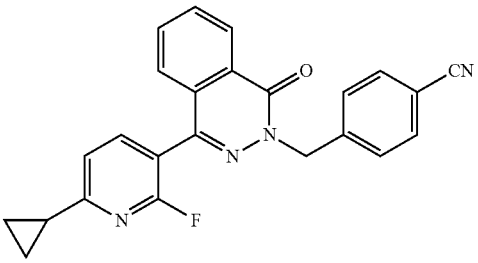
IV-20
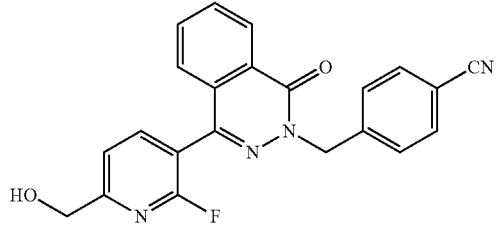
IV-21
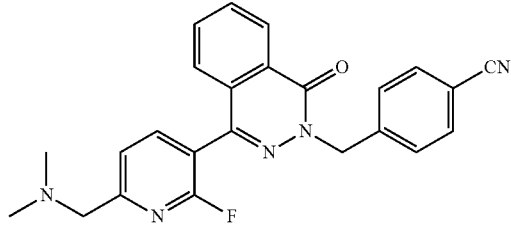

IV-22
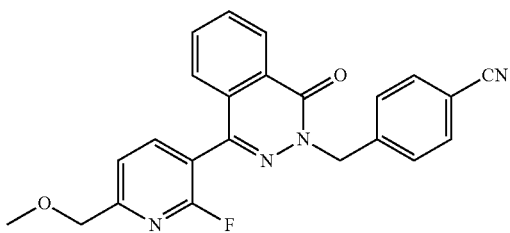
IV-23
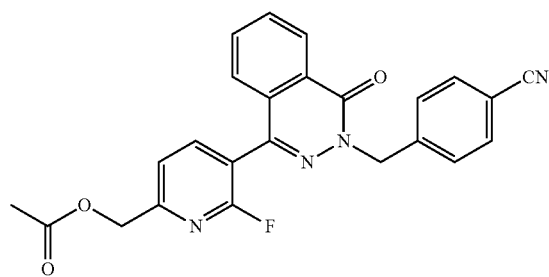
IV-24
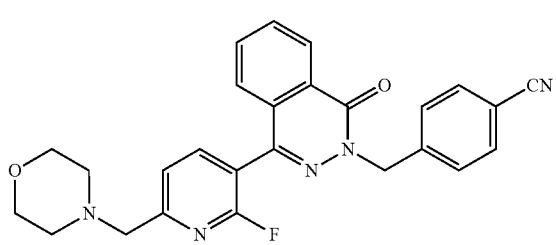
IV-25
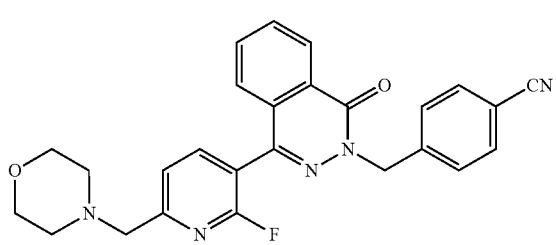
IV-26
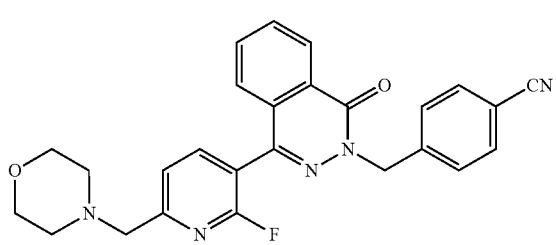
IV-27
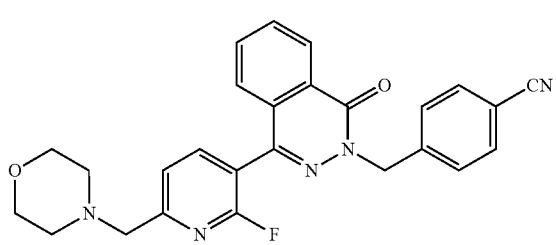
IV-28
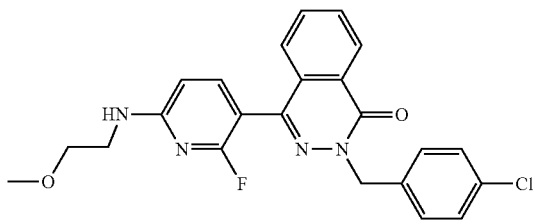
IV-29
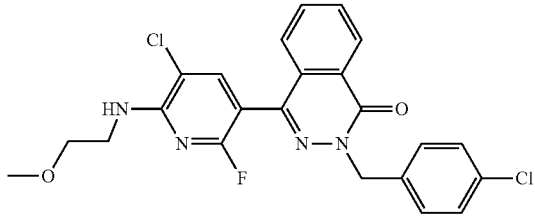
IV-30
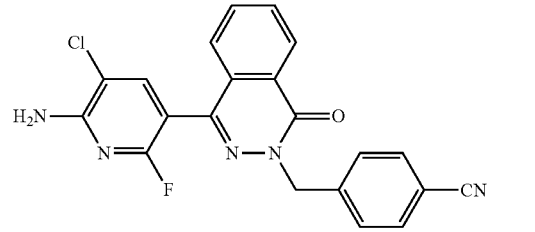
IV-31
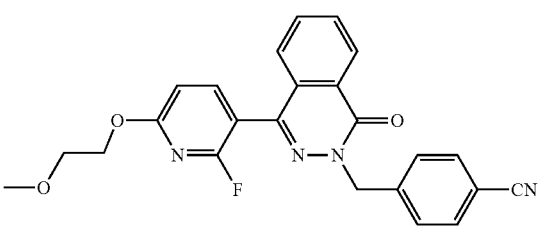
IV-32
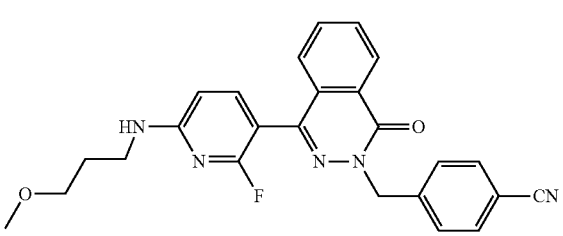
IV-33
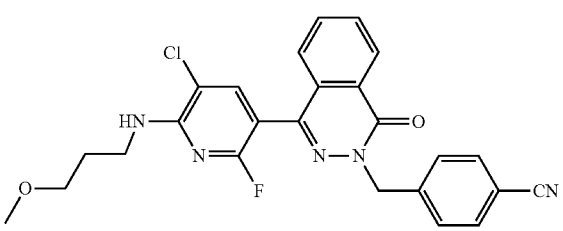

IV-34
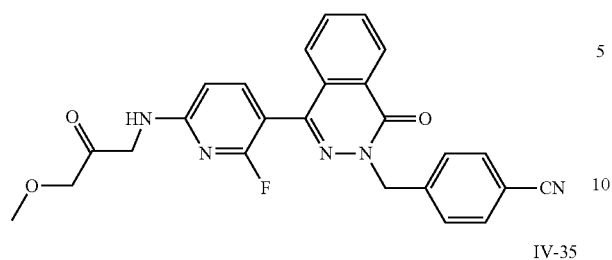
IV-40
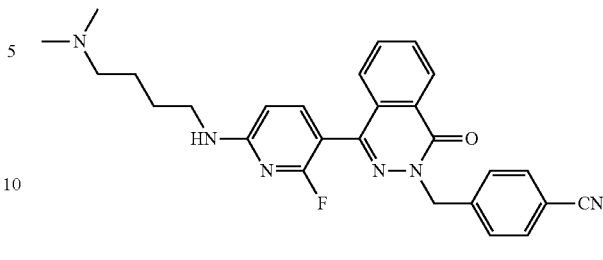
IV-35
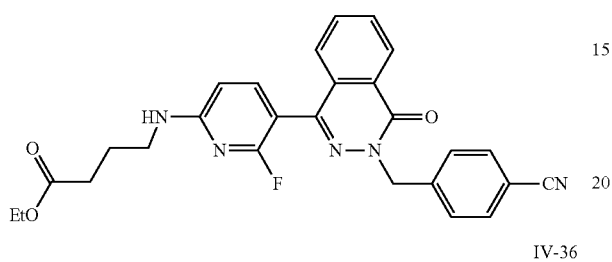
IV-41
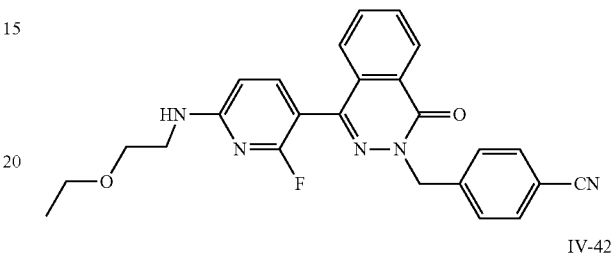
IV-36
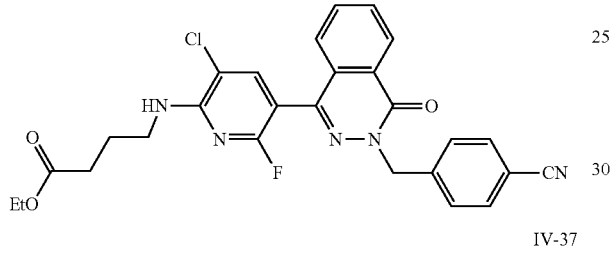
IV-42
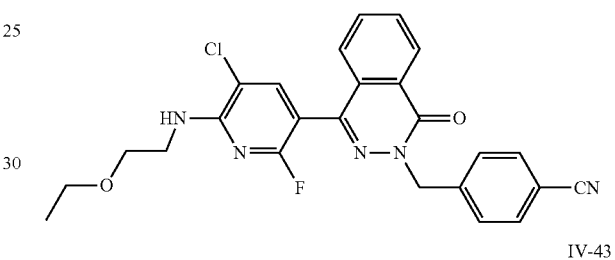
IV-37
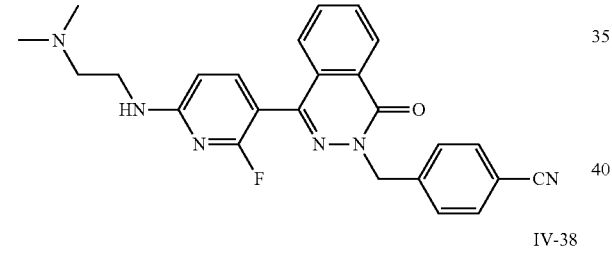
IV-43
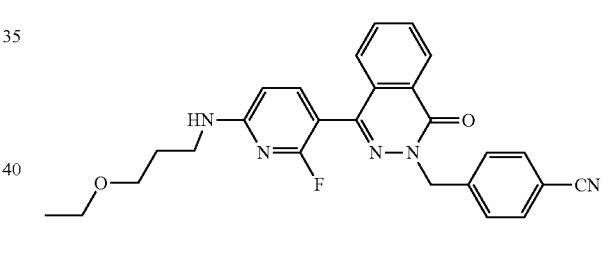
IV-38
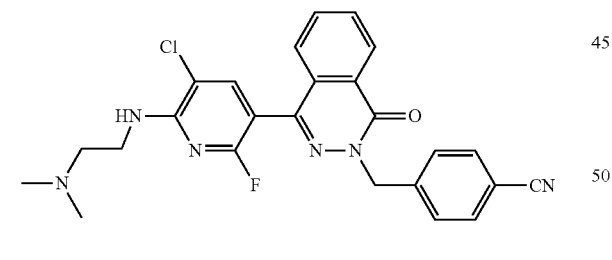
IV-44
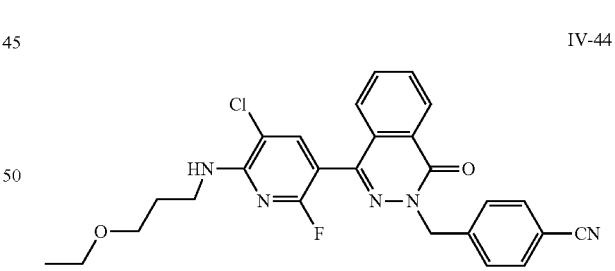
IV-39
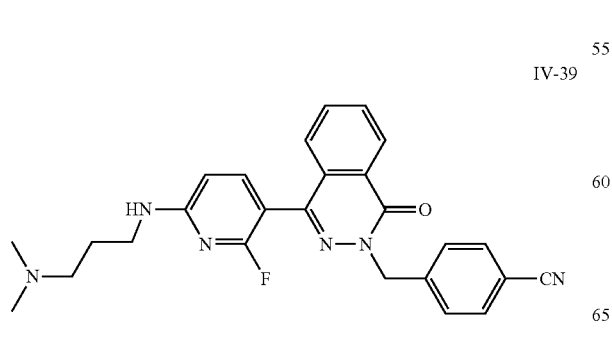
IV-45
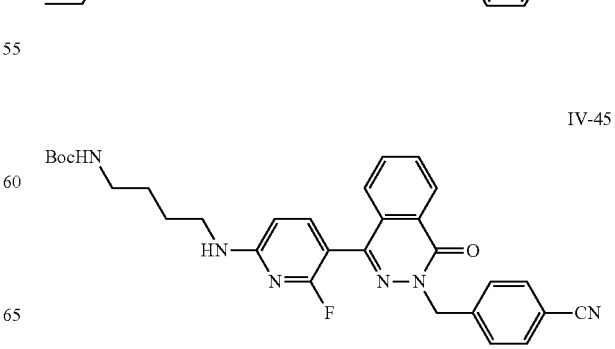

IV-46
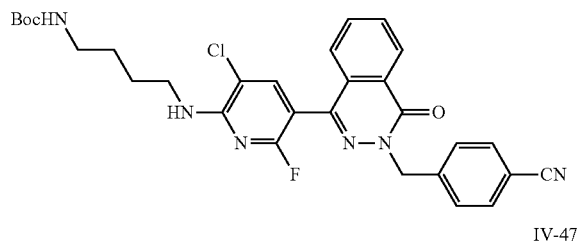
IV-47
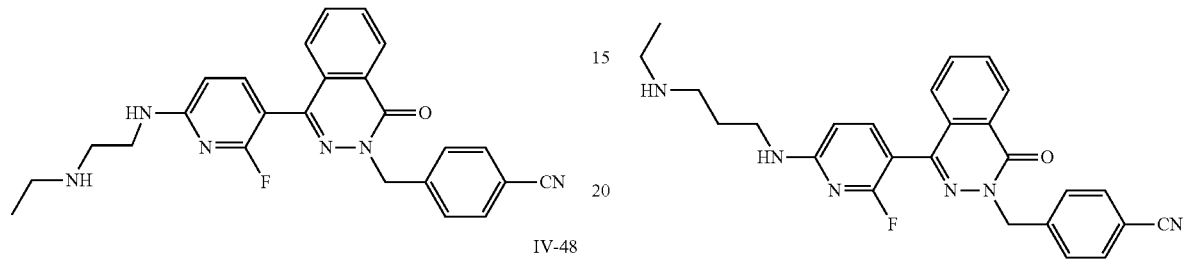
IV-48
IV-49
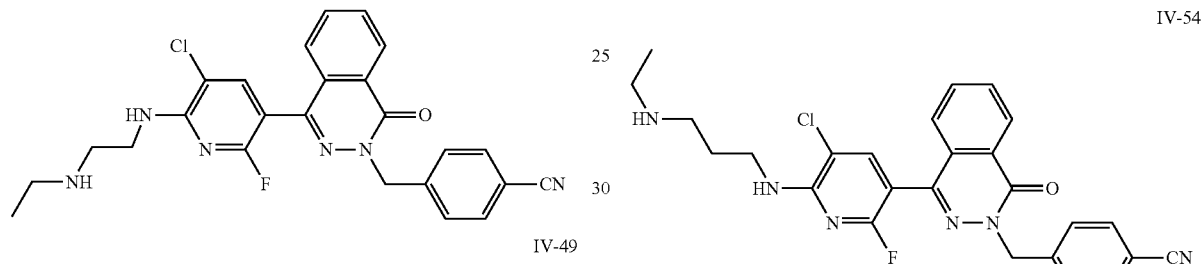
IV-50
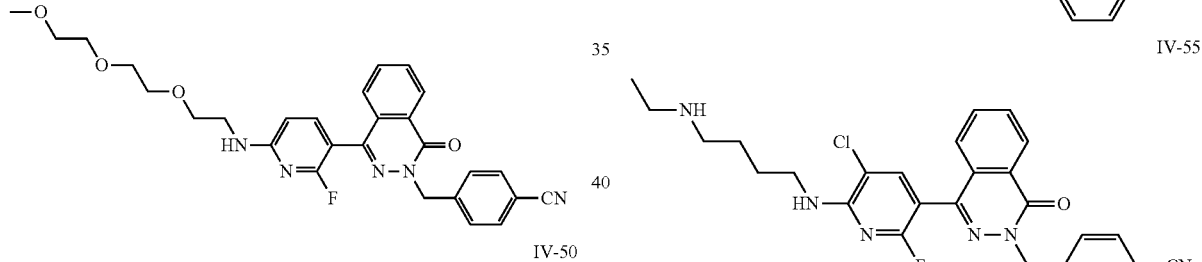
IV-51
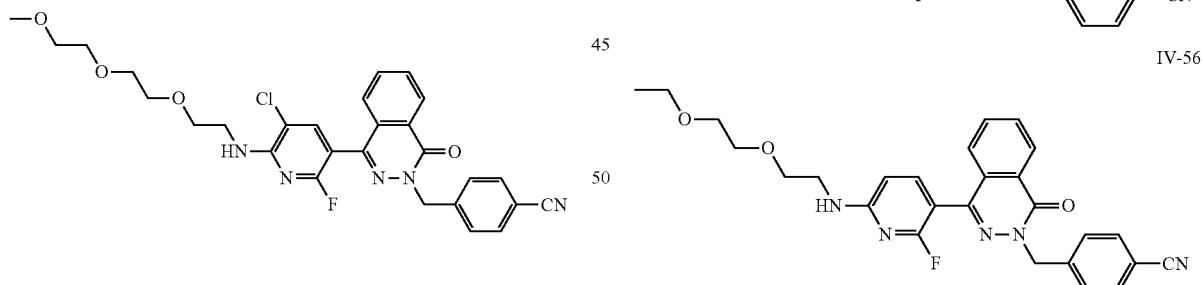
IV-52
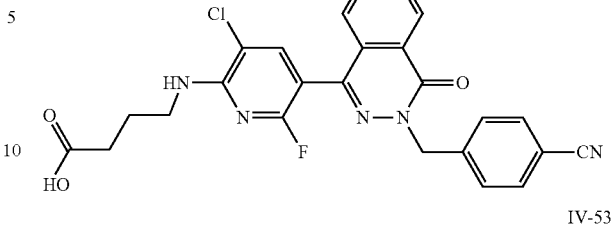
IV-53
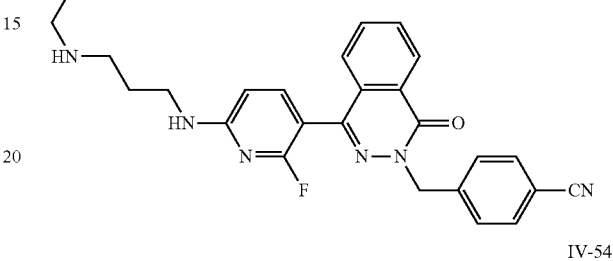
IV-54
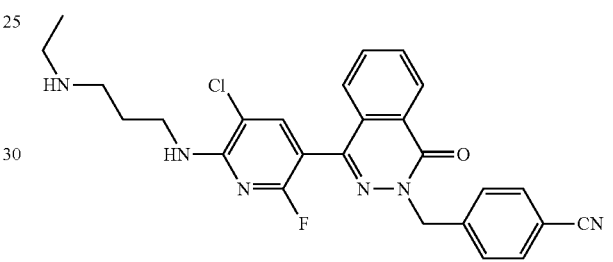
IV-55
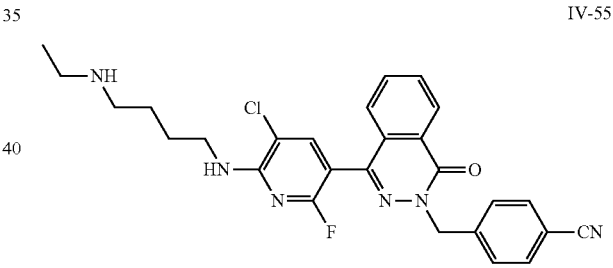
IV-56
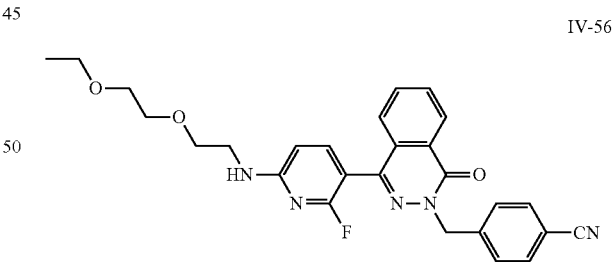
IV-57
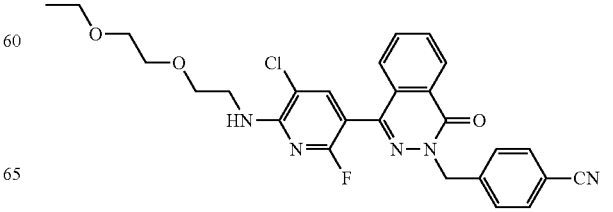

IV-58
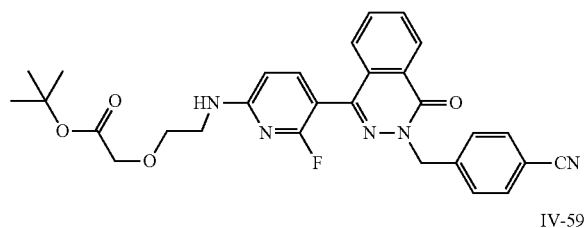
IV-64
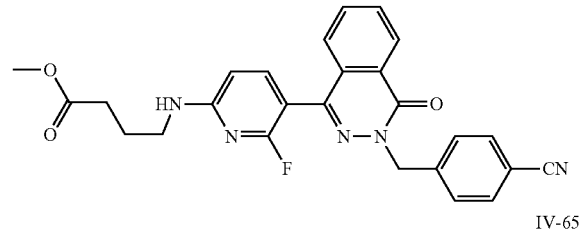
IV-59
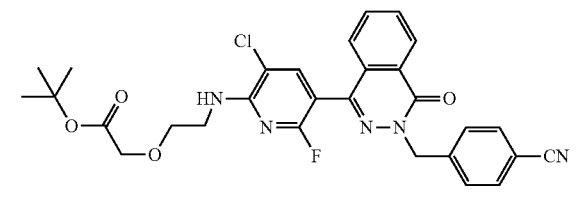
IV-65
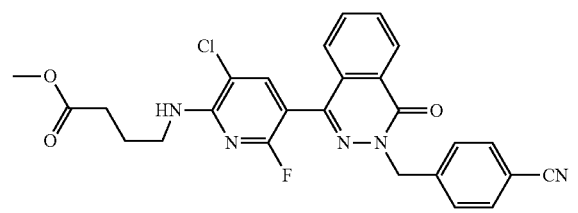
IV-60
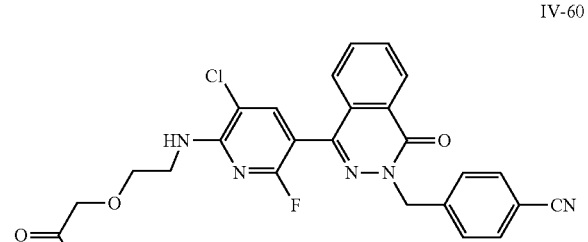
IV-66
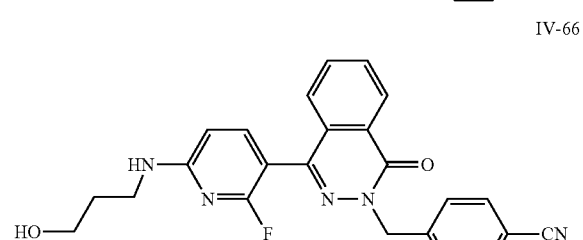
IV-61
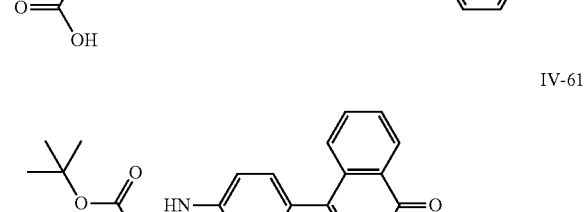
IV-67
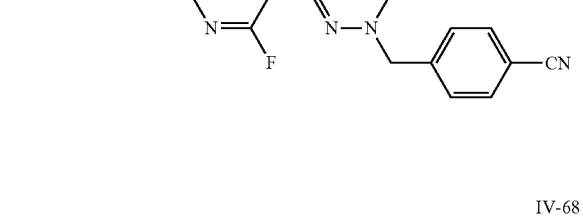
IV-62
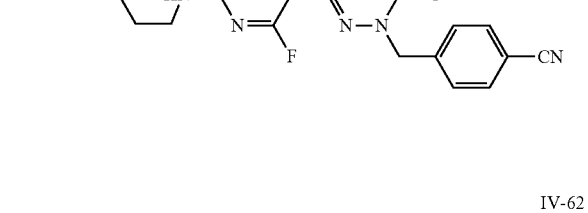
IV-68
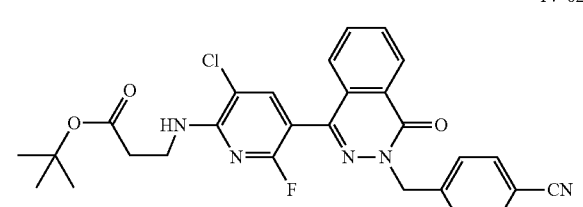 IV-70
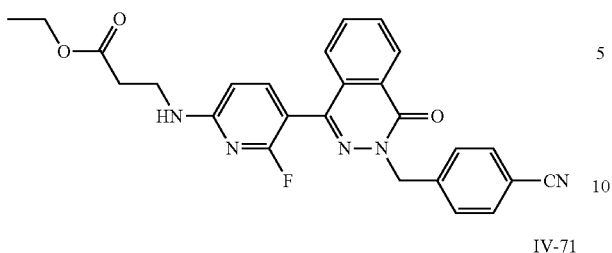
IV-71
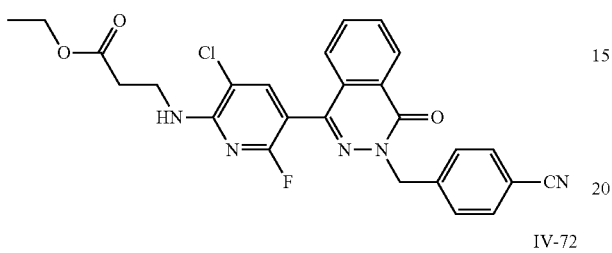
IV-72
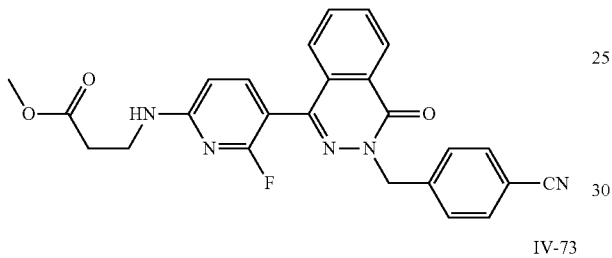
IV-73
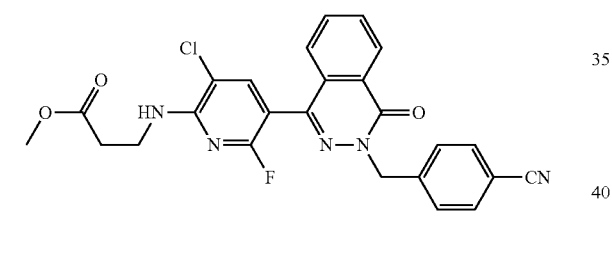
IV-74
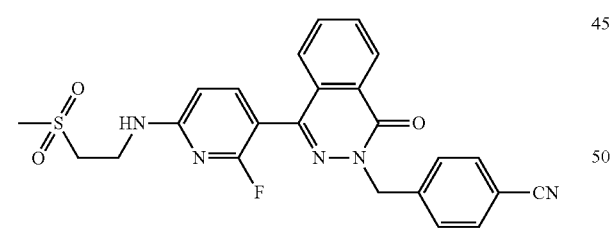
IV-75
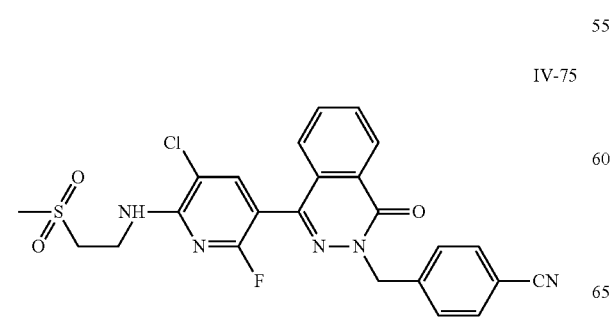
IV-76
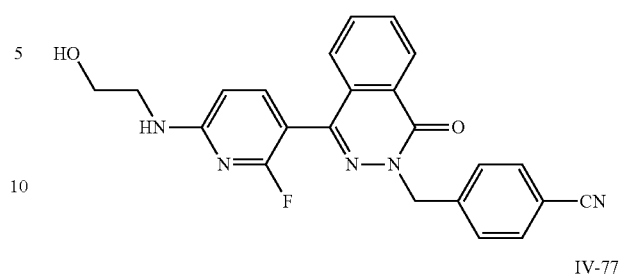
IV-77
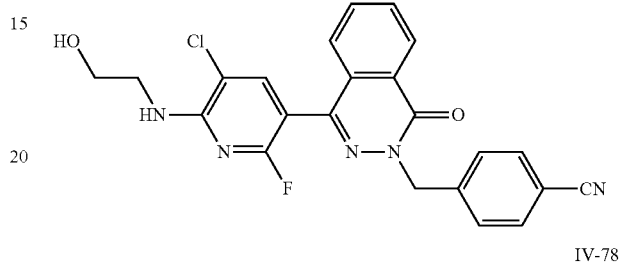
IV-78
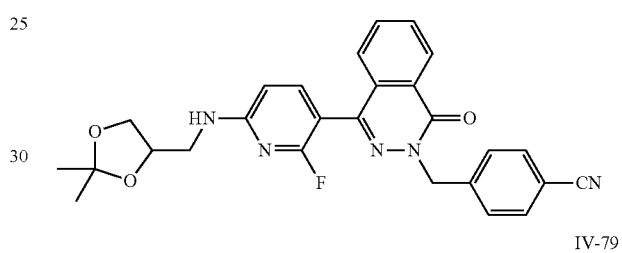
IV-79
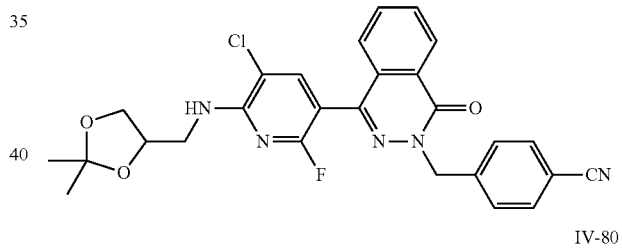
IV-80
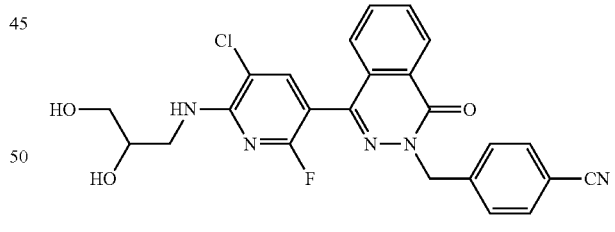
IV-81
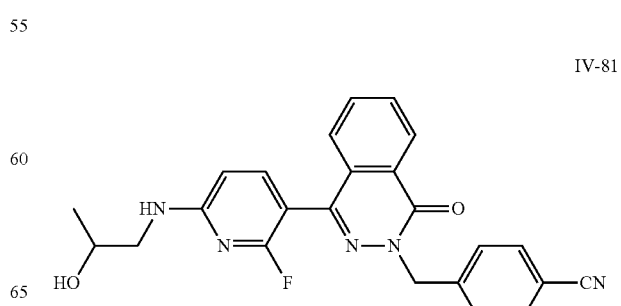

IV-82
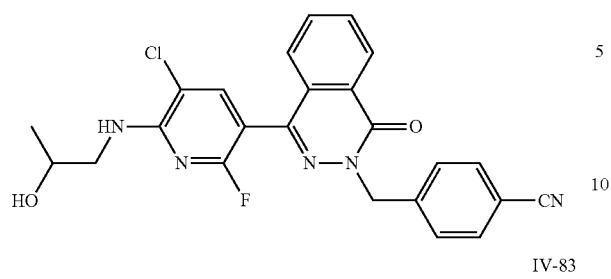
IV-83
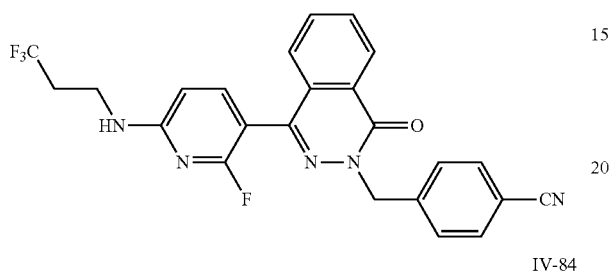
IV-84
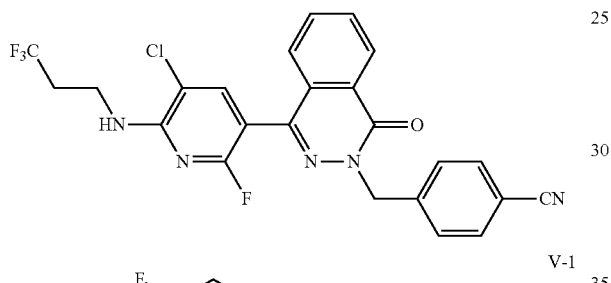
V-1
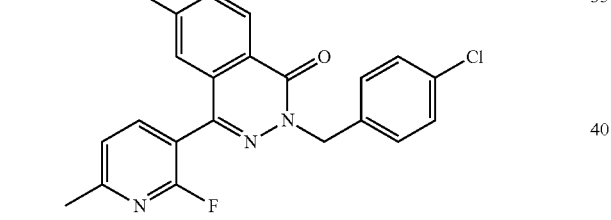
V-2
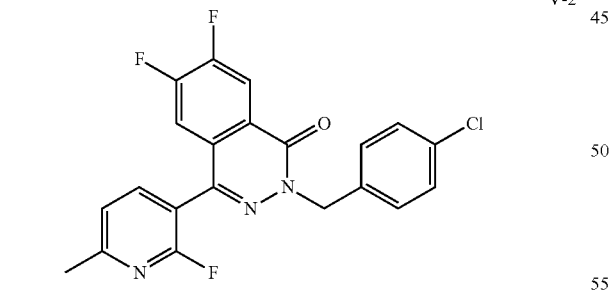
V-3
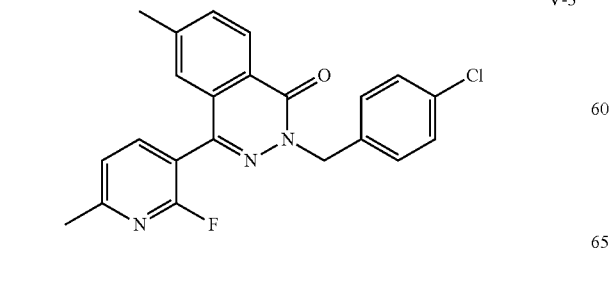
V-4
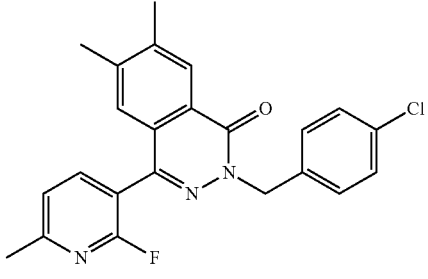
V-5
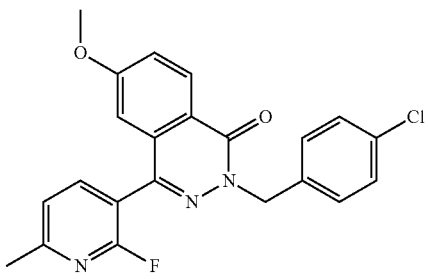
V-6
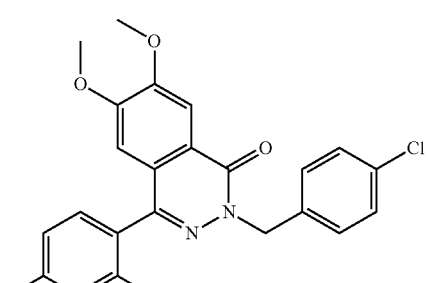
V-7
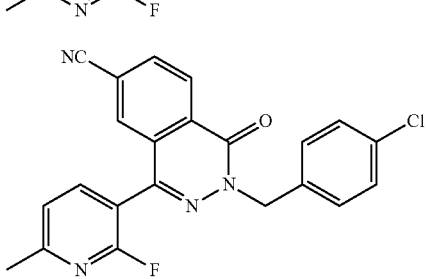
V-8
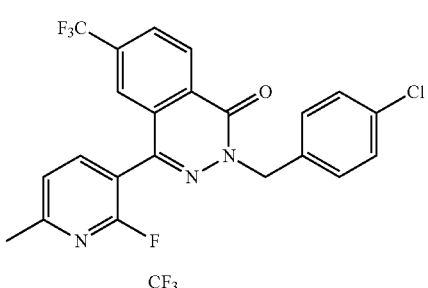
V-9
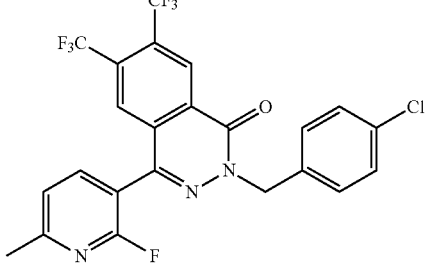

-continued

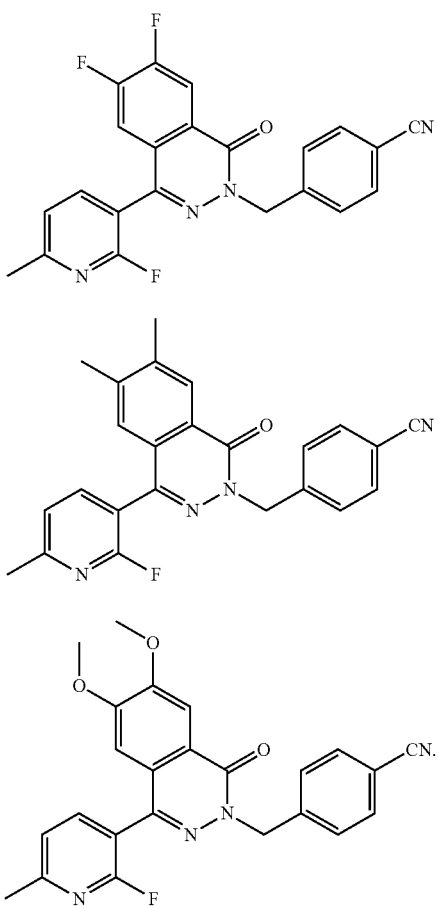

V-10

V-11

V-12

5. A method of preparing the compound of formula I, or a pharmaceutically acceptable salt, solvate or prodrug thereof according to claim 1, wherein the method of preparing the compound of formula I includes steps of one of the following routes:

Route 1:

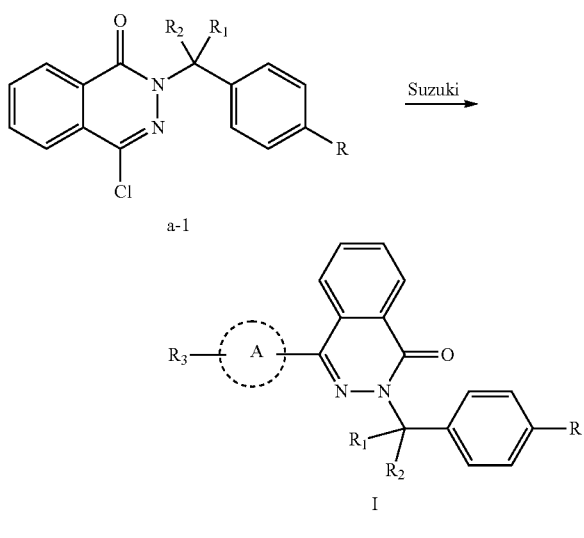

the compound I is obtained from the compound a-1 by a Suzuki reaction, wherein, R, $R_1$, $R_2$, $R_3$, and A are each defined as those defined in claim 1;

Route 2:

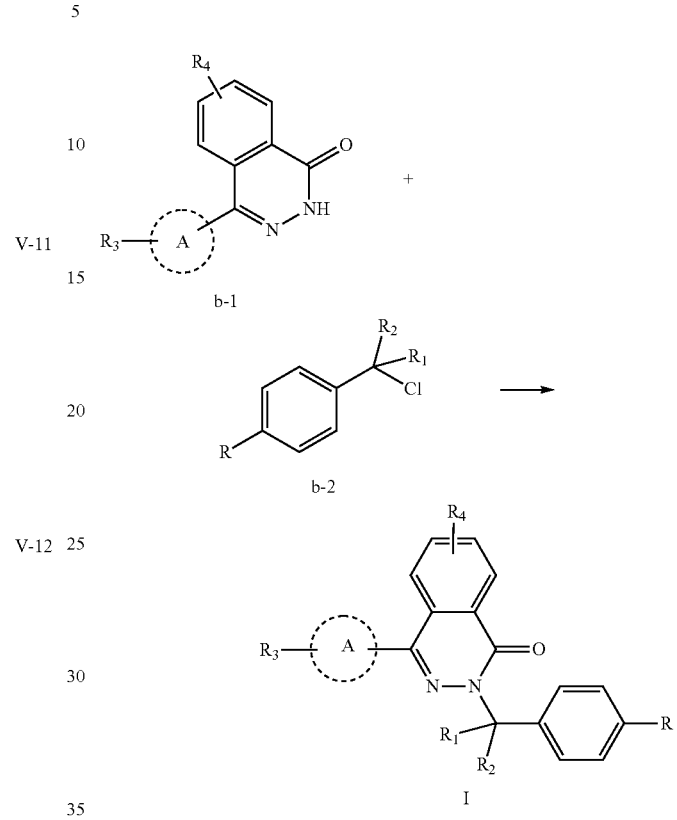

the compound I is obtained from the compound b-1 and the compound b-2 by a nucleophilic substitution, wherein, R, $R_1$, $R_2$, $R_3$, $R_4$ and A are each defined as those defined in claim 1.

6. A pharmaceutical composition comprising a therapeutically effective amount of one or more selected from the group consisting of the compound of formula I, or a pharmaceutically acceptable salt, solvate or prodrug thereof according to claim 1, and an optional pharmaceutically acceptable carrier.

7. A method for treating hepatitis B disease in a subject, comprising: administering an effective amount of the compound of formula I or a pharmaceutically acceptable salt, solvate or prodrug thereof according to claim 1 to the subject.

8. A method for inhibiting hepatitis B virus replication in a subject, comprising administering an effective amount of the compound of formula I or a pharmaceutically acceptable salt, solvate or prodrug thereof according to claim 1 to the subject.

9. A method for treating hepatitis B disease in a subject, comprising administering an effective amount of the pharmaceutical composition according to claim 6 to the subject.

10. A method for inhibiting hepatitis B virus replication in a subject, comprising administering an effective amount of the pharmaceutical composition according to claim 6 to the subject.

11. The compound of formula I, or a pharmaceutically acceptable salt, or solvate or prodrug thereof according to claim 1, wherein, $R_3$ represents one or more substituents, each being independently selected from the group consisting of H, D, halogen, cyano, trifluoromethyl, methyl optionally substituted by one or more D, methylol, methoxymethyl optionally substituted by one or more D, acetoxymethyl, methoxy optionally substituted by one or more D, amino, methylamino, dimethylamino, t-butylamino, cyclopropylamino, epoxypropylamino, acetylamino, oxetanylamino, methoxymethylamino, cyclobutylamino, azetidinyl, N,N-dimethylaminomethylamino, N,N-dimethylaminoethylamino, 6-morpholinylmethyl, 6-(tetrahydrofuranyl)methylamino, with the proviso that when A is pyridyl and R is Cl, $R_3$ is not H or D.

12. The compound of formula I, or a pharmaceutically acceptable salt, solvate or prodrug thereof according to claim 2, wherein:
- in the formula I-I, $R_1$ and $R_2$ are each independently H or D; $R_3$ represents one or more substituents, each being independently selected from the group consisting of halogen, cyano, $C_1$-$C_5$ linear or branched alkyl optionally substituted by one or more D, trifluoromethyl, $C_3$-$C_6$ cycloalkyl, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing 1-2 nitrogen atoms, —$(CH_2)_{n+1}R^5$ optionally substituted by one or more D, —$N(R^6)$—$(CH_2)_n(R^5)$; wherein, n is 0, 1, 2, 3 or 4; $R^5$ and $R^6$ are each independently H, hydroxyl, methyl, ethyl, propyl, isopropyl, butyl, isobutyl, $C_3$-$C_6$ cycloalkyl, methoxy, ethoxy, acetoxy, 4- to 6-membered non-aromatic heterocyclyl having 1-2 heteroatoms selected from the group consisting of N and O, or amino substituted by 1-2 substituents selected from the group consisting of methyl, ethyl;
- in the formula I-II, $R_1$ and $R_2$ are each independently H or D; $R_3$ represents 1 or 2 substituents, each being independently selected from the group consisting of H, D, halogen, cyano, trifluoromethyl, $C_1$-$C_7$ linear or branched alkyl optionally substituted by one or more D, $C_1$-$C_6$ linear or branched alkoxy optionally substituted by one or more D, —$N(R^6)$—$(CH_2)_n(R^5)$; wherein, n is 0, 1, 2, 3 or 4; $R^5$ and $R^6$ are each independently H, halogen, methyl, ethyl, propyl, isopropyl, butyl or isobutyl;
- in the formula I-III, $R_1$ and $R_2$ are each independently H or D; $R_3$ represents 1 or 2 substituents, each being independently selected from the group consisting of H, D, halogen, cyano, trifluoromethyl, $C_1$-$C_7$ linear or branched alkyl optionally substituted by one or more D, $C_1$-$C_6$ linear or branched alkoxy optionally substituted by one or more D, or —$N(R^6)$—$(CH_2)_n(R^5)$; wherein, n is 0, 1, 2, 3 or 4; $R^5$ and $R^6$ are each independently H, methyl, ethyl, propyl, isopropyl, butyl;
- in formula I-IV, $R_1$ and $R_2$ are each independently H or D; $R_3$ represents one or more substituents, each being independently selected from the group consisting of H, D, halogen, cyano, hydroxyl, trifluoromethyl, $C_3$-$C_6$ cycloalkyl, $C_1$-$C_5$ linear or branched alkyl optionally substituted by one or more D, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing N, —$(CH_2)_{n+1}R^5$ optionally substituted by one or more D, —$N(R^6)$—$(CH_2)_n(R^5)$; wherein, n is 0, 1, 2, 3 or 4; $R^5$ and $R^6$ are each independently H, hydroxyl, methyl, ethyl, propyl, isopropyl, butyl, isobutyl, t-butyl, $C_3$-$C_6$ cycloalkyl, methoxy, ethoxy, methoxyethoxyethoxy, ethoxyethoxy, acetyl, acetyloxy, methoxycarbonyl, ethoxycarbonyl, t-butoxycarbonyl, t-butoxycarbonylmethoxy, carboxyl, carboxymethoxy, 4- to 6-membered non-aromatic heterocyclyl with 1-2 heteroatoms selected from the group consisting of N and O, or amino substituted by 1-2 substituents selected from the group consisting of methyl, ethyl and t-butoxycarbonyl, methylsulfonyl, 2,2-dimethyl-[1,3]-dioxolan-4-yl, 2,3-dihydroxypropyl, 2-hydroxypropyl, trifluoromethylethyl;
- in formula I-V, R represents Cl or CN; $R_1$ and $R_2$ are each independently H or D; $R_3$ represents one or more substituents, each being independently selected from the group consisting of H, D, halogen, cyano, hydroxyl, trifluoromethyl, $C_3$-$C_6$ cycloalkyl, $C_1$-$C_5$ linear or branched alkyl optionally substituted by one or more D, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing N, —$(CH_2)_{n+1}R^5$ optionally substituted by one or more D, —$N(R^6)$—$(CH_2)_n(R^5)$; wherein n is 0, 1, 2, 3 or 4; $R_4$ represents one or more substituents, each being independently selected from the group consisting of halogen, cyano, trifluoromethyl, methyl, ethyl, methoxy; $R^5$ and $R^6$ are each independently H, hydroxyl, methyl, ethyl, propyl, isopropyl, butyl, isobutyl, t-butyl, $C_3$-$C_6$ cycloalkyl, methoxy, ethoxy, methoxyethoxyethoxy, ethoxyethoxy, acetyl, acetoxyl, methoxycarbonyl, ethoxycarbonyl, t-butoxycarbonyl, t-butoxycarbonylmethoxy, carboxyl, carboxymethoxy, 4- to 6-membered non-aromatic heterocyclyl with 1-2 heteroatoms selected from the group consisting of N and O, or amino substituted by 1-2 substituents selected from the group consisting of methyl and ethyl, methylsulfonyl, 2,2-dimethyl-[1,3]-dioxolan-4-yl, 2,3-dihydroxypropyl, 2-hydroxypropyl, trifluoromethylethyl.

13. The compound of formula I, or a pharmaceutically acceptable salt, solvate or prodrug thereof according to claim 2, wherein:
- in formula I-IV, $R_1$ and $R_2$ are each independently H or D; $R_3$ represents one or more substituents, each being independently selected from the group consisting of H, D, halogen, cyano, trifluoromethyl, $C_3$-$C_6$ cycloalkyl, $C_1$-$C_5$ linear or branched alkyl optionally substituted by one or more D, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing N, —$(CH_2)_{n+1}R^5$ optionally substituted by one or more D, —$N(R^6)$—$(CH_2)_n(R^5)$; wherein, n is 0, 1, 2, 3 or 4; $R^5$ and $R^6$ are each independently H, hydroxyl, methyl, ethyl, propyl, isopropyl, butyl, isobutyl, $C_3$-$C_6$ cycloalkyl, methoxy, ethoxy, acetoxy, 4- to 6-membered non-aromatic heterocyclyl with 1-2 heteroatoms selected from the group consisting of N and O, or amino substituted by 1-2 substituents selected from the group consisting of methyl and ethyl;
- in formula I-V, R represents Cl or CN; $R_1$ and $R_2$ are each independently H or D; $R_3$ represents one or more substituents, each being independently selected from the group consisting of H, D, halogen, cyano, trifluoromethyl, $C_3$-$C_6$ cycloalkyl, $C_1$-$C_5$ linear or branched alkyl optionally substituted by one or more D, $C_1$-$C_5$ linear or branched alkyl optionally substituted by one or more D in which any carbon atom may be replaced by an oxygen atom, $C_1$-$C_5$ linear or branched alkoxy optionally substituted by one or more D, 3- to 6-membered saturated heterocyclyl containing N, —$(CH_2)_{n+1}$ $R^5$ optionally substituted by one or more D, —$N(R^6)$—$(CH_2)_n(R^5)$; wherein n is 0, 1, 2, 3 or 4; $R_4$ represents one or more substituents, each being independently selected from the group consisting of halogen, cyano, trifluoromethyl, methyl, ethyl, methoxy; $R^5$ and $R^6$ are each independently H, hydroxyl, methyl, ethyl, propyl, isopropyl, butyl, isobutyl, $C_3$-$C_6$ cycloalkyl, methoxy, ethoxy, acetoxy, 4- to 6-membered non-aromatic heterocyclyl with 1-2 heteroatoms selected from the group consisting of N and O, or amino substituted by 1-2 substituents selected from the group consisting of methyl and ethyl.

14. The compound of formula I, or a pharmaceutically acceptable salt, or solvate thereof according to claim 3, wherein:
the pharmaceutically acceptable salt includes an alkali metal salt, an alkaline earth metal salt, an ammonium salt of the compound of formula I; and the alkali metal includes sodium, potassium, lithium, cesium, and the alkaline earth metal includes magnesium, calcium, strontium;
the pharmaceutically acceptable solvent includes water, ethanol, acetic acid, N,N-dimethyl formamide and dimethyl sulfoxide.

15. The compound of formula I, or a pharmaceutically acceptable salt, or solvate thereof according to claim 3, wherein:
the pharmaceutically acceptable salt includes a salt formed by the compound of formula I and an organic base, or a slat formed by the compound of formula I and an acid;
the pharmaceutically acceptable solvent is water.

16. The compound of formula I, or a pharmaceutically acceptable salt, or solvate thereof according to claim 15, wherein:
the organic base includes trialkylamine, pyridine, quinoline, piperidine, imidazole, picoline, dimethylaminopyridine, dimethylaniline, N-alkylmorpholine, 1,5-diazabicyclo[4.3.0]non-5-ene, 1,8-diazabicyclo[5.4.0]undec-7-ene,1,4-diazabicyclo[2.2.2]octane;
the acid includes an inorganic acid and an organic acid; wherein the inorganic acid includes hydrochloric acid, hydrobromic acid, hydroiodic acid, sulfuric acid, nitric acid, phosphoric acid, carbonic acid; and the organic acid includes formic acid, acetic acid, propionic acid, oxalic acid, malonic acid, succinic acid, fumaric acid, maleic acid, lactic acid, malic acid, citric acid, citric acid, tartaric acid, carbonic acid, picric acid, methanesulfonic acid, ethanesulfonic acid, p-toluenesulfonic acid, glutamic acid, pamoic acid.

* * * * *